(12) United States Patent (10) Patent No.: US 8,765,235 B2
Mizumura et al. (45) Date of Patent: *Jul. 1, 2014

(54) POLYMERIZABLE COMPOUND

(71) Applicant: Fujifilm Corporation, Tokyo (JP)

(72) Inventors: Masatoshi Mizumura, Ashigarakami-gun (JP); Shunya Katoh, Ashigarakami-gun (JP); Yasuhiro Ishiwata, Ashigarakami-gun (JP); Masaomi Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/716,372

(22) Filed: Dec. 17, 2012

(65) Prior Publication Data

US 2013/0123453 A1 May 16, 2013

Related U.S. Application Data

(63) Continuation of application No. PCT/JP2011/064258, filed on Jun. 22, 2011.

(30) Foreign Application Priority Data

Jun. 22, 2010 (JP) ................................. 2010-141469

(51) Int. Cl.
*G02B 1/04* (2006.01)
*G02B 5/30* (2006.01)
*C07C 251/24* (2006.01)
*C09K 19/38* (2006.01)
*C08F 20/36* (2006.01)

(52) U.S. Cl.
USPC ...... 428/1.1; 428/1.33; 252/299.67; 558/302; 560/61; 560/87; 560/88; 560/89; 526/292.2; 526/312

(58) Field of Classification Search
USPC ............. 252/299.01, 299.65, 299.66, 299.67; 428/1.3, 1.1, 1.33; 558/302; 560/61, 560/87, 88, 89; 526/292.2, 312
See application file for complete search history.

(56) References Cited

U.S. PATENT DOCUMENTS 7,435,357 B2 * 10/2008 Harding et al. ............. 252/299.1

FOREIGN PATENT DOCUMENTS

| JP | 2007-206461 A | 8/2007 |
|---|---|---|
| JP | 2007-279363 A | 10/2007 |
| JP | 2008-203709 A | 9/2008 |
| JP | 2009-149754 A | 7/2009 |

OTHER PUBLICATIONS

English translation by computer for JP 2007/206461, http://www4.ipdl.inpit.go.jp/Tokujitu/PAJdetail.ipdl?N0000=60&NO120=01&N2001=2&N3001=2007-206461, 2007.*
CAPLUS 1998: 280179.*
Marie-Andrée Guillevic, et al., "Structure-property relationships in *ortho*-metallated imine complexes of Re(I)", Polyhedron, 2000, pp. 249-257, vol. 19, No. 3.
Dirk J. Broer, et al., "Photo-Induced Diffusion in Polymerizing Chiral-Nematic Media", Advanced Materials, 1999, pp. 573-578, vol. 11, No. 7.
International Preliminary Report on Patentability (with English translation) in PCT/JP2011/064258 mailed Jan. 10, 2013.
Written Opinion of the International Searching Authority (with English translation) in PCT/JP2011/064258 mailed Jan. 24, 2013.

* cited by examiner

*Primary Examiner* — Shean C Wu
(74) *Attorney, Agent, or Firm* — Sughrue Mion, PLLC

(57) ABSTRACT

Provided is a novel polymerizable azomethine compound which has a high Δn and is colorless.
The compound is represented by the formula (I). $P^1$ and $P^2$ each are a polymerizable group; m1 and m2 each are an integer of from 1 to 10; $R^1$ and $R^2$ each are an alkyl group having from 1 to 4 carbon atoms, an alkoxy group having from 1 to 4 carbon atoms, an alkoxycarbonyl group having from 2 to 5 carbon atoms, an acyloxy group having from 2 to 5 carbon atoms, an acyl group having from 2 to 4 carbon atoms, an amide group having from 2 to 5 carbon atoms, a cyano group or a halogen atom; n1 and n2 each are an integer of from 0 to 4; $R^3$ is a hydrogen atom, or an alkyl group having from 1 to 4 carbon atoms; $Z^1$ and $L^1$ each are a predetermined divalent group; n is 0, 1 or 2.

16 Claims, 2 Drawing Sheets

POLYMERIZABLE COMPOUND

CROSS-REFERENCE TO RELATED APPLICATIONS

This application is a continuation application of International Application No. PCT/JP2011/064258, filed Jun. 22, 2011, which in turn claims the benefit of priority from Japanese Application No. 2010-141469, filed Jun. 22, 2010, the disclosures of which applications are incorporated by reference herein in their entirety.

BACKGROUND OF THE INVENTION

1. Field of the Invention

The present invention relates to a polymerizable composition useful in various uses typically for materials for various types of optical members such as optically anisotropic films, heat insulating films, etc.

2. Description of the Related Art

These days downsizing of liquid-crystal display devices is desired, and with that, thinning of optical films is also desired. For example, using a liquid crystal having a high Δn in an optical film such as retardation film or the like makes it possible to reduce the thickness of the film. Δn is one of important basic physical properties of a liquid-crystal compound; and a liquid crystal having a high Δn can be utilized in many industrial fields of retardation plates, polarizing elements, selective reflection films, color filters, antireflection films, viewing angle compensation films, holography, alignment films and others that are constituent elements of optical devices (Non-Patent Document 1).

Heretofore, various types of compounds having an azomethine bond have been proposed as polymerizable liquid-crystal compounds (Patent Documents 1 to 4).

CITATION LIST

Patent Documents

Patent Document 1: JP-A 2007-279363
Patent Document 2: JP-A 2007-206461
Patent Document 3: JP-A 2009-149754
Patent Document 4: JP-A 2008-203709

Non-Patent Document

Non-Patent Document 1: D. J. Broer, G. N. Mol, J. A. M. M. Van Haaren, and J. Lub Adv. Mater., 1999, 11, 573

SUMMARY OF THE INVENTION

For increasing Δn of a polymerizable liquid crystal, it is known to make the compound absorbable long-wave light; however, when the wavelength of the light that the compound can absorb is too much prolonged, then there occurs a problem in that the compound may color. Consequently, in case where use of colorless compounds is simulated, it is important to attain a high Δn within a prolonged wavelength range within which the compounds do not color. Polymerizable azomethine liquid-crystal compounds heretofore known in the art have problems in that their Δn is insufficient or even polymerizable azomethine liquid-crystal compounds capable of attaining a high Δn would absorb long-wave light and may therefore color.

An object of the invention is to provide a novel, colorless polymerizable azomethine compound which has a high Δn and which has good solubility in solvent and good miscibility with any other liquid-crystal material.

The means for solving the above-mentioned problems are as follows:

[1] A compound represented by the following formula (I):

[Chemical formula 1]

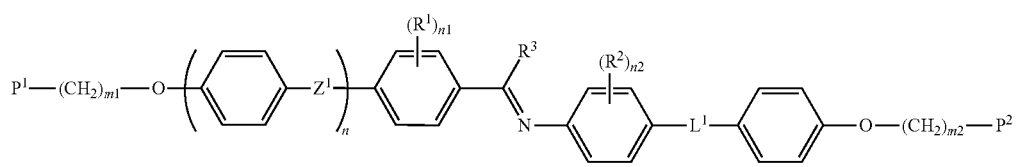

(I)

wherein $P^1$ and $P^2$ each represent a polymerizable group; m1 and m2 each indicate an integer of from 1 to 10, and of m1 or m2 $CH_2$'s, one $CH_2$ or two or more $CH_2$'s not adjacent to each other may be replaced by an oxygen atom or a sulfur atom; $R^1$ and $R^2$ each represent an alkyl group having from 1 to 4 carbon atoms, an alkoxy group having from 1 to 4 carbon atoms, an alkoxycarbonyl group having from 2 to 5 carbon atoms, an acyloxy group having from 2 to 5 carbon atoms, an acyl group having from 2 to 4 carbon atoms, an amide group having from 2 to 5 carbon atoms, a cyano group or a halogen atom; n1 and n2 each indicate an integer of from 0 to 4; $R^3$ represents a hydrogen atom, or an alkyl group having from 1 to 4 carbon atoms;
$Z^1$ represents —COO—, —OCO—, —COS—, —SCO— or —NHCO—;
$L^1$ represents —COO—, —OCO—, —COS—, —SCO—, —OCO—CH=CH— or —NHCO—;
n is 0, 1 or 2.

[2] The compound of [1], wherein in the formula (I), when n=0, $L^1$ is —OCO— or —OCO—CH=CH—.

[3] The compound of [1], wherein in the formula (I), when n=1, $Z^1$ is —COO— and $L^1$ is —OCO—.

[4] The compound of any of [1] to [3], wherein in the formula (I), $P^1$ and $P^2$ each are a polymerizable group selected from the groups represented by the following formulae (P-1) to (P-5):

(P-1)

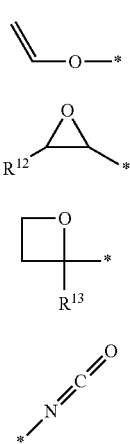

(P-2)

(P-3)

(P-4)

(P-5)

wherein $R^{11}$ to $R^{12}$ each represent a hydrogen atom or a methyl group.

[5] The compound of any of [1] to [4], wherein in the formula (I), $P^1$ and $P^2$ each are a methacrylate group or an acrylate group.

[6] The compound of any of [1] to [5], wherein in the formula (I), m1 and m2 each are from 2 to 8.

According to the invention, there is provided a novel, colorless polymerizable azomethine compound which has a high Δn and which has good solubility in solvent and good miscibility with any other liquid-crystal material.

MODE FOR CARRYING OUT THE INVENTION

Figure 1:
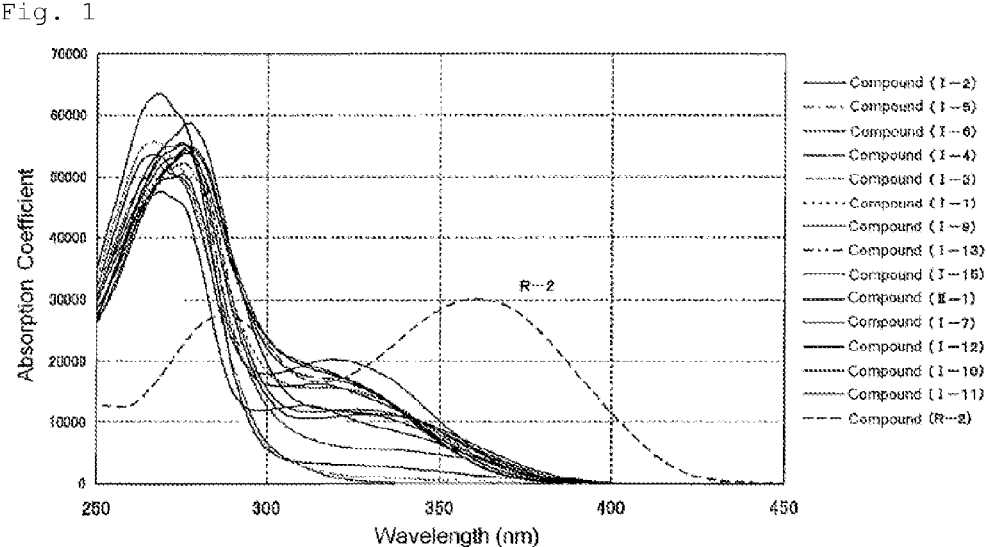
[FIG. 1] This shows absorption spectrum curves of compounds of the formula (I) and a comparative compound, as measured in Examples.

The invention is described in detail hereinunder. In this description, the numerical range expressed by the wording "a number to another number" means the range that falls between the former number indicating the lower limit of the range and the latter number indicating the upper limit thereof.

1. Polymerizable Compound

The invention relates to a polymerizable compound represented by the following formula (I). The compound of the following formula (I) is characterized by having one azomethine group in the molecule along with a mesogen therein. A liquid-crystal compound having an azomethine group in the molecule shows a high Δn, but on the other hand, a conventional bisazomethine liquid-crystal compound having two azomethine groups in the molecule has a problem of yellowing and therefore its use is limited. The compounds of the following formula (I) show a sufficiently high Δn and are white, and therefore these are free from a problem of coloration. Further, in the compounds of the following formula (I), the side chain that links the terminal polymerizable group to the mesogen therein is long, and therefore the temperature range in which the compounds are in a liquid phase could be broad. Consequently, the compounds solve the problem that they may crystallize in a polymerization process to be cloudy. Further, the solubility of the compounds in solvent and the miscibility thereof with any other liquid crystal material are both good, and they can cure through polymerization. Consequently, the compounds are useful in various applications for optical members, etc. In particular, since their Δn is high, the compounds are useful in production of optical films such as retardation films, selective reflection films and others that are required to show desired optical characteristics in the form of thin films.

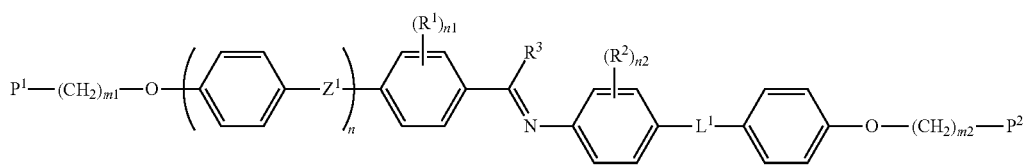

(I)

In the formula, $P^1$ and $P^2$ each represent a polymerizable group;

m1 and m2 each indicate an integer of from 1 to 10, and of m1 or m2 $CH_2$'s, one $CH_2$ or two or more $CH_2$'s not adjacent to each other may be replaced by an oxygen atom or a sulfur atom;

$R^1$ and $R^2$ each represent an alkyl group having from 1 to 4 carbon atoms, an alkoxy group having from 1 to 4 carbon atoms, an alkoxycarbonyl group having from 2 to 5 carbon atoms, an acyloxy group having from 2 to 5 carbon atoms, an acyl group having from 2 to 4 carbon atoms, an amide group having from 2 to 5 carbon atoms, a cyano group or a halogen atom; n1 and n2 each indicate an integer of from 0 to 4;

$R^3$ represents a hydrogen atom, or an alkyl group having from 1 to 4 carbon atoms;

$Z^1$ represents —COO—, —OCO—, —COS—, —SCO— or —NHCO—;

$L^1$ represents —COO—, —OCO—, —COS—, —SCO—, —OCO—CH=CH— or —NHCO—;

n is 0, 1 or 2.

In the above-mentioned formula, $P^1$ and $P^2$ each represent a polymerizable group. The polymerizable group is preferably a radical-polymerizable or cationic-polymerizable polymerizable group. As the radical-polymerizable group, any radical-polymerizable group generally known in the art is usable here, and one preferred example thereof is a (meth) acrylate group (this is used as a term including both an acrylate group and a methacrylate group). In this case, it is known that the polymerization rate is generally high with an acrylate group, and therefore an acrylate group is preferable from the viewpoint of productivity improvement; however, a methacrylate group is also usable similarly as the polymerizable group in high-Δn liquid crystals. As the cationic-polymerizable group, any cationic-polymerizable group generally known in the art is usable here; and concretely, there are mentioned an alicyclic ether group, a cyclic acetal group, a cyclic lactone group, a cyclic thioether group, a spiro-orthoester group, a vinyloxy group, etc. Of those, preferred are an alicyclic ether group and a vinyloxy group, and more preferred are an epoxy group, an oxetanyl group, and a vinyloxy group. In the above-mentioned formula, $P^1$ and $P^2$ may be the same or different; or that is, the compound of the above-mentioned formula (I) may contain two or more different types of polymerizable groups. In that case, the compound may have polymerizable groups that differ in point of the polymerization reaction mechanism thereof, such as a radical-polymerizable group and a cationic-polymerizable group, etc., or may have polymerizable groups having the same reaction mechanism.

Preferably, $P^1$ and $P^2$ each are a polymerizable group represented by any of the following formulae (P-1) to (P-5):

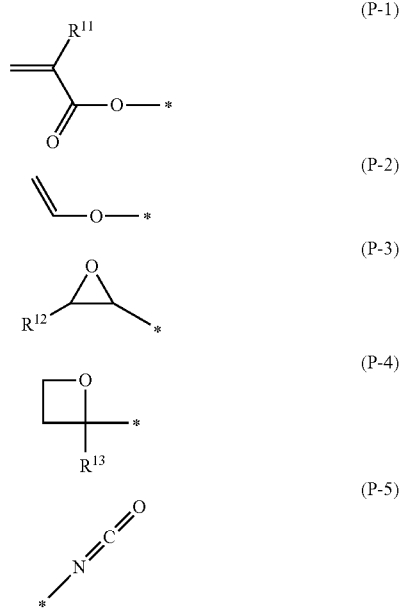

In the formulae, $R^{11}$ to $R^{13}$ each represent a hydrogen atom or a methyl group. * indicates the position at which the group bonds to the alkylene chain in the formulae.

Preferably, $P^1$ and $P^2$ each are a (meth)acrylate group, or that is, any of the following groups:

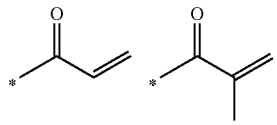

In the above-mentioned formula, m1 and m2 each indicate an integer of from 1 to 10. When the side chain is short (for example, when m1 and m2 each are from 1 to 3), then the uppermost temperature at which the compound can exhibit a liquid-crystal phase is high, but the compound may readily crystallize and its solubility lowers. Consequently, from the viewpoint of the solubility or the miscibility of the compound in or with any other ingredient (e.g., solvent or other liquid-crystal material) to be contained in a composition, the proportion of the compound of the type must be small. On the other hand, when the side chain is long (for example, when m1 and m2 each are from 4 to 6), then the solubility of the compound may increase but the uppermost temperature at which the compound can exhibit a liquid-crystal phase may lower or the compound may readily exhibit a smectic phase and the nematic liquid range of the compound may be narrow so that the alignment uniformity of the compound may lower. In addition, when the side chain is long, then the degree of freedom of the molecule movement may increase. Therefore, in the field of use where a highly rigid film quality is desired, it is desirable to use a compound having a short side chain. However, in the field of use where a non-brittle film is desired, it is desirable to use a compound having a long side chain. Of m1 or m2 $CH_2$'s in the above-mentioned formula (I), one $CH_2$ or two or more $CH_2$'s not adjacent to each other may be replaced by an oxygen atom or a sulfur atom. In the compound where —$CH_2$— is replaced by S or O, the rotation capacity around the linking group increases, or that is, the degree of freedom therearound increases, and therefore the compound of the type is effective for reducing film brittleness. Preferably, the nematic phase range of the compound of the above-mentioned formula (I) is enlarged as compared with that of other conventional azomethine compounds; and from this viewpoint, m1 and m2 each are preferably from 2 to 8, more preferably from 3 to 6.

Type and Number of Rings:

For attaining high Δn, the alignment regularity must be high, and for this, it is effective to raise the uppermost temperature for the liquid-crystal phase. In the compound for use in a composition of the invention, at least from 3 to 5 rings of cyclic aromatic groups are linked to each other, and the NI point (transition temperature from nematic liquid-crystal phase to isotropic phase) is high, and concretely, the compound shows an extremely high NI point of 160° C. or higher, therefore greatly contributing toward increasing Δn of the composition. The compound of the invention is a compound having from 3 to 5 aromatic rings, in which the aromatic ring increases the polarization degree in the long axis direction of the molecule, as compared with an unsaturated ring or a nonaromatic ring, therefore contributing toward increasing Δn of the compound. However, increasing the number of the rings may elevate or increase the melting point or the viscosity of the compound, and is therefore defective in the region where the compound is used for optical films in that the compound would readily crystallize in a coating process to worsen film uniformity.

Type and Number of Substituents:

For high Δn, long wave absorption is effective, which, however, is a cause of coloration by conventional bisazomethine-type liquid-crystal compounds. In the compound of the formula (I) in the invention, the type of the substituent on the two aromatic rings that are linked to each other via the azomethine bond therein has little influence on color development of the compound, and consequently, the compound may have any arbitrary substituent. From the viewpoint of the solubility of the compound, the substituents having atoms larger in size could more contribute toward the solubility, but those having atoms smaller in size lower the solubility and the alignability of the compound may also lower. From these, the compound preferably has substituents. Regarding the number of the substituents, when the number is larger, the solubility of the compound may be expected to increase more; but if too large, the liquid crystallinity of the compound may worsen, therefore 1 or 2 is desirable. That is, it is desirable that both n1 and n2 are 0, or one of them is 1 and the other is 0, or both of them are 1.

In view of these, the number of the rings in the compound is preferably 3 or 4, and n is preferably 0 or 1.

$R^1$ and $R^2$ each represent an alkyl group having from 1 to 4 carbon atoms, an alkoxy group having from 1 to 4 carbon atoms, an alkoxycarbonyl group having from 2 to 5 carbon atoms, an acyloxy group having from 2 to 5 carbon atoms, an acyl group having from 2 to 4 carbon atoms, an amide group having from 2 to 5 carbon atoms, a cyano group or a halogen atom (e.g., fluorine atom, chlorine atom, bromine atom, iodine atom). More preferably, these are any of an alkyl group having from 1 to 4 carbon atoms, an alkoxy group having from 1 to 4 carbon atoms, an amide group having from 2 to 5 carbon atoms, an alkoxycarbonyl group having from 2 to 5 carbon atoms or a halogen atom, even more preferably an alkyl group having from 1 to 4 carbon atoms, an alkoxy group having from 1 to 4 carbon atoms, an alkoxycarbonyl group having from 1 to 4 carbon atoms or a halogen atom.

n indicates 0, 1 or 2, and is preferably 0 or 1.

$R^3$ represents a hydrogen atom or an alkyl group having from 1 to 4 carbon atoms. Even when $R^3$ is a hydrogen atom, the compound could secure sufficient hydrolysis resistance for the intended use herein. In some use where extremely high hydrolysis resistance is needed, $R^3$ is preferably an alkyl group. Regarding the length of the alkyl group, when the alkyl group is too long, the liquid-crystal phase of the compound may be unstable. Consequently, $R^3$ is preferably short. Concretely, $R^3$ is preferably an alkyl group having from 1 to 4 carbon atoms, more preferably an alkyl group having from 1 to 3 carbon atoms, even more preferably an alkyl group having 1 or 2 carbon atoms.

Type of Linking Group:

As the linking groups that link the ring structures, preferred are those having a rigid structure for stabilizing the liquid phase (that is, for raising the NI point) of the compound. On the other hand, when too many rigid groups exist in the compound, then the solubility of the compound may lower owing to the increase in the crystallinity thereof, and the nematic liquid-crystal phase temperature range may narrow owing to stabilization of the smectic phase of the compound. However, a single bond that gives a rigid structure may have a risk of coloration owing to π-conjugation enlargement to cause prolongation of the wavelength of light to be absorbed by the compound. Consequently, a single bond is unfavorable for the linking group to the skeleton having an azomethine bond. Concretely, in the above-mentioned formula, $Z^1$ represents —COO—, —OCO—, —COS—, —SCO— or —NHCO—, more preferably —COO—, —OCO—, —COS— or —SCO—, even more preferably —COO— or —OCO—. In the formula, $L^1$ represents —COO—, —OCO—, —COS—, —SCO—, —OCO—CH=CH— or —NHCO—, and is more preferably —COO—, —OCO—, —COS—, —SCO— or —OCO—CH=CH—, even more preferably —COO—, —OCO— or —OCO—CH=CH—.

In the formula (I), when n=0, $L^1$ is preferably —OCO— or —OCO—CH=CH—.

In the formula (I), when n=1, $Z^1$ is preferably —COO— and $L^1$ is preferably —OCO—.

Specific examples of the compound represented by the above-mentioned formula (I) are given below; however, the invention is not limited at all to these specific examples.

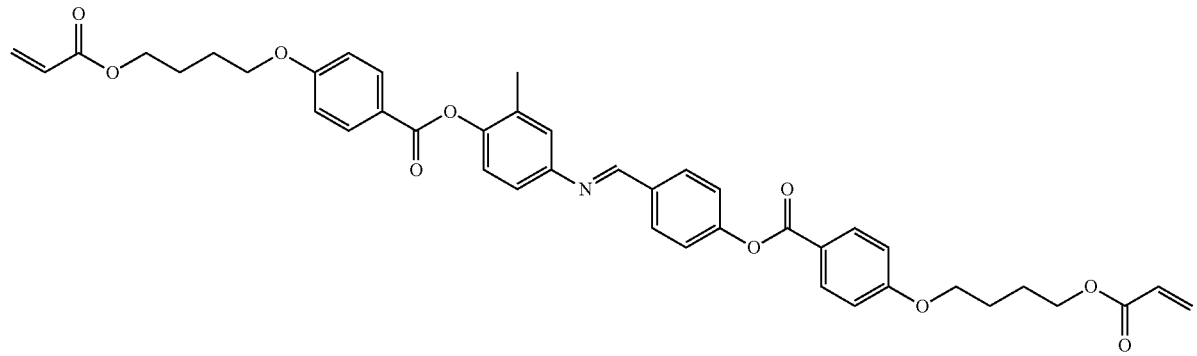

(I-1)

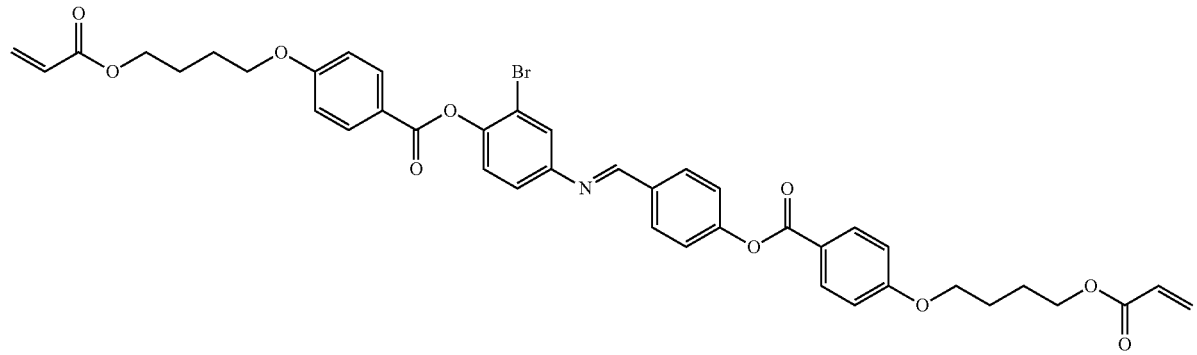

(I-2)

-continued
(I-3)
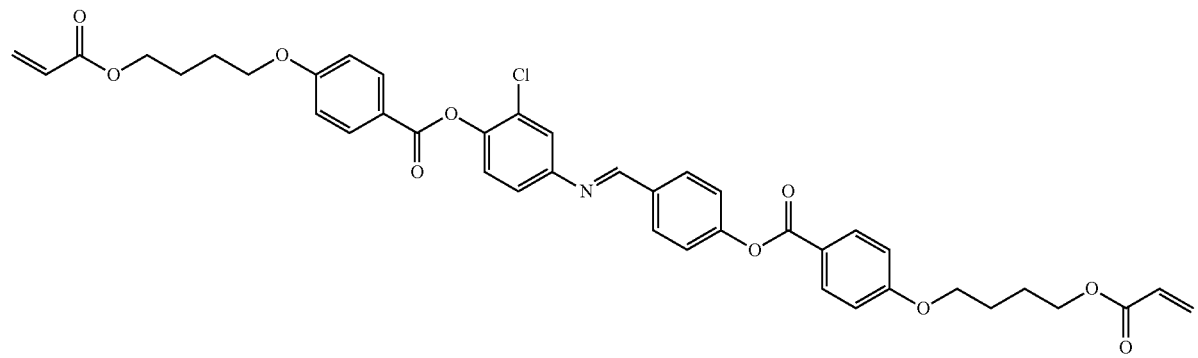
(I-4)
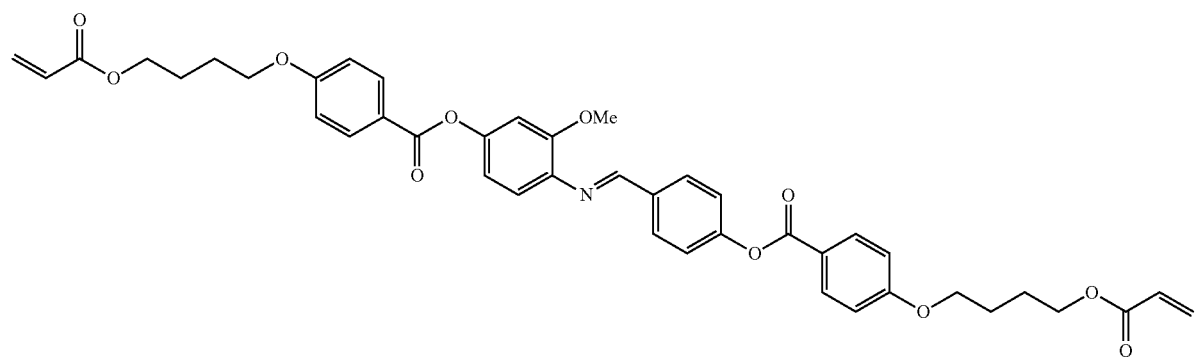
(I-5)
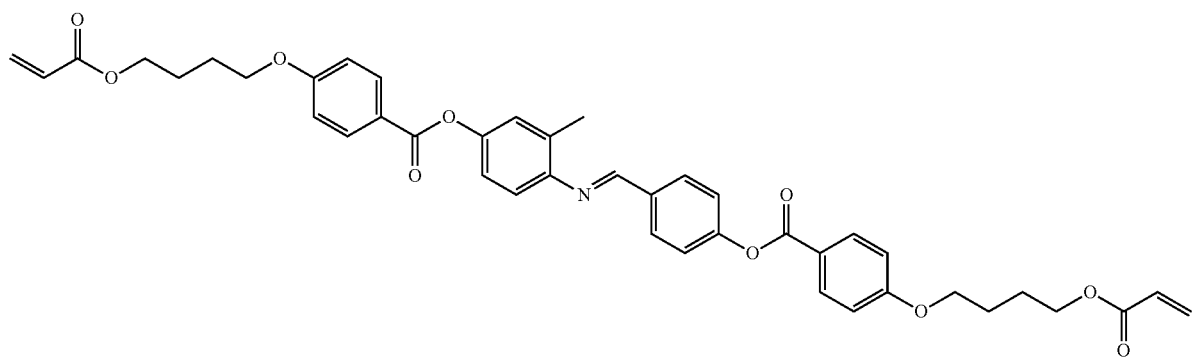
(I-6)
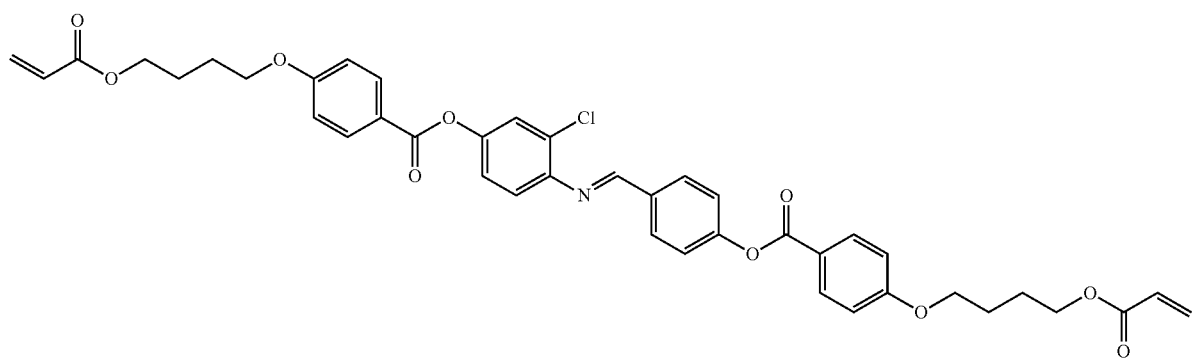

(I-7)
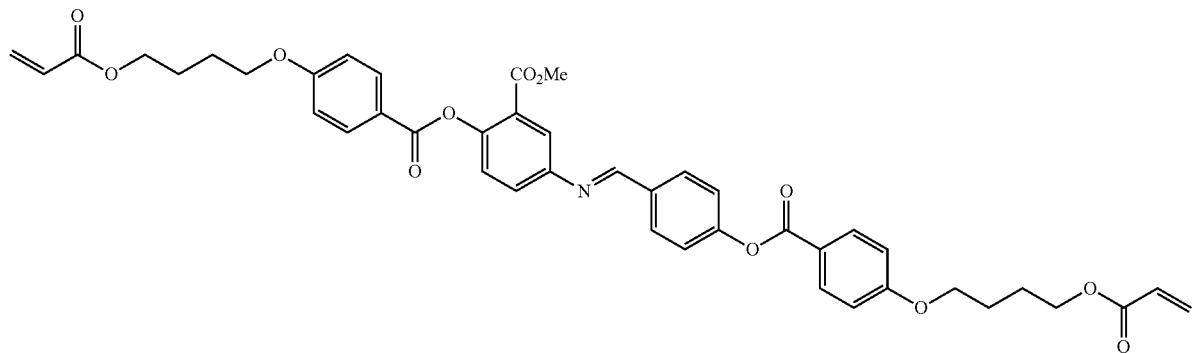
(I-8)
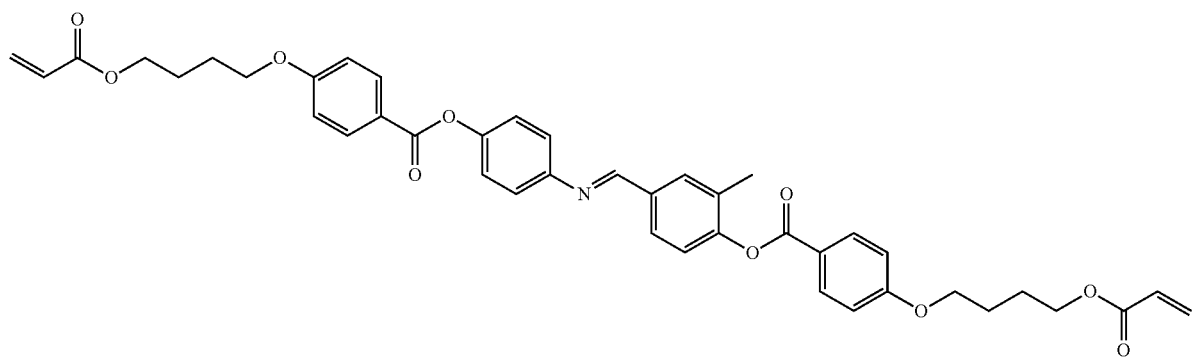
(I-9)
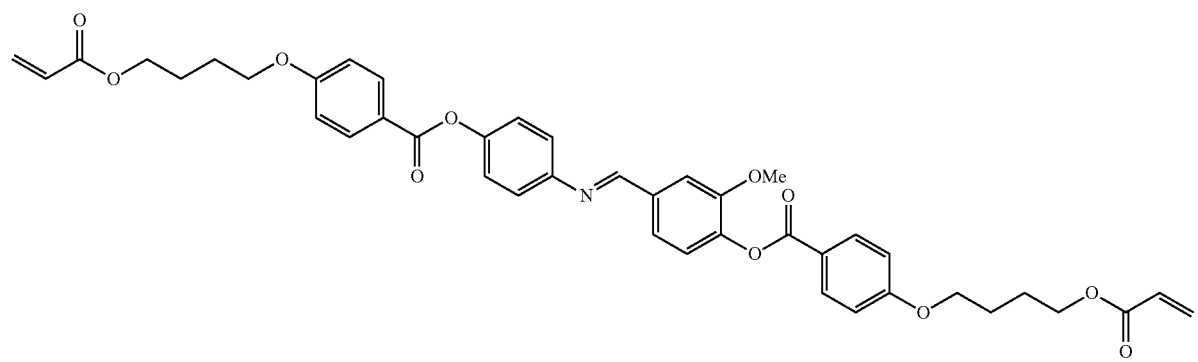
(I-10)
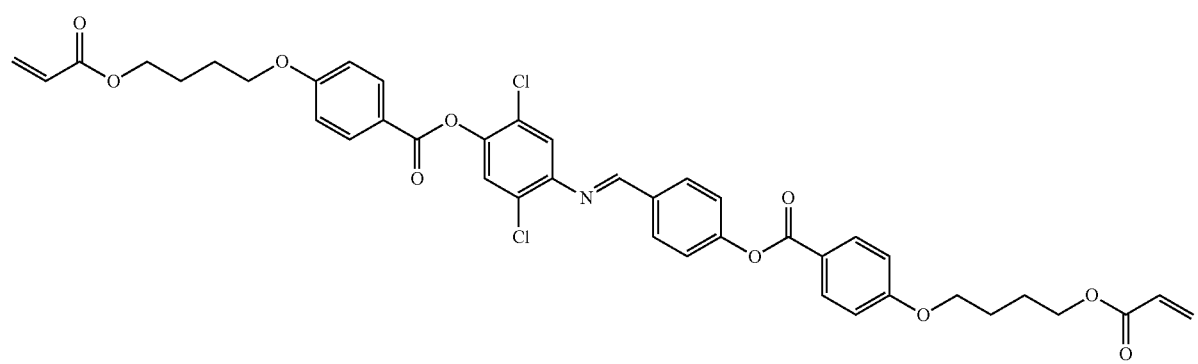

-continued
(I-11)
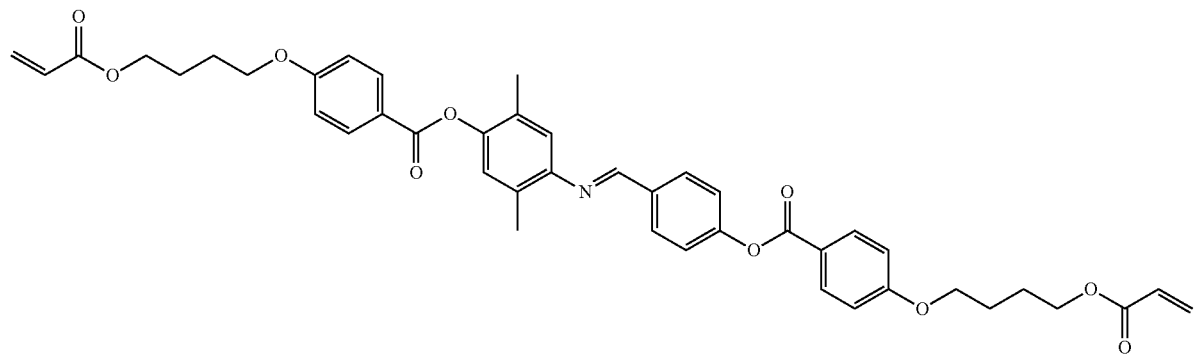
(I-12)
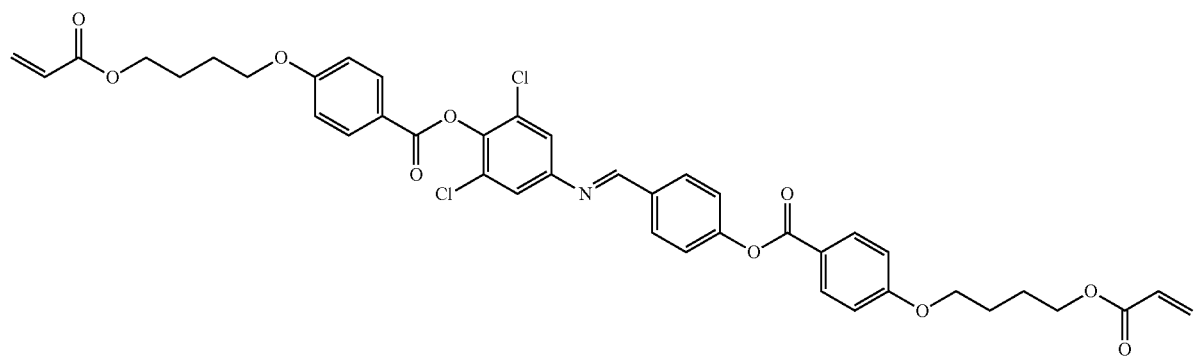
(I-13)
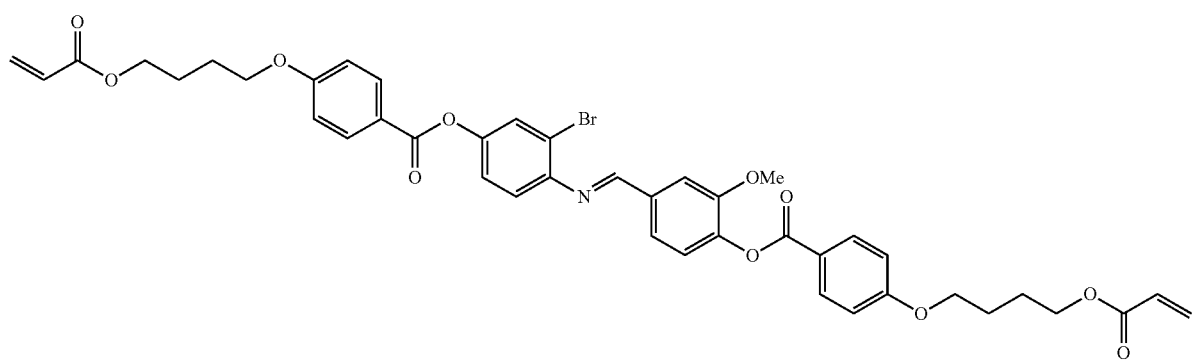
(I-14)
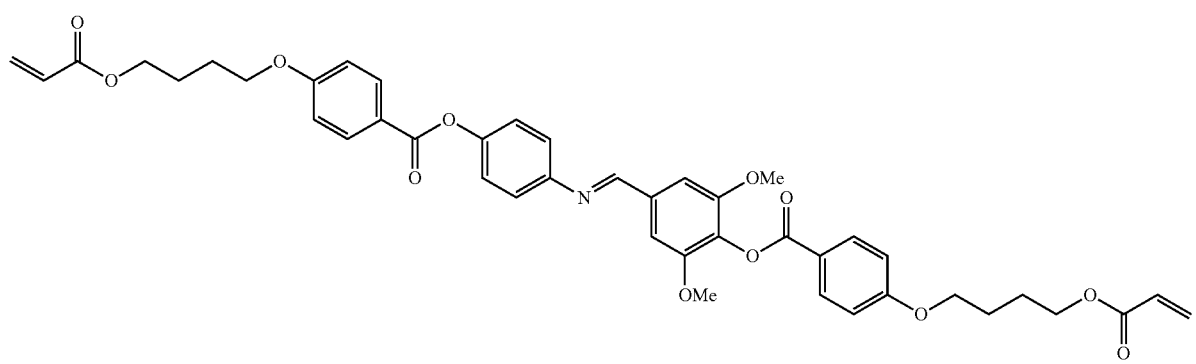

-continued
(I-15)
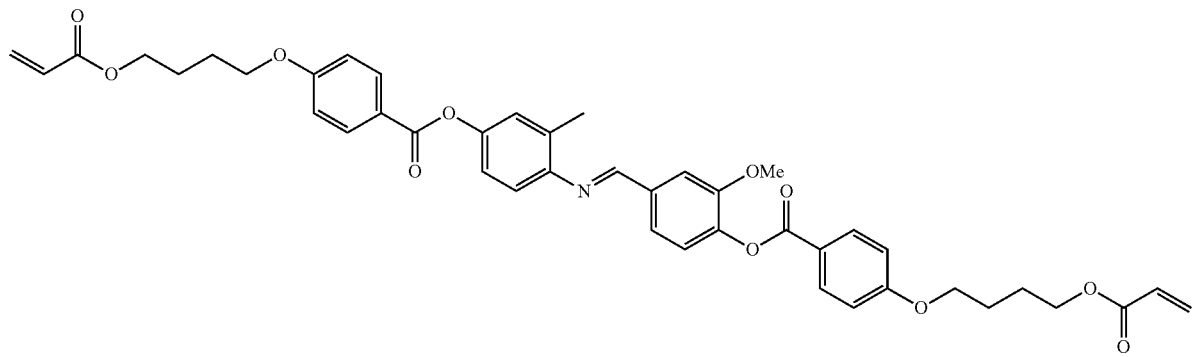
(I-16)
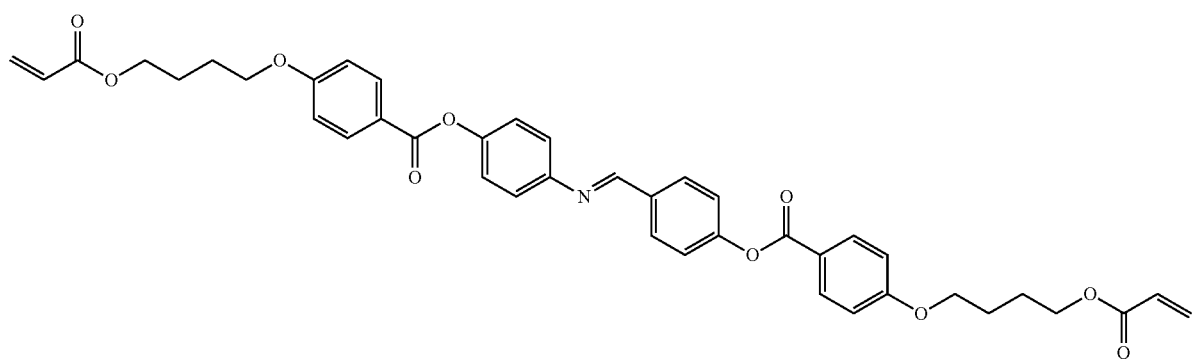
(II-1)
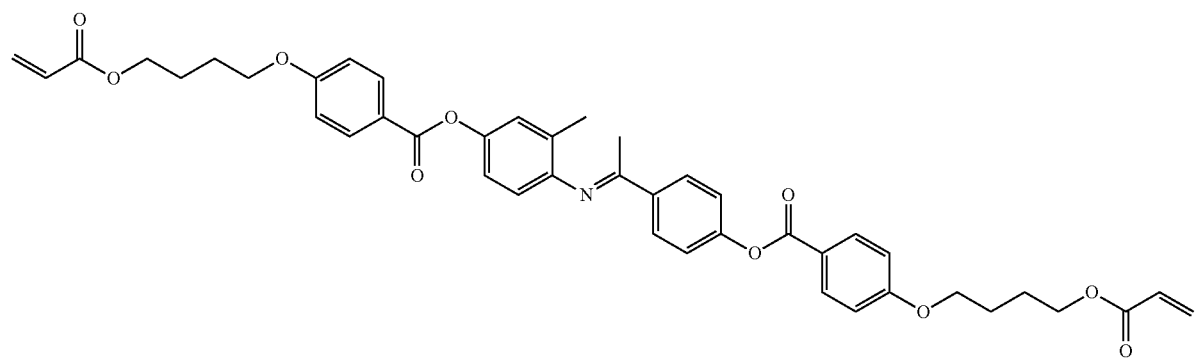
(II-2)
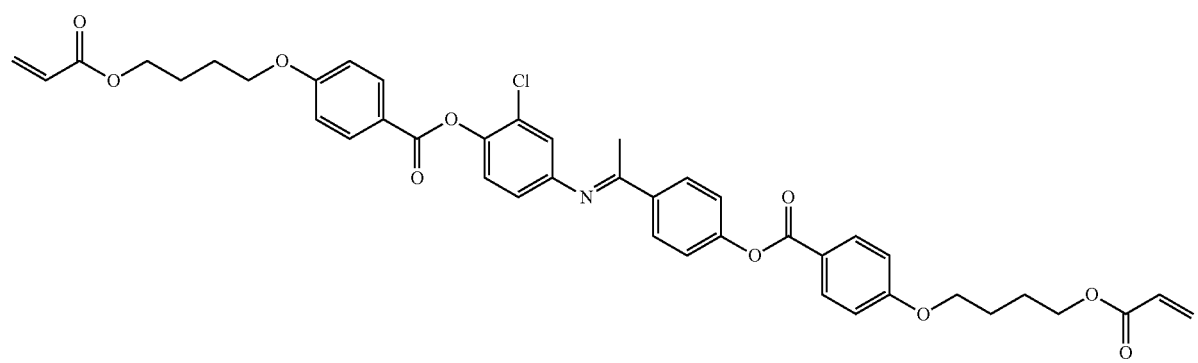

(II-3)
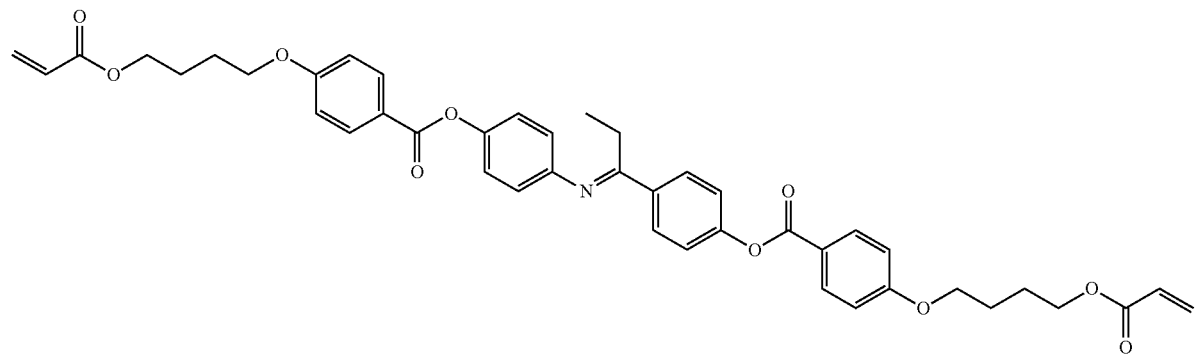
(II-4)
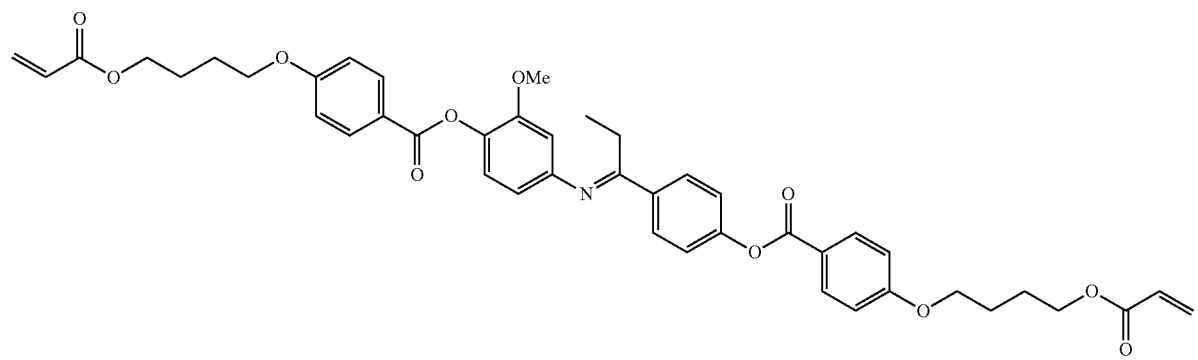
(II-5)
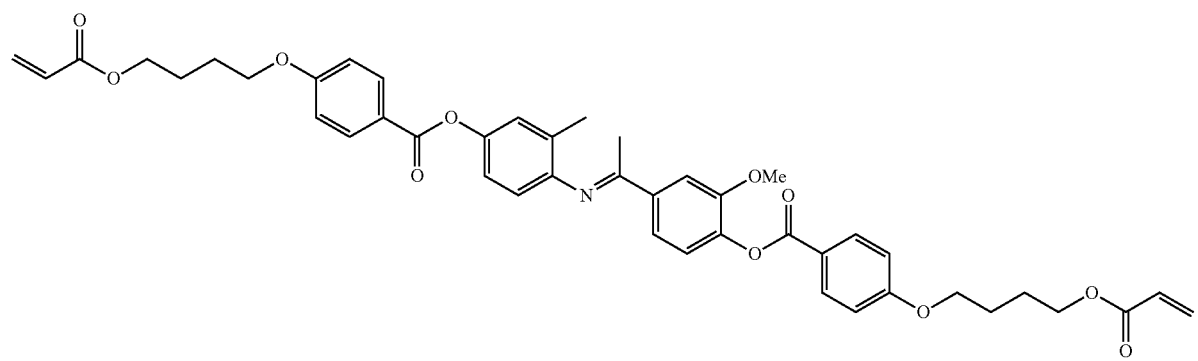
(II-6)
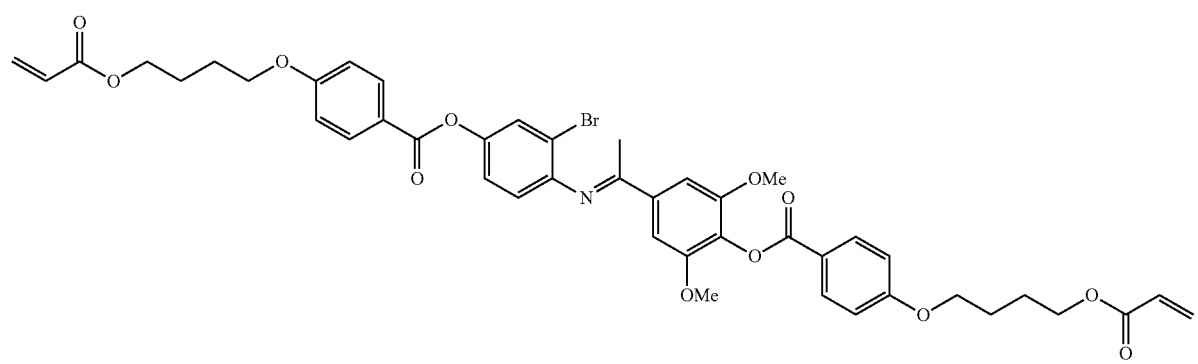

(II-7)
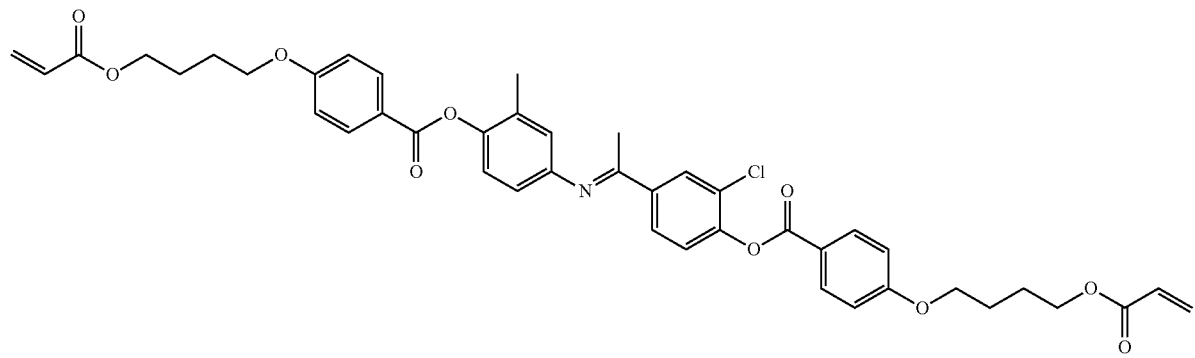
(II-8)
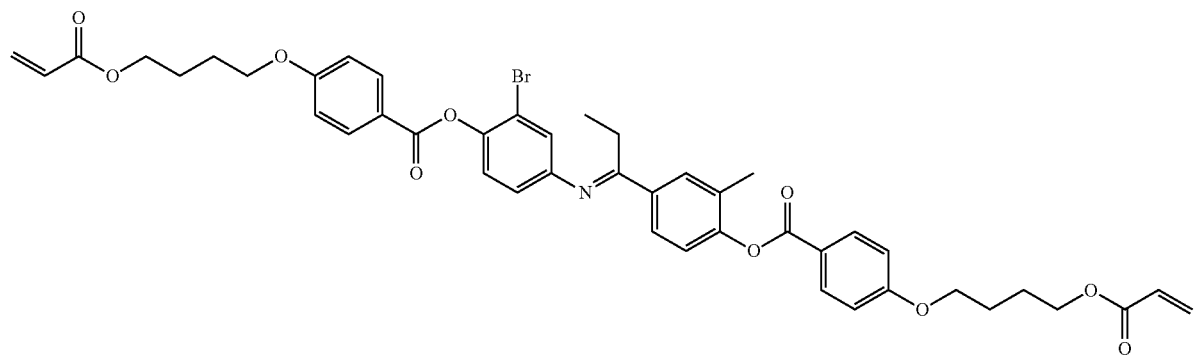
(III-1)
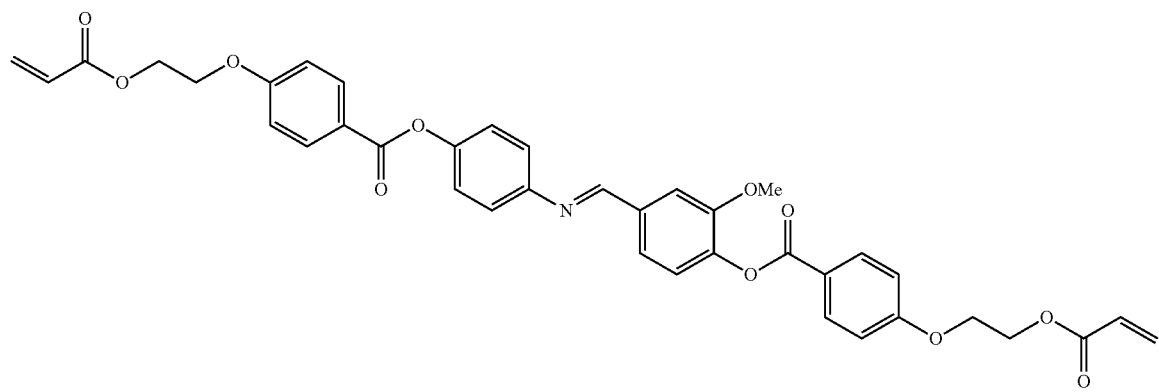
(III-2)
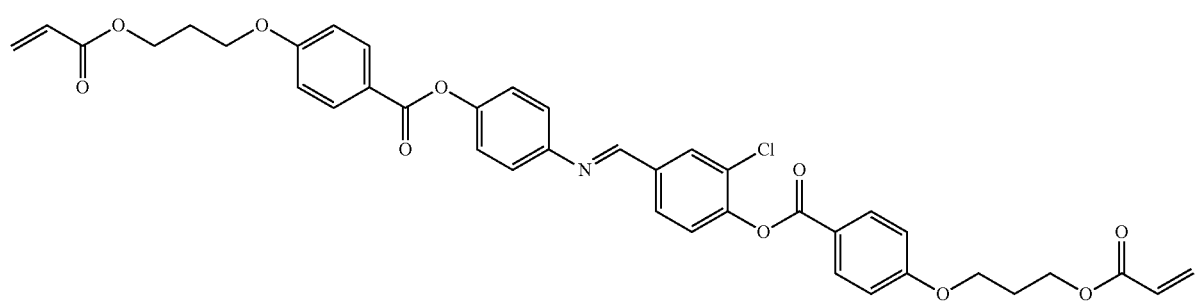

(III-3)
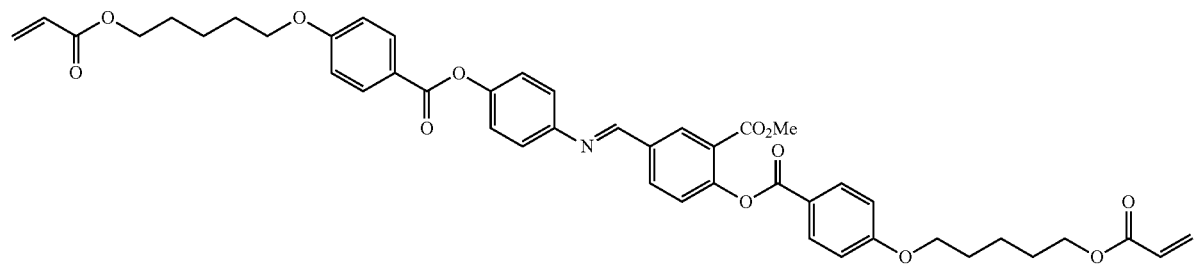
(III-4)
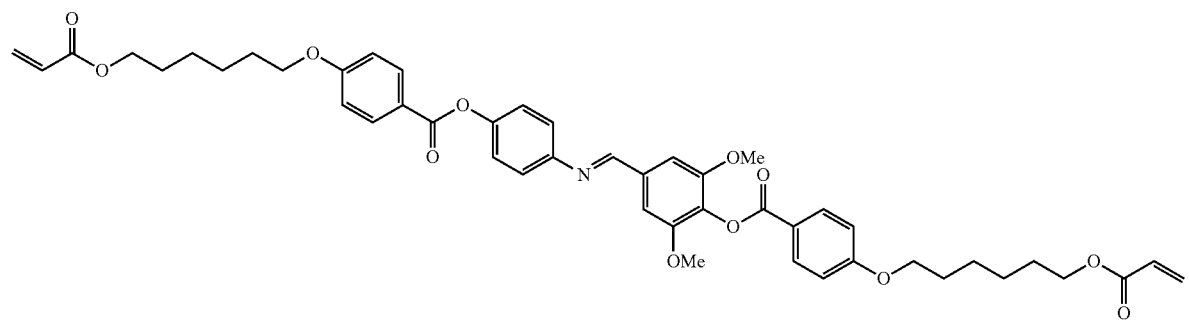
(III-5)
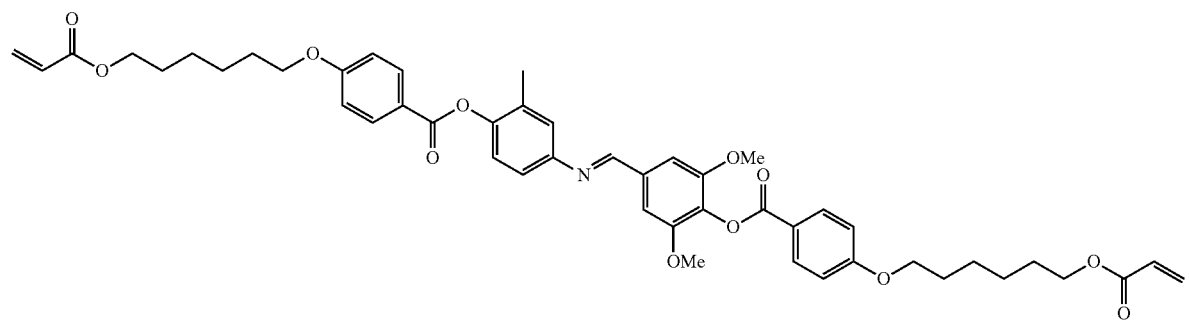
(III-6)
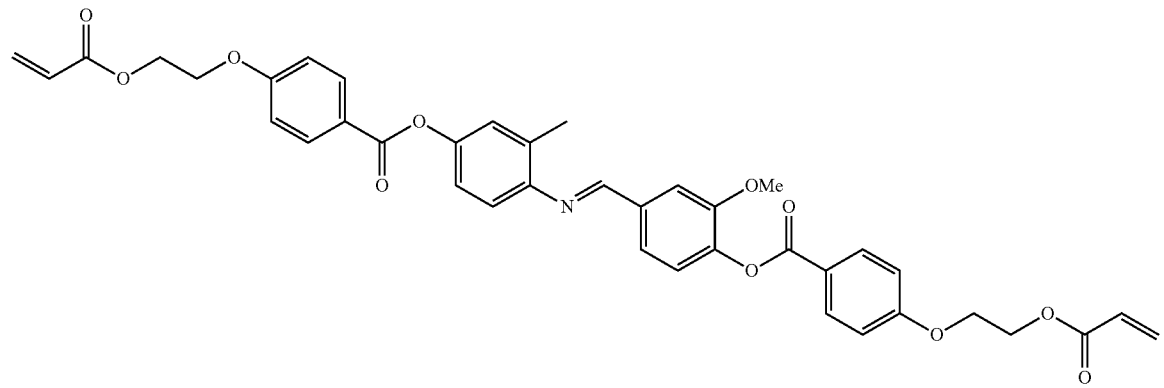

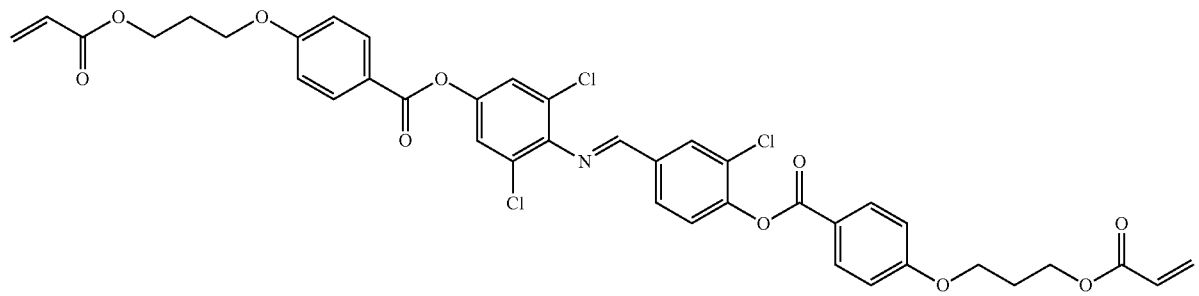
(III-7)
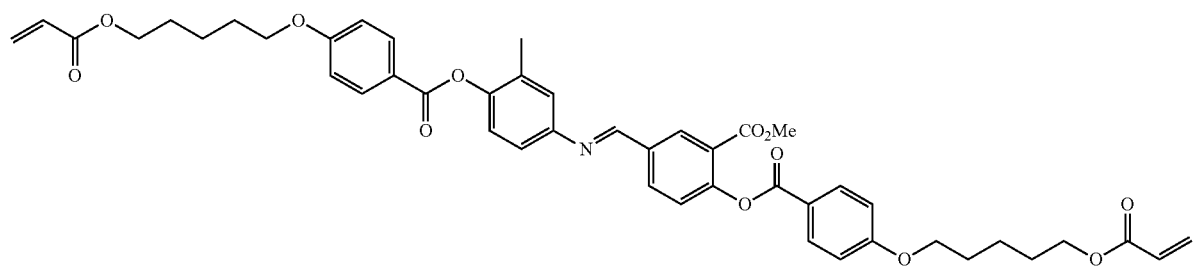
(III-8)
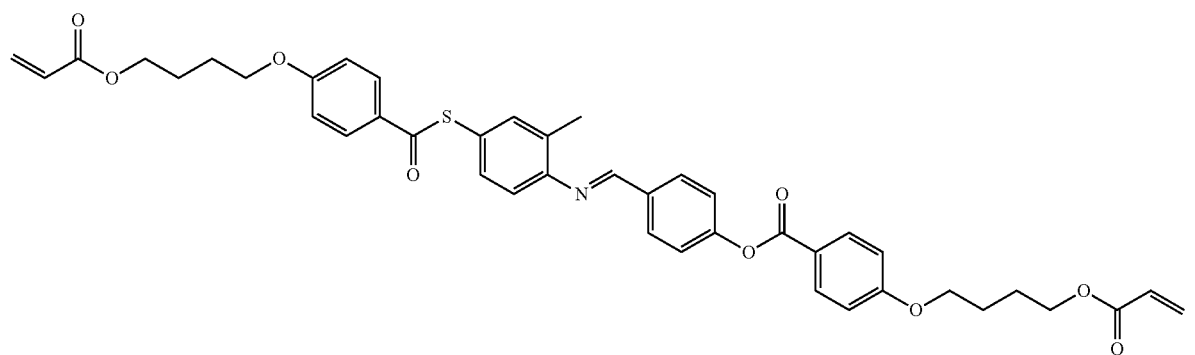
(IV-1)
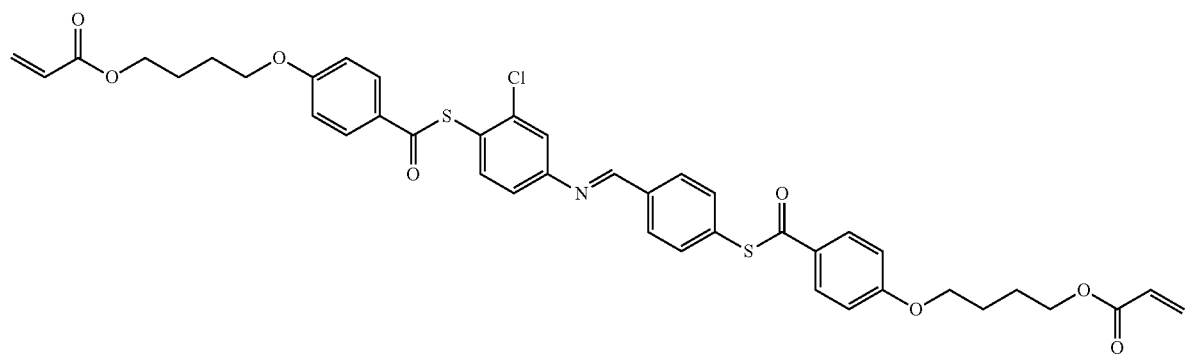
(IV-2)

-continued
(IV-3)
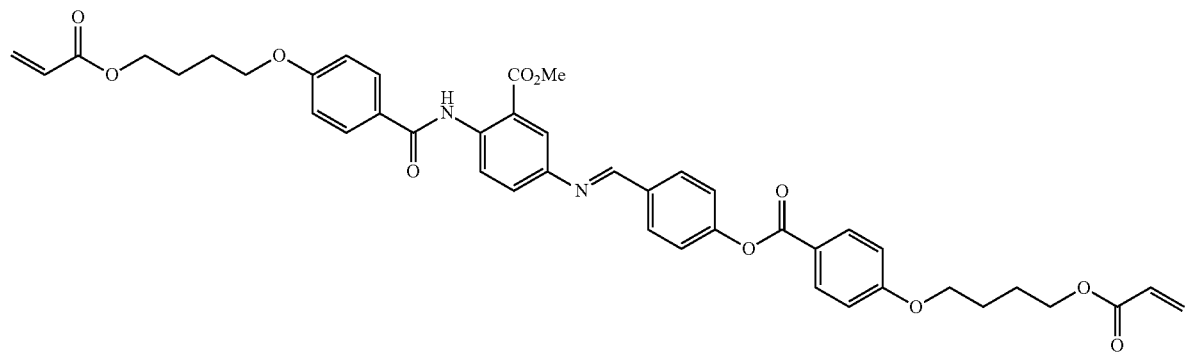
(IV-4)
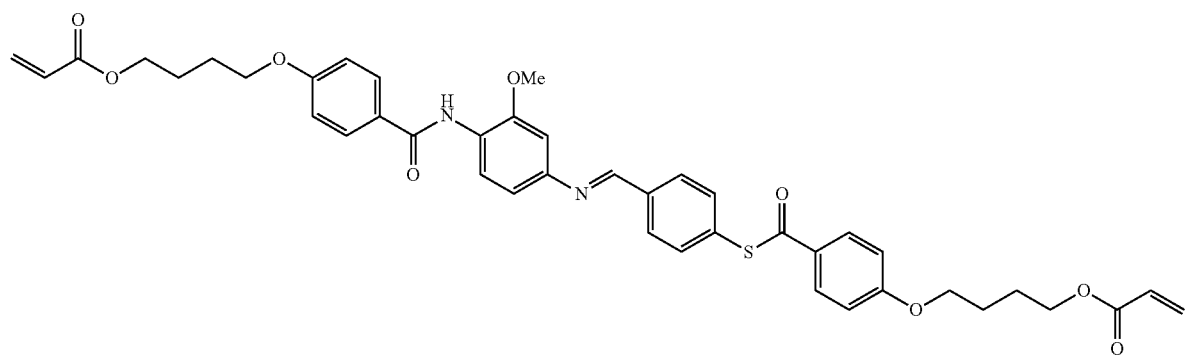
(IV-5)
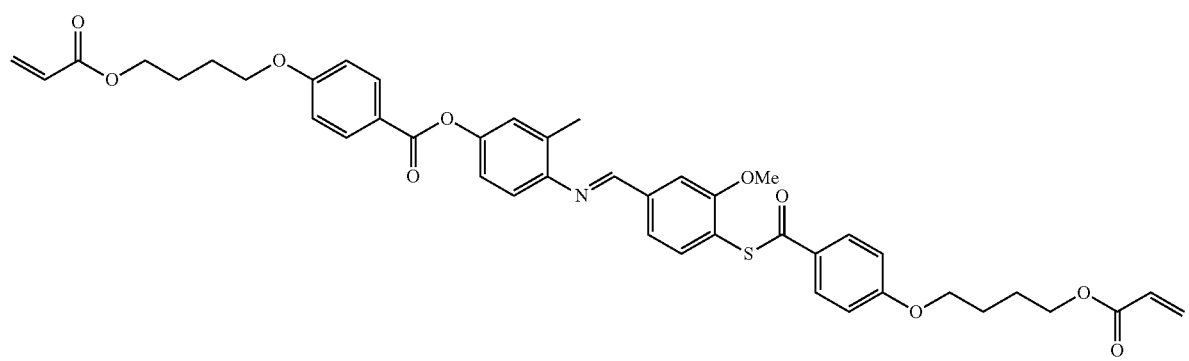
(IV-6)
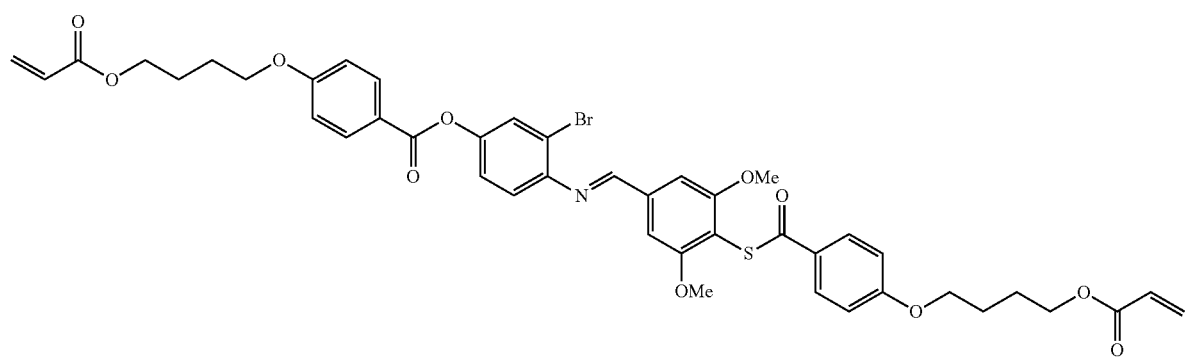

(IV-7)
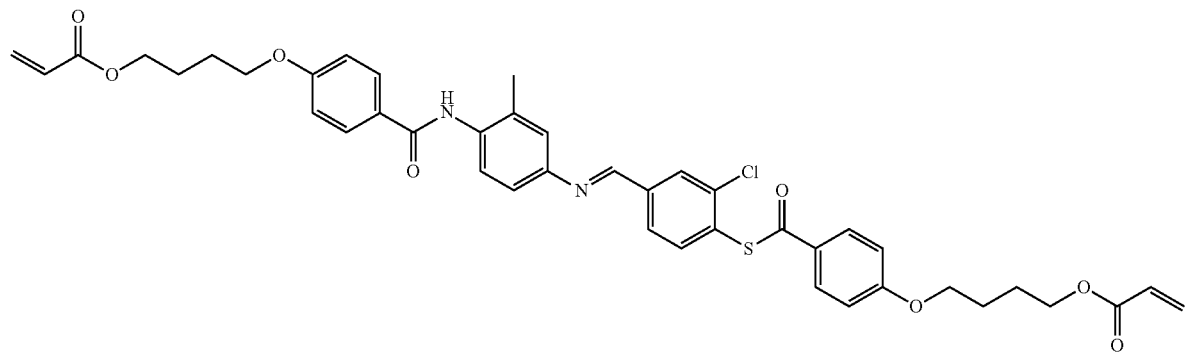
(IV-8)
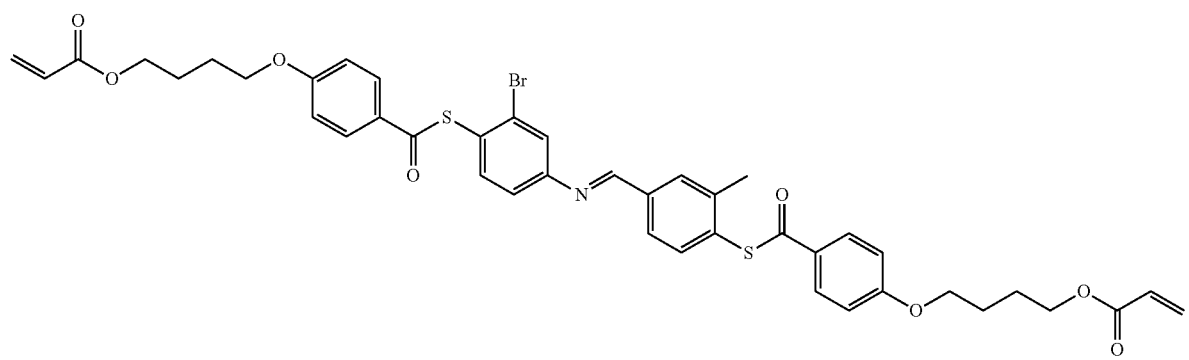
(V-1)
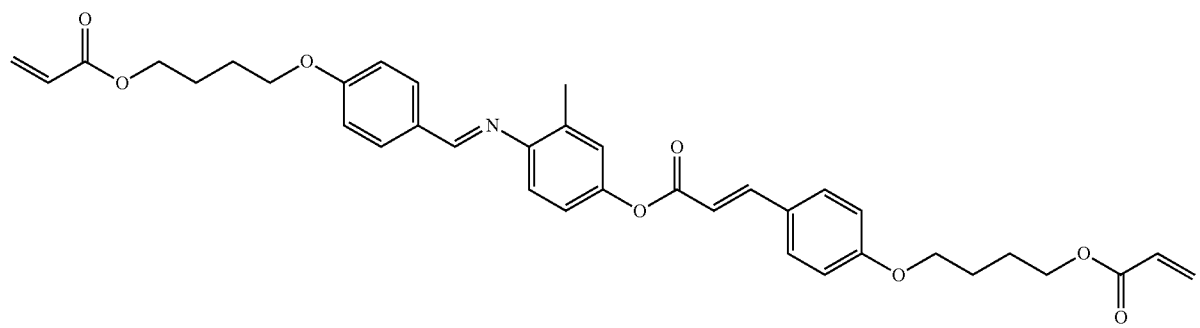
(V-2)
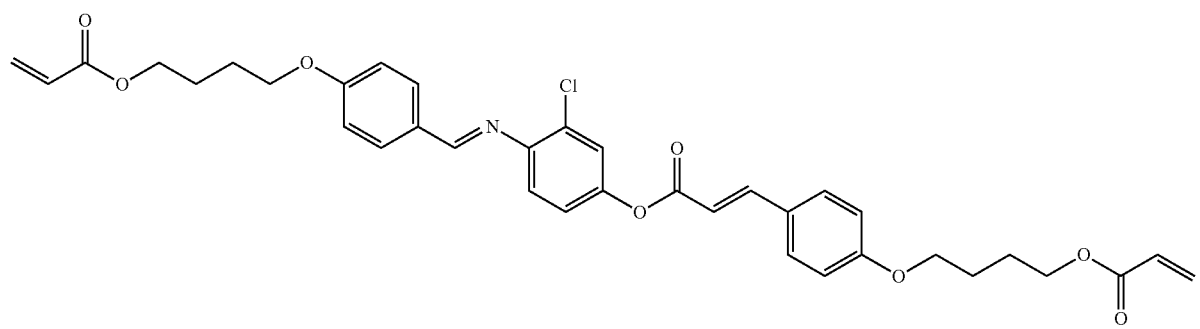

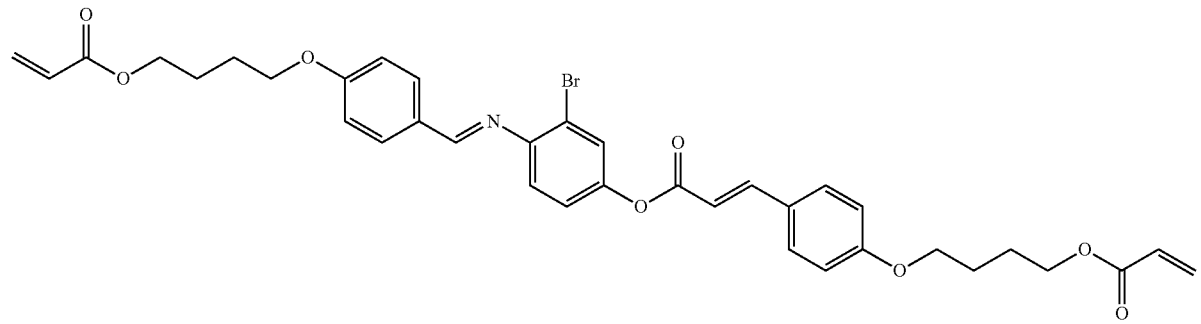
(V-3)
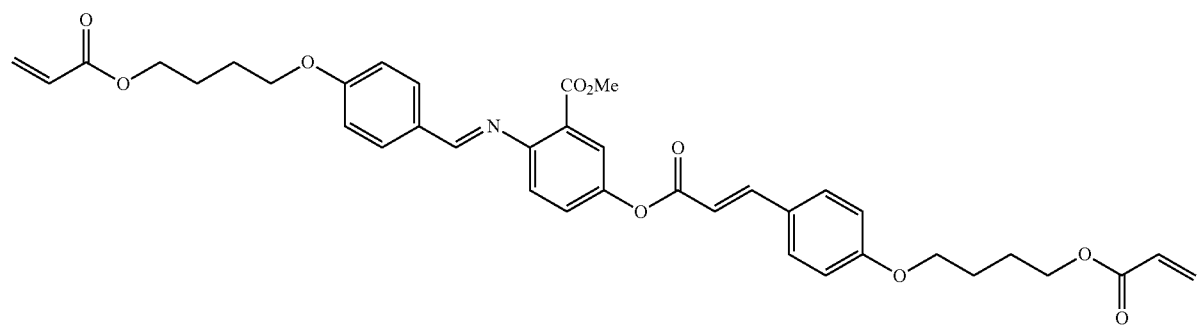
(V-4)
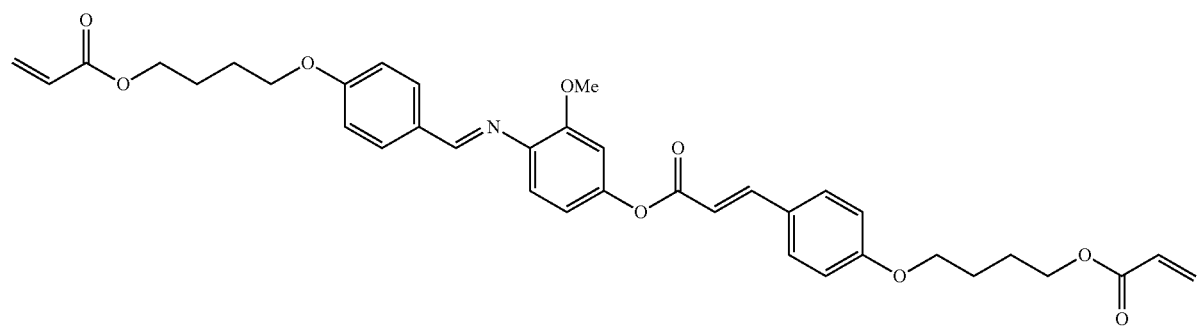
(V-5)
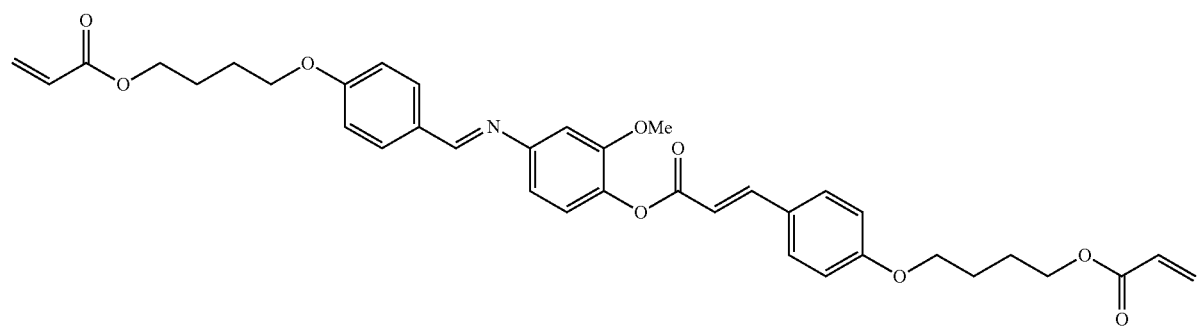
(V-6)

-continued
(V-7)
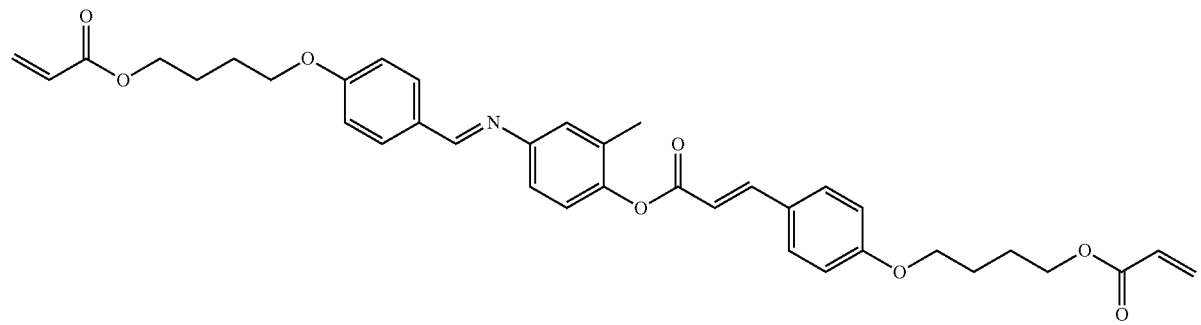
(V-8)
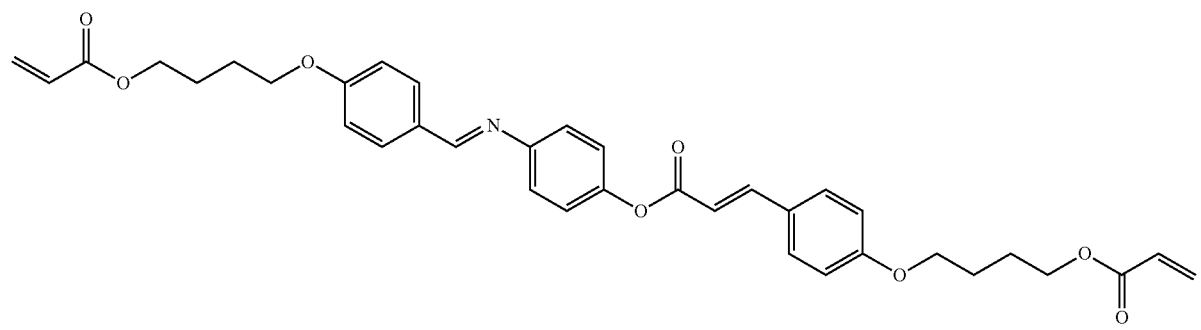
(VI-1)
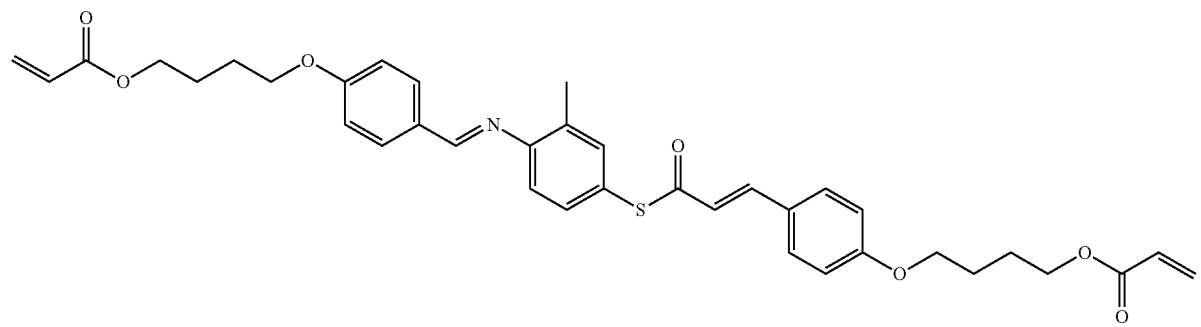
(VI-2)
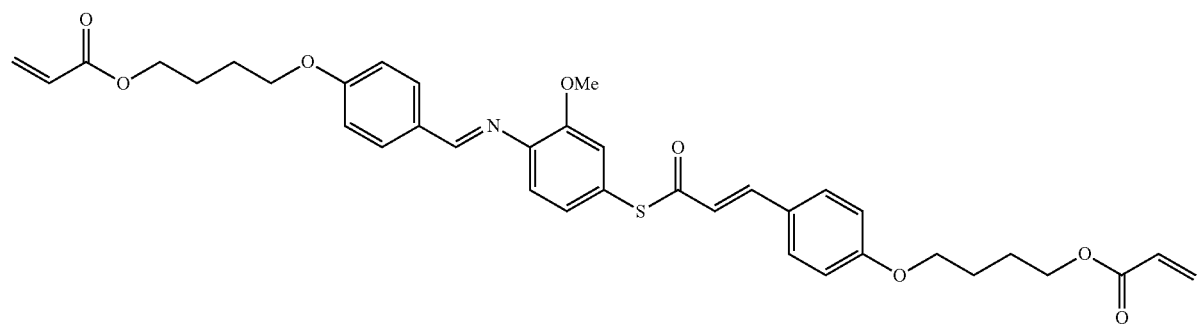

(VI-3)
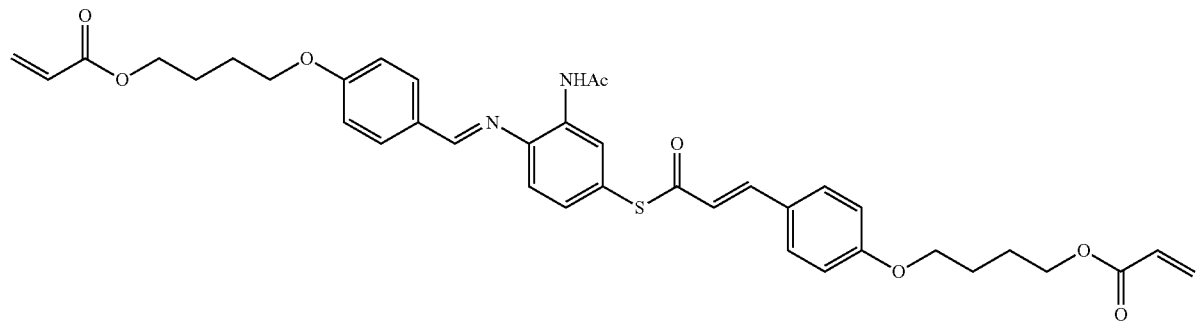
(VI-4)
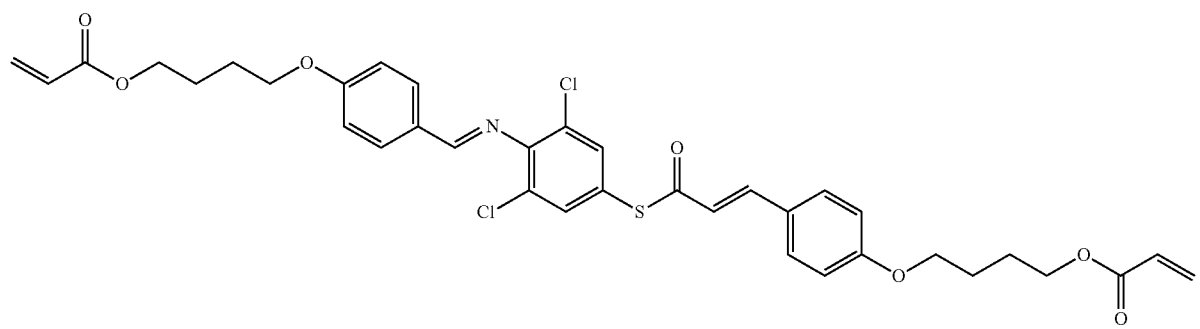
(VI-5)
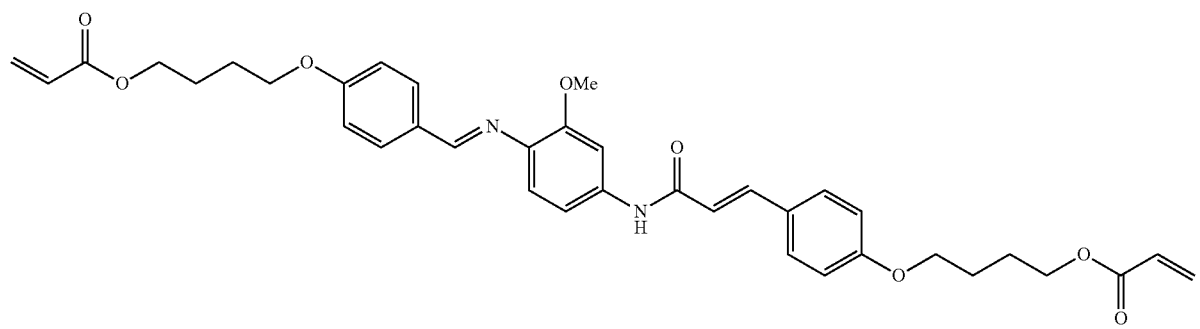
(VI-6)
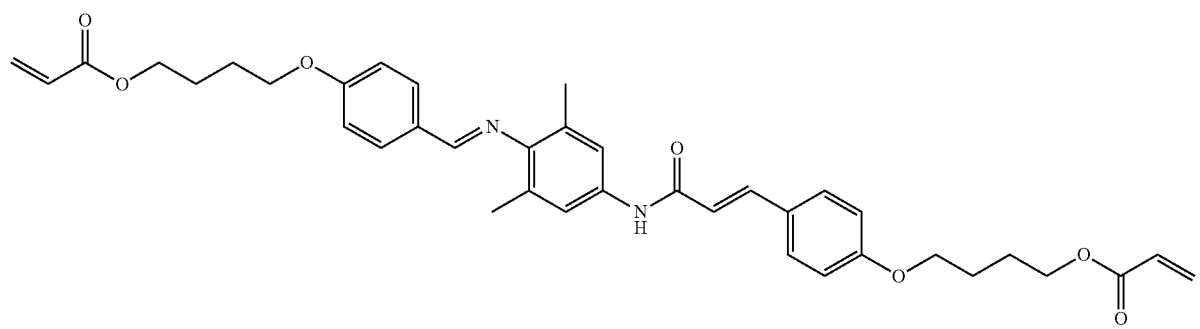

(VI-7)
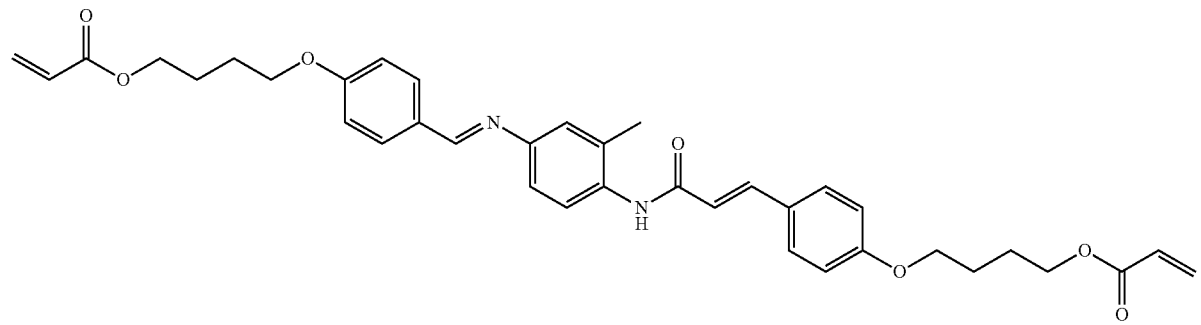
(VI-8)
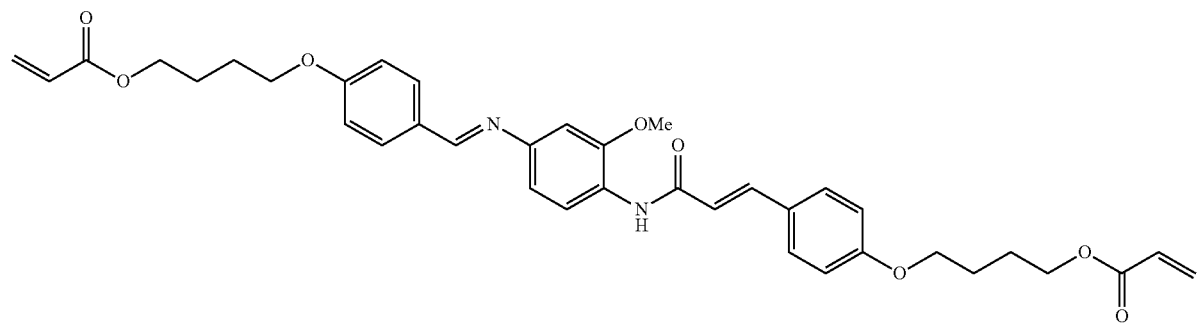
(VII-1)
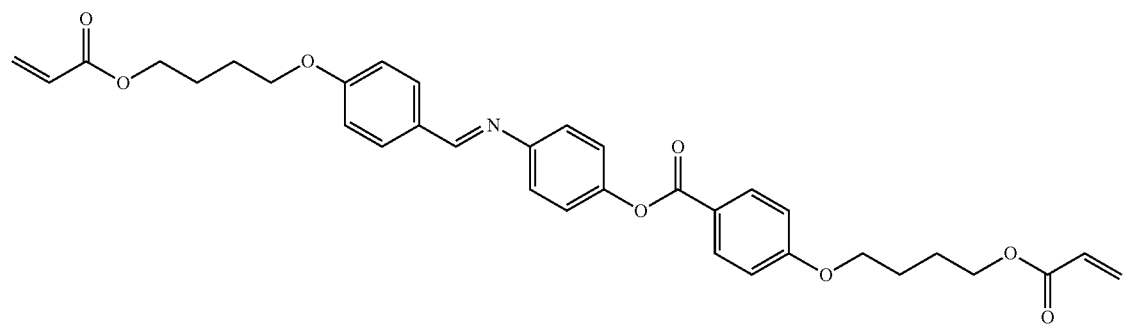
(VII-2)
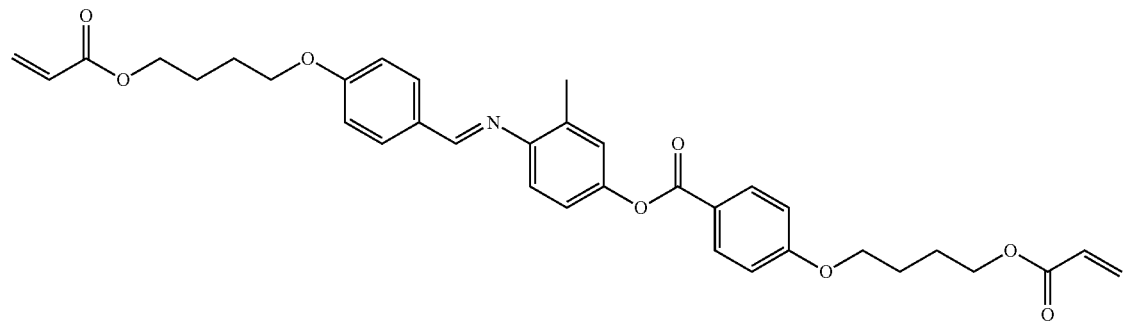

-continued
(VII-3)
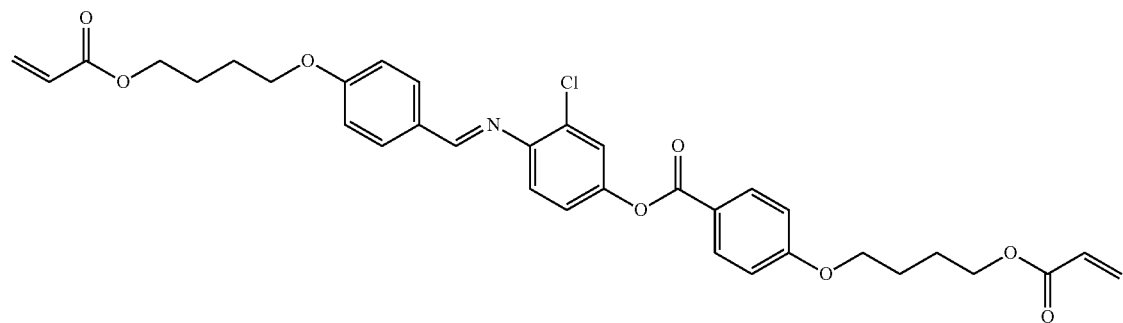
(VII-4)
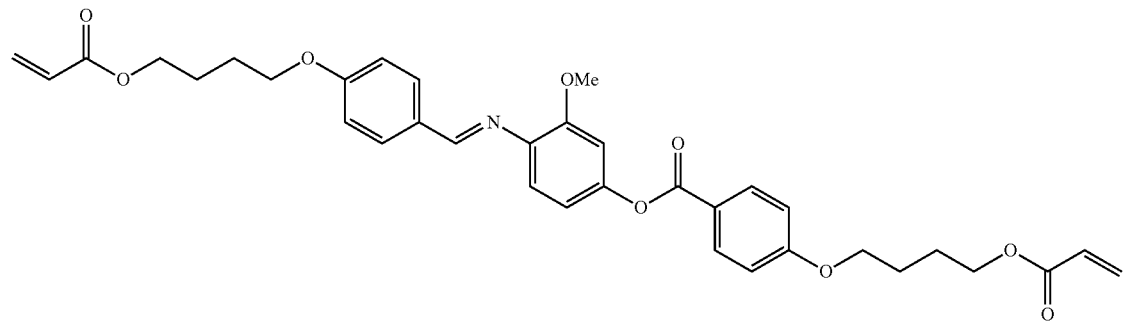
(VII-5)
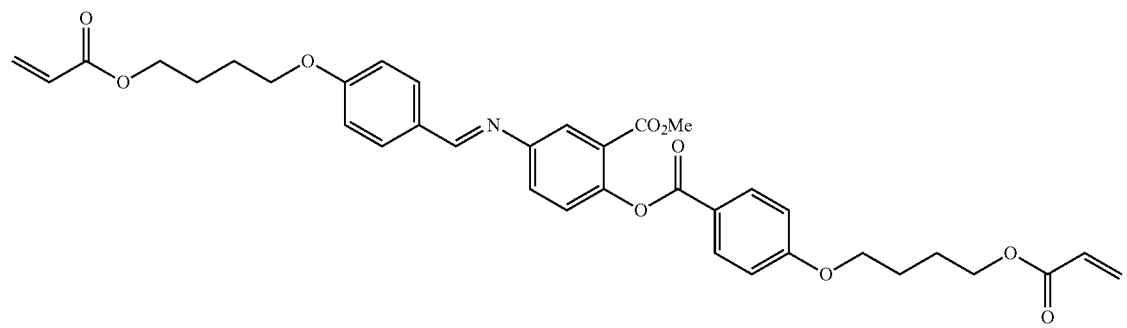
(VII-6)
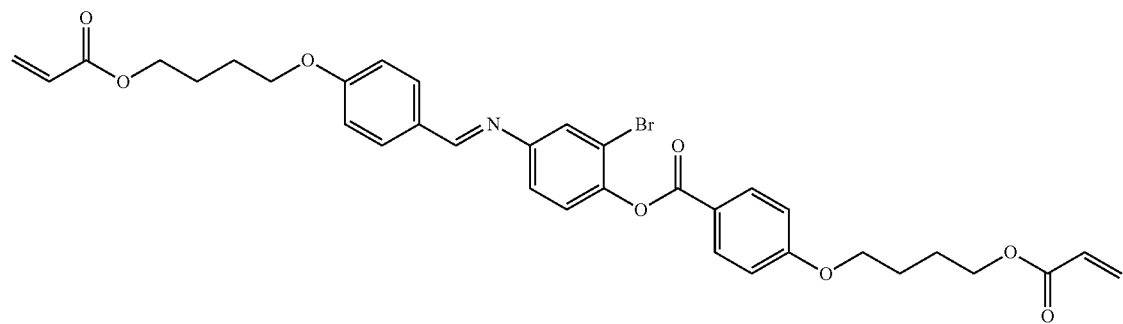
(VII-7)
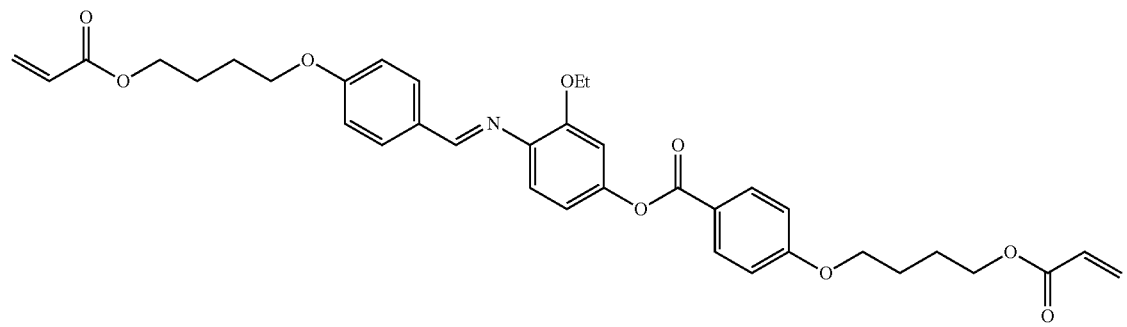

-continued
(VII-8)
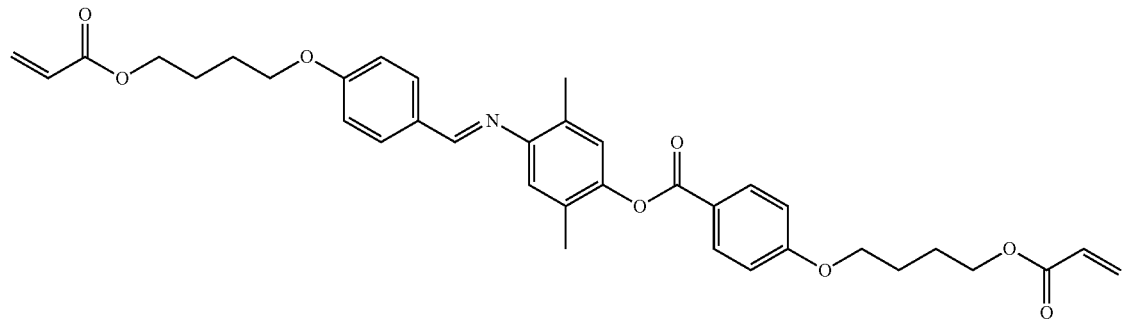
(VIII-1)
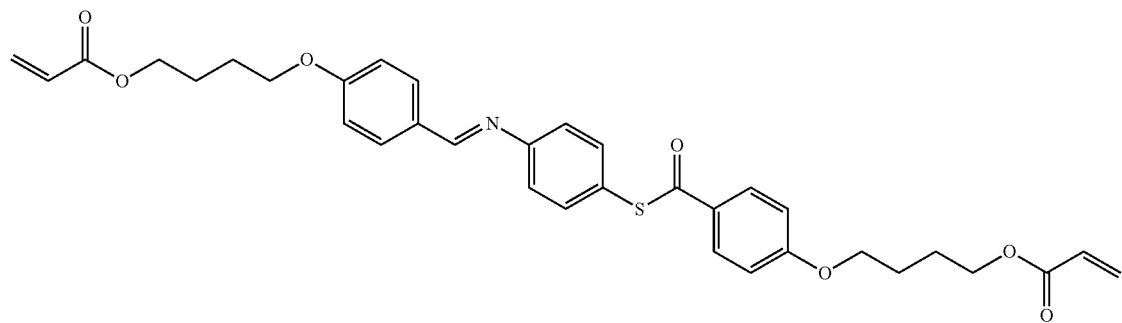
(VIII-2)
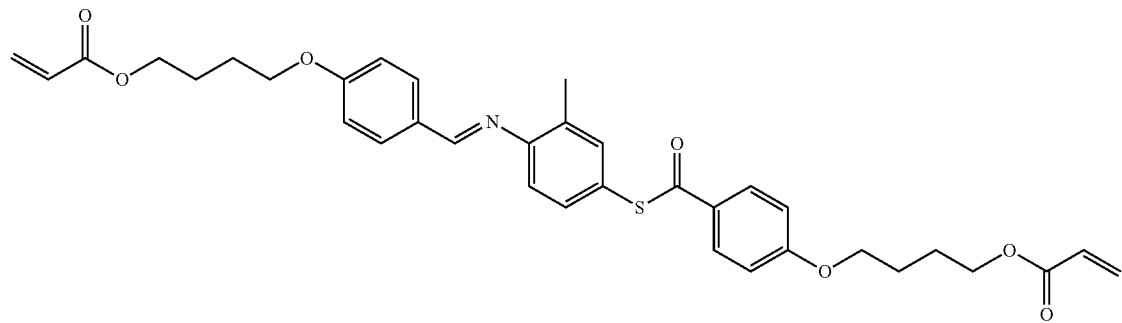
(VIII-3)
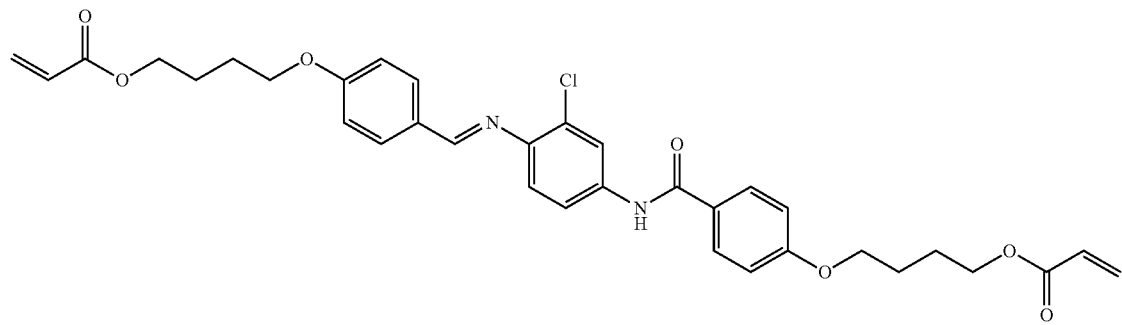
(VIII-4)
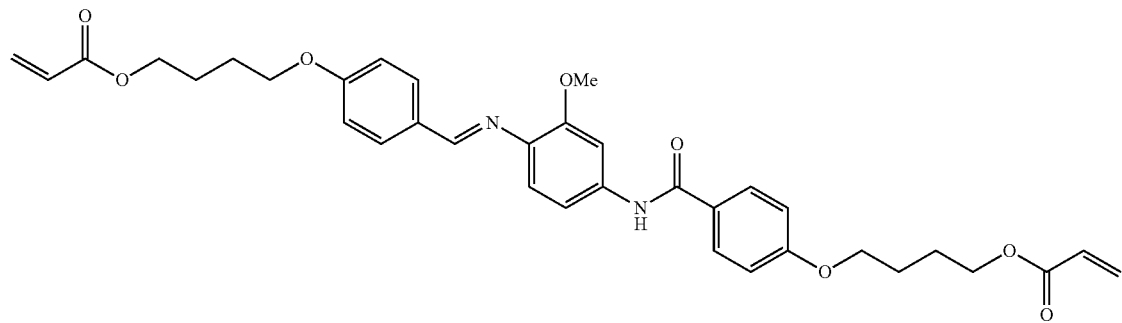

(VIII-5)
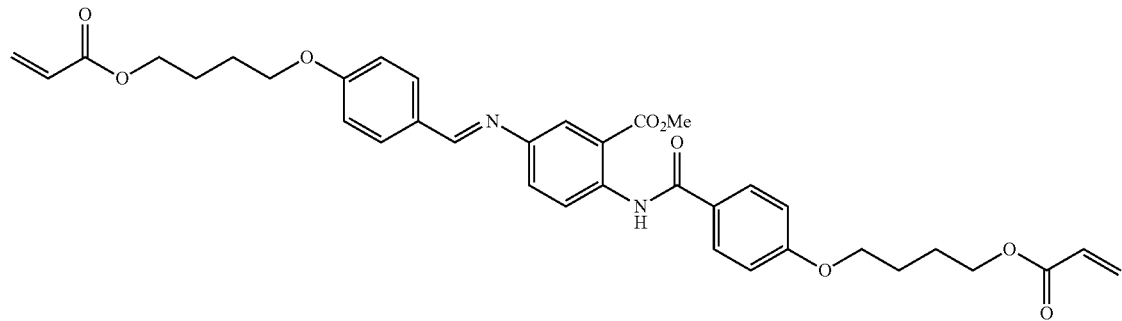
(VIII-6)
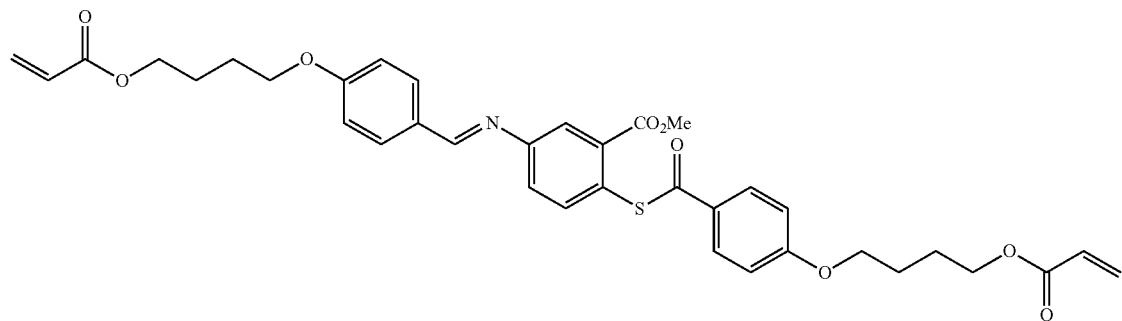
(VIII-7)
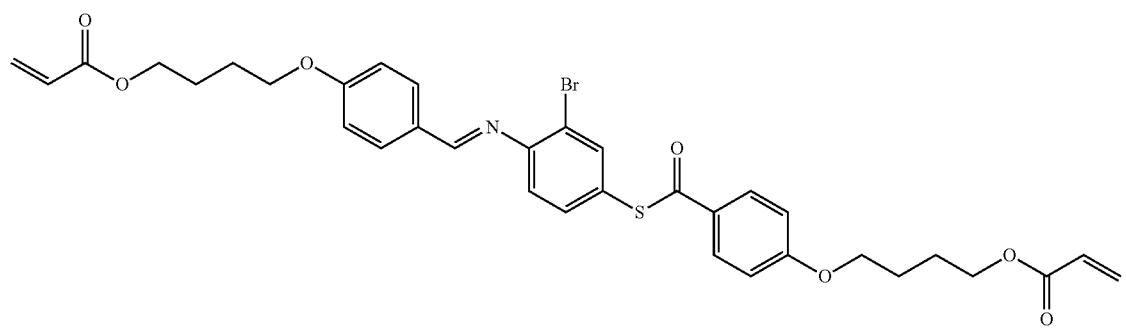
(VIII-8)
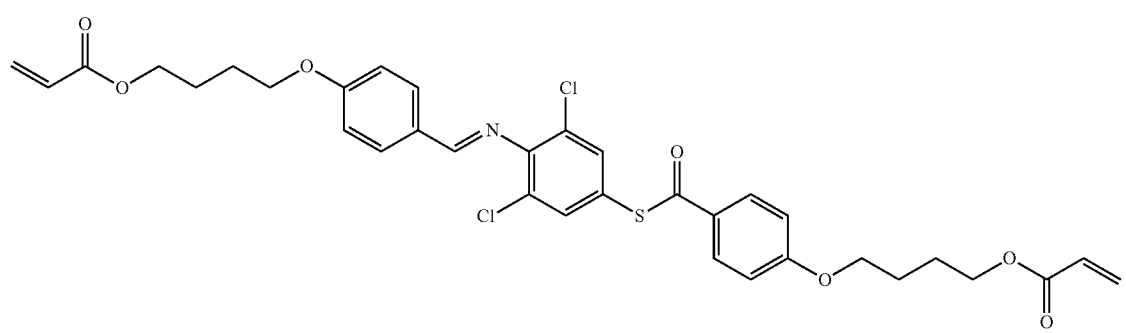
(IX-1)
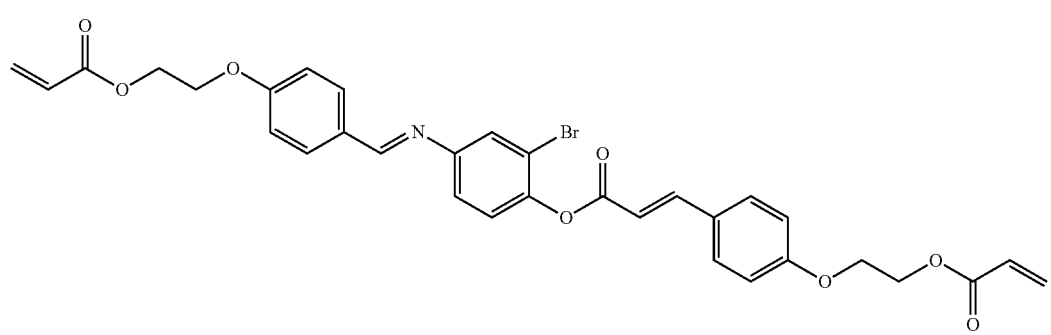

-continued
(IX-2)
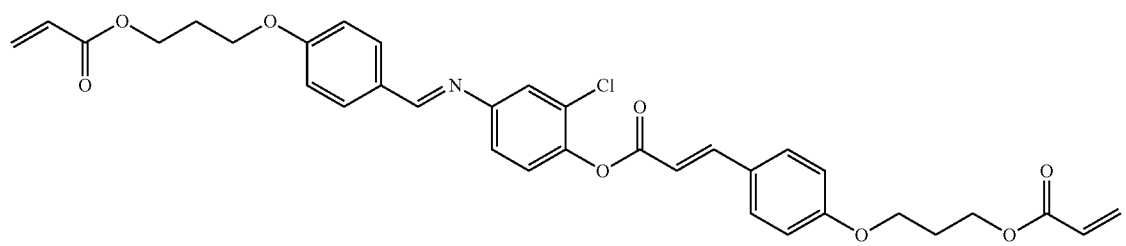
(IX-3)
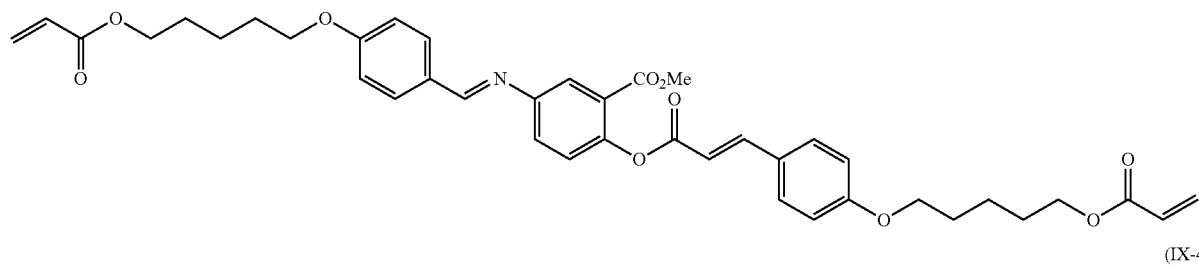
(IX-4)
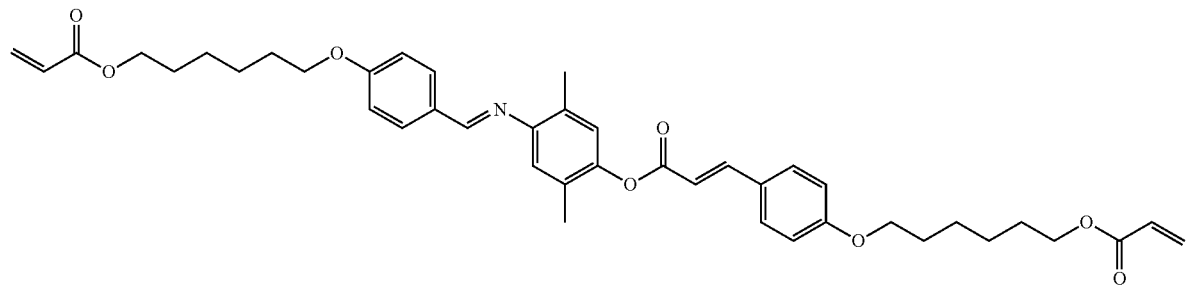
(IX-5)
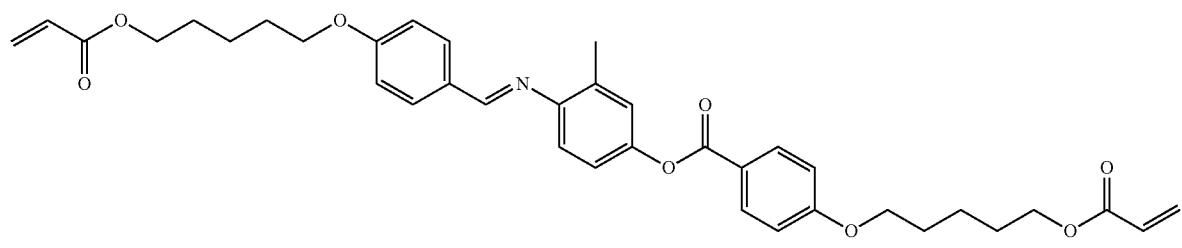
(IX-6)
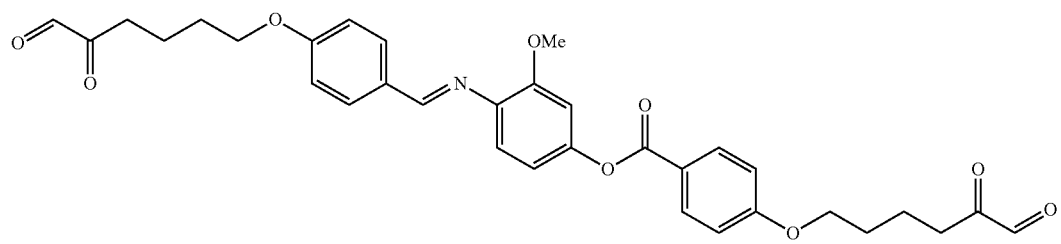
(IX-7)
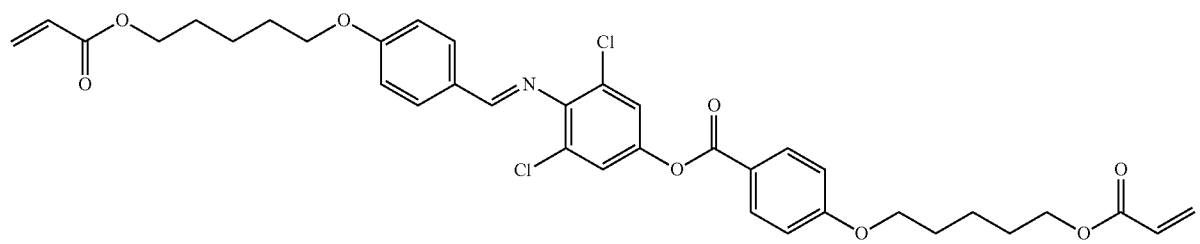

(IX-8)

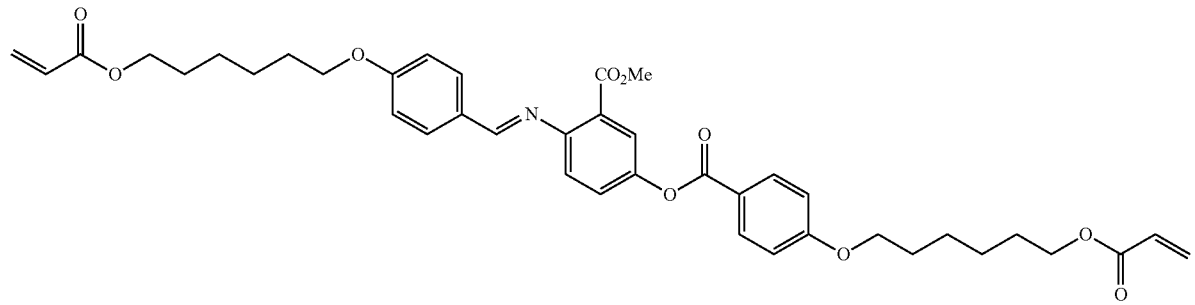

The polymerizable compound represented by the above-mentioned general formula (I) of the invention may be produced according to various methods. For example, the compound may be produced according to the method of reaction formula (1) mentioned below.

according to a known method. As an example of the compound (B), an aminophenol derivative is shown above; however, an aminothiophenol or diaminobenzene derivative that is a commercial produce or one produced according to a known method is also usable here as the compound (B). The

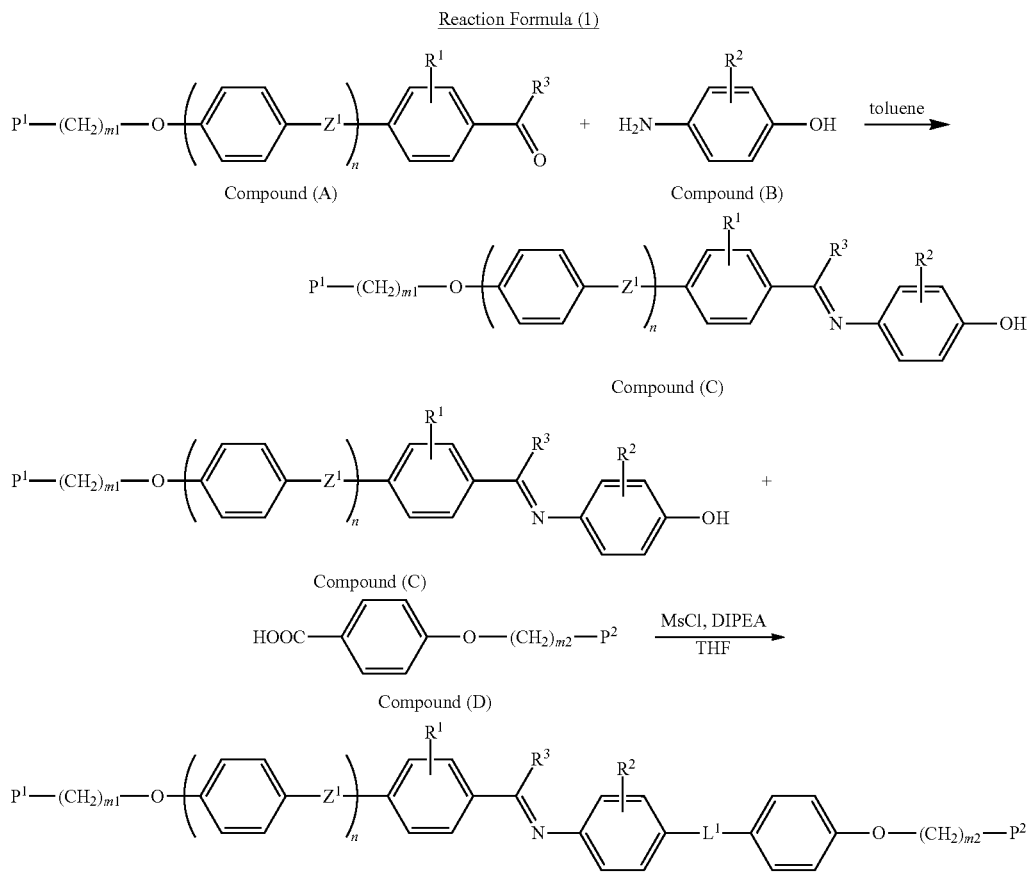

In the above-mentioned reaction formula (1), the symbols of $R^1$, $R^2$, $Z^1$, $L^1$, $R^3$, $P^1$, $P^2$ and others have the same meanings as those in the above-mentioned general formula (I), and their preferred ranges are also the same as therein.

In the reaction formula (1), the compound (A) is an aromatic aldehyde, and may be a commercial product or may be one produced according to a known method. In the reaction formula (1), the compound (B) is an aminophenol derivative, and may be a commercial product or may be one produced compound (D) may be produced according to the method described in paragraphs [0085] to [0087] on page 10 in JP-A 2002-97170.

Specifically, the polymerizable compound represented by the above-mentioned general formula (I) can be produced by preparing the compound (C) through dehydrating condensation of the compound (A) and the compound (B) followed by reaction of the compound (C) and the compound (D) according to the reaction formula (1).

For preventing thermal polymerization during the reaction, a polymerization inhibitor such as a hydroquinone derivative or the like may be added to the system.

Examples of the polymerizable compound of the invention include liquid-crystal compounds. The liquid-crystal compound has a high Δn, and the film produced by fixing the alignment of the compound is expected to attain desired optical characteristics even though it is a thin film as compared with a film produced by the use of a liquid-crystal compound having a lower Δn.

In addition, the polymerizable compound of the invention satisfies other various characteristics in that it is chemically stable, it readily dissolves in solvent and readily polymerizes, and it is colorless and transparent. The cured film produced by the use of the compound of the invention exhibits a sufficient hardness and would satisfy various characteristics in that it is colorless and transparent and its weather resistance and heat resistance are good. Accordingly, the cured film formed by the use of the compound of the invention can be utilized in various uses, for example, for retardation plates, polarizing elements, selective reflection films, color filters, antireflection films, viewing angle compensation films, holography, alignment films and others that are constituent elements of optical devices.

2. Polymerizable Composition and Film

The invention also relates to a polymerizable composition containing at least one compound of the above-mentioned formula (I), and to a film formed of the composition. The composition of the invention is useful as materials for various optical films such as retardation films, reflection films, etc.

One embodiment of the composition of the invention is a polymerizable composition containing at least one compound of the formula (I) and at least one chiral compound. The film produced by converting the composition of this embodiment into a cholesteric liquid-crystal phase followed by fixing it exhibits selective reflection characteristics against a light falling within a predetermined wavelength range in accordance with the helical pitch of the phase, and is useful as a reflection film (for example, IR-reflection film). One advantage of using the polymerizable compound that has a high Δn of the invention is that the reflection wavelength range for the film formed of the compound can be broadened as compared with the film having the same thickness but produced by the use of a liquid-crystal compound having a lower Δn.

In the composition of the invention, the compound of the formula (I) may be the main ingredient or may be an additive thereto. So far as the composition contains the compound of the general formula (I) in an amount of at least 5% by mass relative to the entire mass of the composition, the composition can enjoy the effect of the compound of the formula (I), but preferably, the content of the compound is from 10 to 85% by mass, more preferably from 10 to 75% by mass, even more preferably from 15 to 70% by mass. However, the content is not limited to the range.

(1) Chiral Compound

For preparing the composition of the invention as a composition that shows a cholesteric liquid-crystal phase, preferably, a chiral compound is added thereto. The chiral compound may be a liquid-crystalline or non-liquid-crystalline one. The chiral compound may be selected from various known chiral agents (for example, described in Liquid-Crystal Device Handbook, Chap. 3, Item 4-3, "Chiral Agents for TN, STN", p. 199, edited by Japan Society for the Promotion of Science, 142nd Committee, 1989). Chiral compounds generally contain an asymmetric carbon atom; however, axial asymmetric compounds or planar asymmetric compounds not containing an asymmetric carbon atom are also usable here. Examples of axial asymmetric compounds or planar asymmetric compounds include binaphthyl, helicene, paracyclophane and their derivatives. The chiral compound (chiral agent) for use herein may have a polymerizable group. In case where the chiral compound has a polymerizable group and the rod-shaped liquid-crystal compound to be used here along with the former also has a polymerizable group, a polymer may be formed which has a recurring unit derived from the rod-shaped liquid-crystal compound and a recurring unit derived from the chiral compound, through polymerization of the polymerizable chiral compound and the polymerizable rod-shaped liquid-crystal compound. In this embodiment, preferably, the polymerizable group that the polymerizable chiral compound has is the same type as that of the polymerizable group that the polymerizable rod-shaped liquid-crystal compound has. Accordingly, it is desirable that the polymerizable group of the chiral compound is also an unsaturated polymerizable group, an epoxy group or an aziridinyl group, more preferably an unsaturated polymerizable group, even more preferably an ethylenic unsaturated polymerizable group.

Preferably, the amount of the chiral compound to be in the composition of the invention is from 1 to 30 mol % relative to the compound of the general formula (I) in the composition. Preferably, the amount of the chiral compound to be used is smaller for favorably reducing the influence of the compound on the liquid crystallinity of the composition. Accordingly, the chiral compound is preferably a high-torsion compound in order that the compound can attain the desired helical pitch torsion orientation even though its amount is small. As the chiral agent of the type that exhibits such a strong torsion force, for example, there are mentioned the chiral agents described in JP-A 2003-287623, and these are favorably used in the invention.

(2) Other Liquid-Crystal Compound

The composition of the invention may contain one or more other liquid-crystal compounds along with the compound of the above-mentioned formula (I). The compound of the formula (I) is highly miscible with any other liquid-crystal compound, and therefore, even when any other liquid-crystal compound is mixed in the composition, it does not cause opacification and the composition still may form a film having high transparency. As capable of being mixed with any other liquid-crystal compound in the invention, there can be provided various types of compositions applicable to various uses. Examples of the other liquid-crystal compounds usable here include rod-shaped nematic liquid-crystal compounds. Examples of rod-shaped nematic liquid-crystal compounds include azomethines, azoxy compounds, cyanobiphenyls, cyanophenyl esters, benzoates, phenyl cyclohexanecarboxylates, cyanophenylcyclohexanes, cyano-substituted phenylpyrimidines, alkoxy-substituted phenylpyrimidines, phenyldioxanes, tolans and alkenylcyclohexylbenzonitriles, Not only low-molecular liquid-crystal compounds but also high-molecular liquid-crystal compounds can be used here.

The other liquid-crystal compounds usable in the invention may be polymerizable ones or non-polymerizable ones. Rod-shaped liquid-crystal compounds not having a polymerizable compound are described in many publications (for example, Y. Goto et. al., Mol. Cryst. Liq. Cryst. 1995, Vol. 260, pp. 23-28).

Polymerizable rod-shaped liquid-crystal compounds may be obtained by introducing a polymerizable group into rod-shaped liquid-crystal compounds. Examples of the polymerizable group include an unsaturated polymerizable group, an epoxy group and an aziridinyl group. Preferred is an unsaturated polymerizable group, and more preferred is an ethylenic unsaturated polymerizable group. The polymerizable group may be introduced into the molecule of a rod-shaped liquid-crystal compound according to various methods. The number of the polymerizable groups which the polymerizable rod-shaped liquid-crystal compound has is preferably from 1 to 6, more preferably from 1 to 3. Examples of the polymerizable rod-shaped liquid-crystal compound include the compounds described in Makromol. Chem., Vol. 190, p. 2255 (1989); Advanced Materials, Vol. 5, p. 107 (1993); U.S. Pat. Nos. 4,683,327, 5,622,648, 5,770,107; WO95/22586, WO95/24455, WO97/00600, WO98/23580, WO98/52905; JP-A 1-272551, 6-16616, 7-110469, 11-80081, 2001-328973, etc. Two or more different types of polymerizable rod-shaped liquid-crystal compounds may be used here as combined. Using two or more different types of polymerizable rod-shaped liquid-crystal compounds as combined lowers the orientation temperature thereof.

The amount of the other liquid-crystal compound to be added is not specifically defined. The content of the compound of the above-mentioned formula (I) in the composition may be high, or the content of the other liquid-crystal compound therein may be high, or the two may be the same. Anyhow, the content of the compound may be controlled to fall within a preferred range depending on the use of the composition.

(3) Polymerization Initiator

Preferably, the composition of the invention contains a polymerization initiator. For example, in an embodiment where curing reaction is attained through UV irradiation to form a cured film, the polymerization initiator to be used is preferably a photopolymerization initiator having the ability to initiate polymerization through UV irradiation. Examples of the photopolymerization initiator include α-carbonyl compounds (described in U.S. Pat. Nos. 2,367,661, 2,367,670), acyloin ethers (described in U.S. Pat. No. 2,448,828), α-hydrocarbon-substituted aromatic acyloin compounds (described in U.S. Pat. No. 2,722,512), polynuclear quinone compounds (described in U.S. Pat. Nos. 3,046,127, 2,951,758), combination of triarylimidazole dimer and p-aminophenyl ketone (described in U.S. Pat. No. 3,549,367), acridine compounds and phenazine compounds (described in JP-A 60-105667 and U.S. Pat. No. 4,239,850), and oxadiazole compounds (described in U.S. Pat. No. 4,212,970), etc.

The amount of the photopolymerization initiator to be used is preferably from 0.1 to 20% by mass of the composition (or the solid content thereof when the composition is a coating liquid), more preferably from 1 to 8% by mass.

(4) Alignment Controlling Agent

An alignment controlling agent capable of contributing toward stable or rapid conversion into liquid-crystal phase (for example, cholesteric liquid-crystal phase) may be added to the composition of the invention. Examples of the alignment controlling agent include fluorine-containing (meth) acrylate polymers, and compounds represented by the following general formulae (X1) to (X3). Two or more selected from these may be added to the composition. The compounds reduce the tilt angle of the molecules of a liquid-crystal compound in the layer-to-air interface, or enable substantial horizontal alignment of the molecules therein. In this description, "horizontal alignment" means that the long axis of the liquid-crystal molecule is parallel to the film plane, but this does not require a severe parallel state; and in this description, this means an alignment state of such that the tile angle to the horizontal plane is less than 20 degrees. In case where a liquid-crystal compound is horizontally aligned in the vicinity of the air interface, alignment defects hardly occur, and therefore the transparency of the formed film in the visible light region could be high. On the other hand, when the molecules of a liquid-crystal compound are aligned at a large tilt angle, and for example, when the compound is converted to show a cholesteric liquid-crystal phase, then the helical axis thereof may be shifted from the normal line relative to the film plane, therefore causing some disadvantages in that the reflectivity of the film may lower and the finger print pattern may occur thereby bringing about haze increase and diffractivity expression.

Examples of the fluorine-containing (meth)acrylate polymer usable as the alignment controlling agent are described in JP-A 2007-272185, [0018] to [0043].

The following general formulae (X1) to (X3) usable as the alignment controlling agent here are described in order.

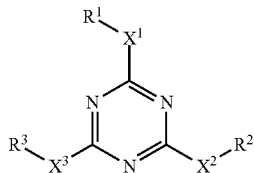

(X1)

In the formula, $R^1$, $R^2$ and $R^3$ each independently represent a hydrogen atom or a substituent; $X^1$, $X^2$ and $X^3$ each represent a single bond or a divalent linking group. Preferred examples of the substituent represented by $R^1$ to $R^3$ include a substituted or unsubstituted, alkyl group (above all, more preferred is an unsubstituted alkyl group or a fluorine-substituted alkyl group) or aryl group (above all, more preferred is an aryl group having a fluorine-substituted alkyl group), a substituted or unsubstituted amino group, an alkoxy group, an alkylthio group, and a halogen atom. The divalent linking group represented by $X^1$, $X^2$ and $X^3$ is preferably a divalent linking group selected from an alkylene group, an alkenylene group, a divalent aromatic group, a divalent heterocyclic residue, —CO—, —NRa— (Ra represents an alkyl group having from 1 to 5 carbon atoms, or a hydrogen atom), —O—, —S—, —SO—, —SO$_2$— or their combinations. The divalent linking group is more preferably a divalent linking group selected from groups of an alkylene group, a phenylene group, —CO—, —NRa—, —O—, —S— and —SO$_2$—, or a divalent group comprising a combination of at least two groups selected from those groups. The number of the carbon atoms constituting the alkylene group is preferably from 1 to 12. The number of the carbon atoms constituting the alkenylene group is preferably from 2 to 12. The number of the carbon atoms constituting the divalent aromatic group is preferably from 6 to 10.

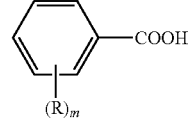

(X2)

In the formula, R represents a substituent; and m indicates an integer of from 0 to 5. When m is an integer of 2 or more, plural R's may be the same or different. Preferred examples of the substituent of Rare the same as those mentioned hereinabove as preferred examples of the substituent of $R^1$, $R^2$ and $R^3$. m is preferably an integer of from 1 to 3, more preferably 2 or 3.

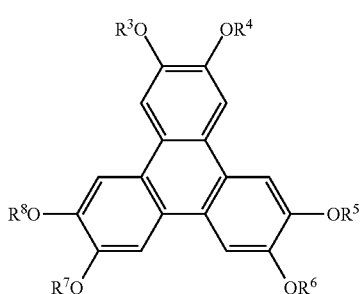

(X 3)

In the formula, $R^4$, $R^5$, $R^6$, $R^7$, $R^8$ and $R^9$ each independently represent a hydrogen atom or a substituent. Preferred examples of the substituent represented by $R^4$, $R^5$, $R^6$, $R^7$, $R^8$ and $R^9$ are the same as those mentioned hereinabove as the substituent represented by $R^1$, $R^2$ and $R^3$ in the general formula (XI).

Examples of the compounds represented by the above-mentioned formulae (X1) to (X3), which are usable as the alignment controlling agent in the invention, include the compounds described in JP-A 2005-99248.

In the invention, one alone or two or more of the compounds represented by the general formulae (X1) to (X3) may be used as the alignment controlling agent, either singly or as combined.

The amount of the compound represented by any of the general formulae (X1) to (X3) in the composition is preferably from 0.01 to 10% by mass of the mass of the compound of the above-mentioned formula (I), more preferably from 0.01 to 5% by mass, even more preferably from 0.02 to 1% by mass.

(5) Other Additive

The composition of the invention may contain one or more other additives of, for example, antioxidant, UV absorbent, sensitizer, stabilizer, plasticizer, chain transfer agent, polymerization inhibitor, defoaming agent, leveling agent, thickener, flame retardant, surfactant, dispersing agent, colorant such as dye, pigment, etc.

(6) Preparation Method of Film Using Composition

The composition of the invention is useful as a material for various optical films such as retardation films, reflection films, etc. One example of the production method for the film at least includes:

(i) applying the polymerizable composition of the invention onto the surface of a substrate or the like to make the composition in a state of a liquid-crystal phase (cholesteric liquid-crystal phase, etc.), and (ii) curing the polymerizable composition to thereby fix the liquid-crystal phase to form a cured film.

The steps (i) and (ii) may be repeated multiple times to produce a film in which a plurality of the above-mentioned cured films are laminated.

In the step (i), first, the polymerizable composition of the invention is applied onto a substrate or onto the surface of an alignment film formed on a substrate. Preferably, the composition is prepared as a coating liquid in which the material is dissolved and/or dispersed in a solvent. The solvent to be used in preparing the coating liquid is preferably an organic solvent. The organic solvent includes amides (e.g., N,N-dimethylformamide); sulfoxides (e.g., dimethyl sulfoxide); heterocyclic compounds (e.g., pyridine); hydrocarbons (e.g., benzene, hexane); alkyl halides (e.g., chloroform, dichloromethane); esters (e.g., methyl acetate, butyl acetate); ketones (e.g., acetone, methyl ethyl ketone); ethers (e.g., tetrahydrofuran, 1,2-dimethoxyethane); 1,4-butanediol diacetate, etc. Of those, especially preferred are alkyl halides and ketones. Two or more different types of organic solvents may be used here as combined.

Coating with the coating liquid may be attained according to various methods such as a wire bar coating method, an extrusion coating method, a direct gravure coating method, a reverse gravure coating method, a die coating method, etc. Using an inkjet apparatus, the composition may be jetted out through the nozzle thereof to form a coating film.

Next, the composition applied onto the surface to form a coating film thereon is converted into a liquid-crystal phase such as a cholesteric liquid-crystal phase, etc. In an embodiment where the composition is prepared as a coating liquid that contains a solvent, the coating film may be dried to remove the solvent, whereby the film may be in a state of liquid-crystal phase. For making the coating film kept at a transition temperature to be a liquid-crystal phase, if desired, the coating film may be heated. For example, the coating film may be once heated up to a temperature of the anisotropic phase thereof, and then it may be cooled to the liquid-crystal phase transition temperature thereof, whereby the coating film can be stably in a state of liquid-crystal phase. The liquid-crystal phase transition temperature of the composition is preferably within a range of from 10 to 250° C. from the viewpoint of the production aptitude and the like thereof, more preferably from 10 to 150° C. When the temperature is lower than 10° C., then the production method would require a cooling step or the like for cooling the coating film to a temperature falling within the range within which the coating film could exhibit a liquid-crystal phase. On the other hand, when the transition temperature is higher than 200° C., then the production method would require a high temperature in order that the coating film could be once in an isotropic liquid state at a further higher temperature than in the temperature range within which the film could exhibit a liquid-crystal phase; however, this is disadvantageous in point of waste of thermal energy, substrate deformation, degradation, etc.

Next, in the step (ii), the coating film in the state of a liquid-crystal phase is cured. For curing, any polymerization method is employable, including a radical polymerization method, an anionic polymerization method, a cationic polymerization method, a coordination polymerization method, etc. A suitable polymerization method will be selected in accordance with the compound of the formula (I). The polymerization gives a polymer that has a unit derived from the compound of the formula (I) in the constitutive units therein.

In one example, the curing reaction is attained through UV irradiation. For UV irradiation, usable is a light source of a UV lamp, etc. In this step, UV irradiation promotes curing of the composition to fix the cholesteric liquid-crystal phase, and a cured film is thereby formed.

The UV irradiation energy dose is not specifically defined, but is, in general, preferably from 100 mJ/cm$^2$ to 800 mJ/cm$^2$ or so. The time for UV irradiation for the coating film is not specifically defined, and the time will be determined from the viewpoint of both sufficient strength and productivity of the cured film.

For promoting the curing reaction, the UV irradiation may be attained under heat. The temperature in UV irradiation is preferably within a temperature range within which the coating film could exhibit a liquid-crystal phase in order that the liquid-crystal phase of the film could be prevented from being disordered. The oxygen concentration in the atmosphere during the process may participate in the degree of polymerization, and therefore, in case where the desired degree of polymerization could not be attained in air and the film strength is insufficient, it is desirable that the oxygen concentration in the atmosphere is lowered according to a nitrogen purging method or the like.

In the above-mentioned step, the liquid-crystal phase is fixed to form a cured film. Regarding the "fixed" state of liquid-crystal phase in this, the most typical and preferred embodiment of the state is such that the alignment of the compound in a liquid-crystal phase is maintained as such. However, the invention is not limited to the case. Concretely, the fixed state means that, in a temperature range of from 0° C. to 50° C. in an ordinary condition, or in a temperature range of from −30° C. to 70° C. in a severe condition, the layer has no flowability and the alignment morphology in the layer is not changed by any external field or external force applied thereto, and in that condition, the layer can continue to stably keep the fixed alignment morphology therein. In the invention, owing to the curing reaction to be promoted through UV irradiation, the alignment state of the liquid-crystal phase is fixed in the cured film.

In the invention, it is enough that the optical properties of the liquid-crystal phase are kept in the layer, and finally it is unnecessary that the composition in the cured film would exhibit liquid crystallinity. For example, the composition may lose liquid crystallinity through the curing reaction for polymerization.

The thickness of the cured film is not specifically defined. Depending on the use thereof or in accordance with the desired optical characteristics thereof, the preferred thickness of the film will be determined. In general, the thickness is preferably from 0.05 to 50 µm, more preferably from 1 to 35 µm.

(7) Substrate

The film of the invention may have a substrate. The substrate may be any self-supporting one capable of supporting the above-mentioned cured film, and is not specifically defined in point of the material and the optical characteristics thereof. The substrate may be selected from glass plates, quartz plates, polymer films, etc. Depending on the use thereof, the substrate may be required to have high transparency to UV light. As the polymer film having high transparency to visible light, there are mentioned various types of polymer films for optical films to be used as constituent parts of display devices such as liquid-crystal display devices, etc. The substrate includes, for example, polyester films of polyethylene terephthalate (PET), polybutylene terephthalate, polyethylene naphthalate (PEN), etc.; polycarbonate (PC) films, polymethyl methacrylate films; polyolefin films of polyethylene, polypropylene, etc.; polyimide films, triacetyl cellulose (TAC) films, etc. Preferred are polyethylene terephthalate and triacetyl cellulose.

(8) Alignment Layer

The film of the invention may have an alignment layer between the substrate and the above-mentioned cured film. The alignment layer has the function of more accurately defining the alignment direction of the liquid-crystal compound in the cured film. The alignment layer may be provided by means of rubbing treatment of an organic compound (preferably a polymer), oblique vapor deposition of an inorganic compound, formation of a layer having microgrooves, etc. Further known is an alignment layer capable of exhibiting the alignment function through electric field impartation, magnetic field impartation or photoirradiation. Preferably, the alignment layer is formed through rubbing treatment of the surface of a polymer film.

Preferably, the material of the alignment layer is a polymer of an organic compound, for which a self-crosslinkable polymer or a polymer crosslinkable by a crosslinking agent is well used. Naturally, a polymer having the two functions is also usable. Examples of the polymer include polymethyl methacrylate, acrylic acid/methacrylic acid copolymer, styrene/maleinimide copolymer, polyvinyl alcohol and modified polyvinyl alcohol, poly(N-methylolacrylamide), styrene/vinyltoluene copolymer, chlorosulfonated polyethylene, nitrocellulose, polyvinyl chloride, polyolefin chloride, polyester, polyimide, vinyl acetate/vinyl chloride copolymer, ethylene/vinyl acetate copolymer, carboxymethyl cellulose, gelatin, polyethylene, polypropylene, polycarbonate and other polymers, as well as other compounds such as silane coupling agents, etc. Preferred examples of the polymer are water-soluble polymers such as poly(N-methylolacrylamide), carboxymethyl cellulose, gelatin, polyvinyl alcohol and modified polyvinyl alcohol, etc. More preferred are gelatin, polyvinyl alcohol and modified polyvinyl alcohol; and more preferred are polyvinyl alcohol and modified polyvinyl alcohol.

(9) Use of Film of the Invention

One embodiment of the film of the invention is a film which is produced by fixing the alignment of the liquid-crystal phase (for example, horizontal alignment, vertical alignment, hybrid alignment, etc.) of the composition of the invention and which shows optical anisotropy. The film is utilized as an optical compensatory film or the like in liquid-crystal display devices, etc.

One embodiment of the film of the invention is a film which is produced by fixing the cholesteric liquid-crystal phase of the polymerizable composition of the invention and which exhibits selective reflection characteristics against a light falling within a predetermined wavelength range. The film that exhibits selective reflection characteristics within the IR wavelength range (having a wavelength of from 800 to 1300 nm) may be, for example, stuck to windowpanes of buildings or vehicles or may be incorporated in laminated glass and may be thereby used as a heat-insulating member therein.

In addition, the film of the invention can be utilized in many applications for polarizing elements, selective reflection films, color filters, antireflection films, viewing angle compensation films, holography, alignment films and others that are constituent elements of optical devices.

3. Polymer

The invention also relates to a polymer produced by polymerizing one or more polymerizable compounds of the above-mentioned formula (I), and to a polymer produced by polymerizing the polymerizable composition containing the polymerizable compound of the invention. The polymer may be a liquid-crystalline one or non-liquid-crystalline one. As containing the recurring unit derived from the polymerizable compound of the formula (I), the polymer shows a high Δn and is useful as a material for various optical elements.

EXAMPLES

The characteristics of the invention are described more concretely with reference to Examples and Comparative Examples given below (however, Comparative Examples are not always known techniques). In the following Examples, the material used, its amount and ratio, the details of the treatment and the treatment process may be suitably modified or changed not overstepping the spirit and the scope of the invention. Accordingly, the scope of the invention should not be limitatively interpreted by the Examples mentioned below.

1. Synthesis Examples and Physical Data of Compounds of Formula (I)

(1) Example 1

Synthesis of Exemplary Compound (I-2)

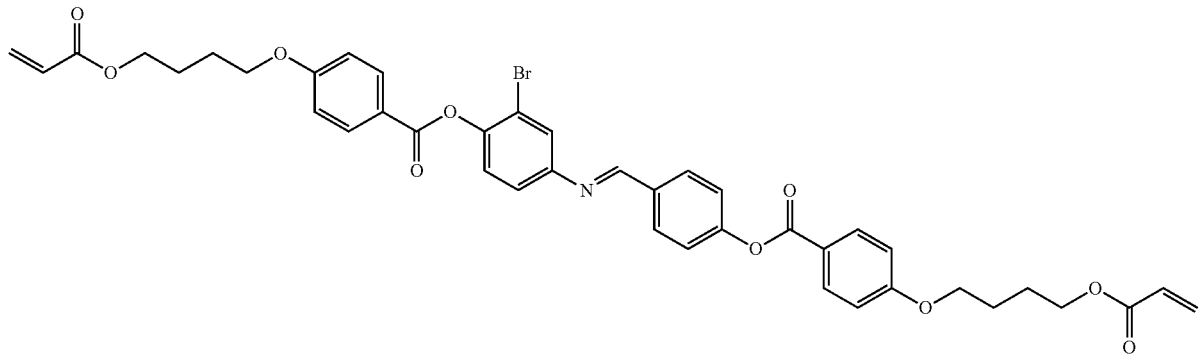

(I-2)

(1) 7.32 g (60 mmol) of 4-hydroxybenzaldehyde was added to a three-neck flask to which 30 ml of toluene had been added. In a nitrogen atmosphere, the inner temperature was raised up to 40° C., and then 11.3 g (60 mmol) of 4-amino-o-bromophenol was added thereto. Subsequently, this was refluxed for 2 hours, and then water and toluene were completely evaporated away with a Dean Stark apparatus to give a yellow solid. The solid was completely dissolved in 50 ml of THF (this is solution A).

(2) Separately, 10.2 ml (132 mmol) of MsCl and 20 ml of THF were added to a three-neck flask, and immersed in an ice/methanol bath so that the inner temperature was made −5° C. While its inner temperature was kept at 5° C. or lower, a mixed solution of 4-acryloyloxybenzoic acid 31.7 g (120 mmol)/diisopropylethylamine (hereinafter referred to as DIPEA), 26.1 ml (150 mmol)/2,6-di-t-butyl-4-methylphenol (0.30 g)/THF (70 ml) was dropwise added to the above solution. While kept at 5° C. or lower, this solution was stirred for 2 hours, and then 26.1 ml (150 mmol) of DIPEA, 0.15 g of DMAP and the solution A prepared in (1) were added thereto in that order (whereupon the inner temperature was kept at 5° C. or lower). The reaction temperature was elevated up to 25° C., and the reaction mixture was stirred for 2 hours and then quenched with 10 ml of methanol added thereto. This was processed for liquid-liquid separation with ethyl acetate/pure water added thereto, and the organic layer was dried with sodium sulfate and then concentrated to give a crude crystal. The crude crystal was recrystallized with ethyl acetate/methanol to give 29.7 g (yield 63%) of a white solid, compound (I-2).

1H-NMR (CDCl$_3$): δ=1.8-2.0 (brs, 8H), 4.1 (brs, 4H), 4.3 (brs, 4H), 5.8 (d, 2H), 6.1 (dd, 2H), 6.4 (d, 2H), 7.0 (d×2, 4H), 7.2-7.3 (d×3, 6H), 7.5 (s, 1H), 8.0 (d, 2H), 8.2 (d×2, 4H), 8.5 (s, 1H).

(2) Example 2

Synthesis of Exemplary Compound (I-5)

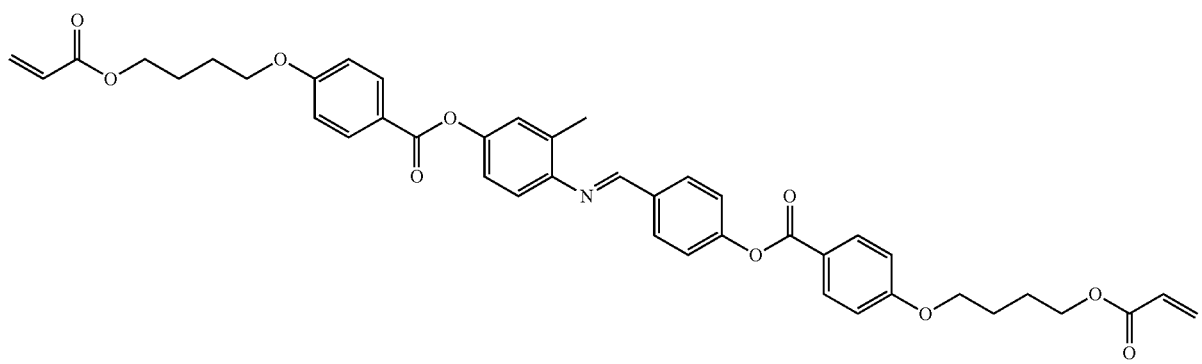

(I-5)

This was synthesized according to the same method as in Example 1 except that 4-amino-m-cresol was used in place of 4-amino-o-bromophenol. The yield was 28.9 g (67%).

1H-NMR (CDCl$_3$): δ=1.8-2.0 (brs, 8H), 2.4 (s, 3H), 4.0-4.1 (m, 4H), 4.2-4.3 (m, 4H), 5.8 (d, 2H), 6.2 (dd, 2H), 6.4 (d, 2H), 6.9-7.1 (d, 7H), 7.3-7.4 (d, 2H), 8.0 (d, 2H), 8.1 (m, 4H), 8.4 (s, 1H).

(3) Example 3

Synthesis of Exemplary Compound (I-6)

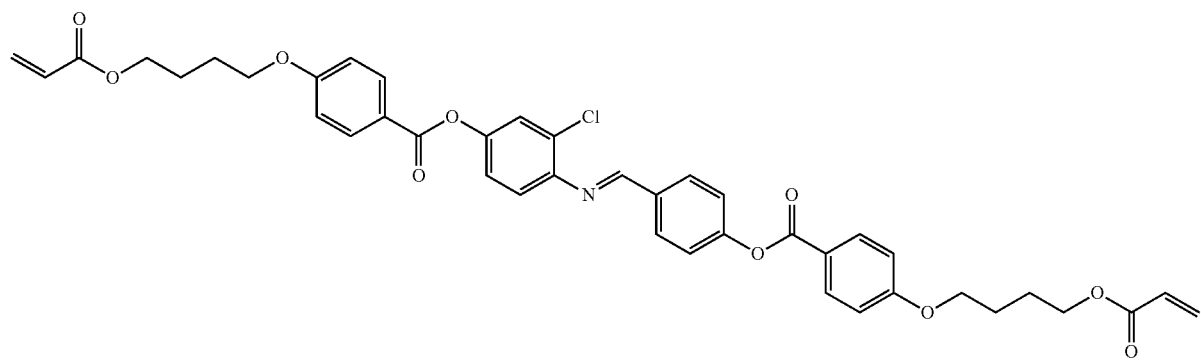

(I-6)

This was synthesized according to the same method as in Example 1 except that 4-amino-3-chlorophenol was used in place of 4-amino-o-bromophenol. The yield was 26.6 g (60%).

1H-NMR (CDCl$_3$): δ=1.8-2.0 (brs, 8H), 4.0-4.2 (brs, 4H), 4.2-4.3 (brs, 4H), 5.8 (d, 2H), 6.1 (dd, 2H), 6.4 (d, 2H), 7.0 (d, 4H), 7.1 (d, 1H), 7.2 (d, 1H), 7.3 (m, 3H), 8.0 (d, 2H), 8.1 (d×2, 4H), 8.4 (s, 1H).

(4) Example 4

Synthesis of Exemplary Compound (I-4)

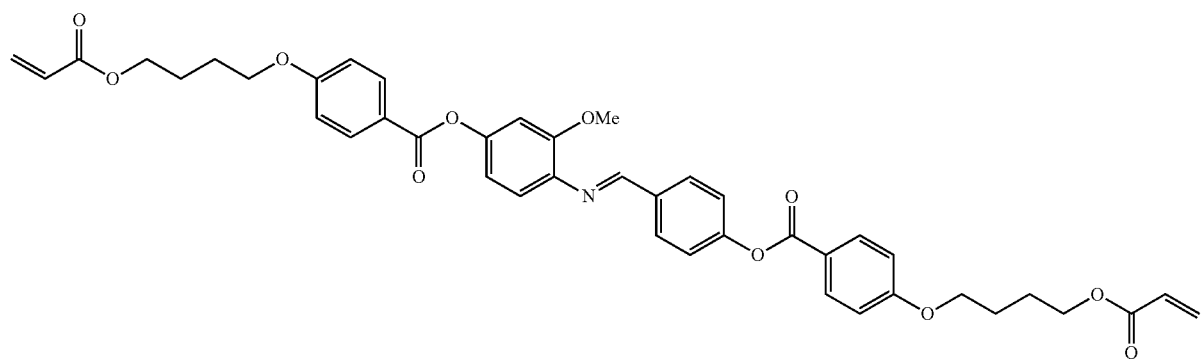

(I-4)

This was synthesized according to the same method as in Example 1 except that 4-amino-3-methoxyphenol was used in place of 4-amino-o-bromophenol. The yield was 25.6 g (58%). 1H-NMR (CDCl$_3$): δ=1.8-2.0 (brs, 8H), 3.9 (s, 3H), 4.1 (brs, 4H), 4.3 (brs, 4H), 5.8 (d, 2H), 6.1 (dd, 2H), 6.4 (d, 2H), 6.8 (d, 2H), 7.0 (d, 4H), 7.1 (d, 1H), 7.3 (d, 2H), 8.0 (d, 2H), 8.2 (d, 4H), 8.5 (s, 1H).

(5) Example 5

Synthesis of Exemplary Compound (I-3)

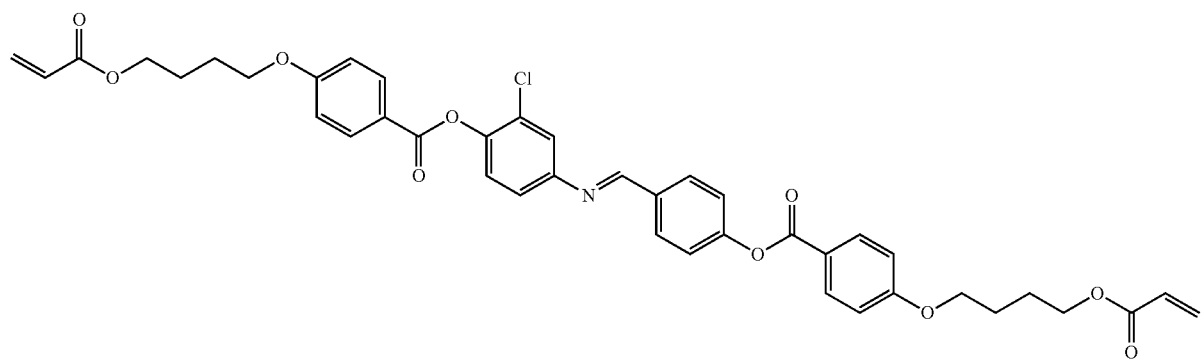

(I-3)

This was synthesized according to the same method as in Example 1 except that 4-amino-2-chlorophenol was used in place of 4-amino-o-bromophenol. The yield was 28.0 g (63%).

1H-NMR (CDCl$_3$): δ=1.8-2.0 (brs, 8H), 4.1 (brs, 4H), 4.3 (brs, 4H), 5.8 (d, 2H), 6.1 (dd, 2H), 6.4 (d, 2H), 7.0 (d, 4H), 7.2 (d, 1H), 7.3 (m, 4H), 8.0 (d, 2H), 8.2 (d×2, 4H), 8.5 (s, 1H).

(6) Example 6

Synthesis of Exemplary Compound (I-1)

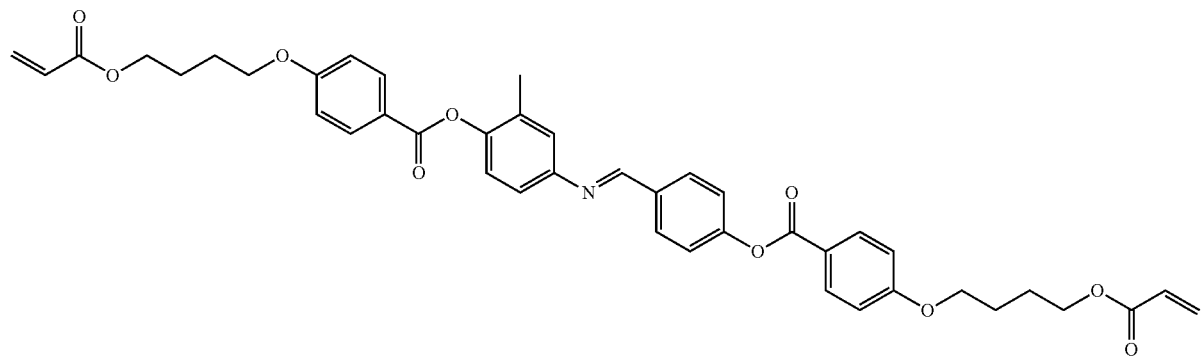

(I-1)

This was synthesized according to the same method as in Example 1 except that 4-amino-o-cresol was used in place of 4-amino-o-bromophenol. The yield was 30.7 g (71%).

1H-NMR (CDCl$_3$): δ=1.8-2.0 (brs, 8H), 2.3 (s, 3H), 4.1 (brs, 4H), 4.3 (brs, 4H), 5.8 (d, 2H), 6.1 (dd, 2H), 6.4 (d, 2H), 7.0 (d, 4H), 7.1-7.2 (m, 3H), 7.3 (d, 2H), 8.0 (d, 2H), 8.2 (d, 4H), 8.5 (s, 1H).

(7) Example 7

Synthesis of Exemplary Compound (I-9)

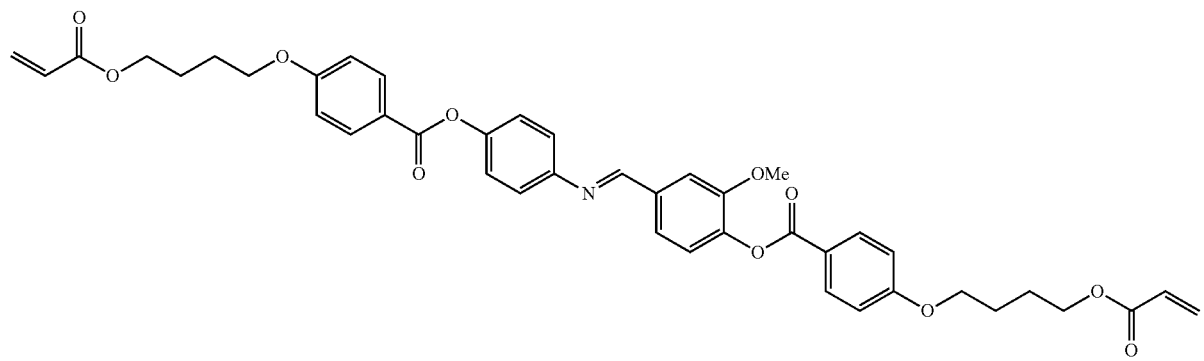

(I-9)

This was synthesized according to the same method as in Example 1 except that 4-aminophenol was used in place of 4-amino-o-bromophenol and that vanillin was used in place of 4-hydroxybenzaldehyde. The yield was 28.7 g (65%).

1H-NMR (DMSO): δ=1.7-1.9 (brs, 8H), 3.8 (s, 3H), 4.1-4.3 (m, 8H), 5.9 (d, 2H), 6.2 (dd, 2H), 6.3 (d, 2H), 7.1 (d, 4H), 7.3-7.4 (d×2, 5H), 7.6 (d, 1H), 7.7 (s, 1H), 8.1 (m, 4H), 8.7 (s, 1H).

(8) Example 8

Synthesis of Exemplary Compound (I-13)

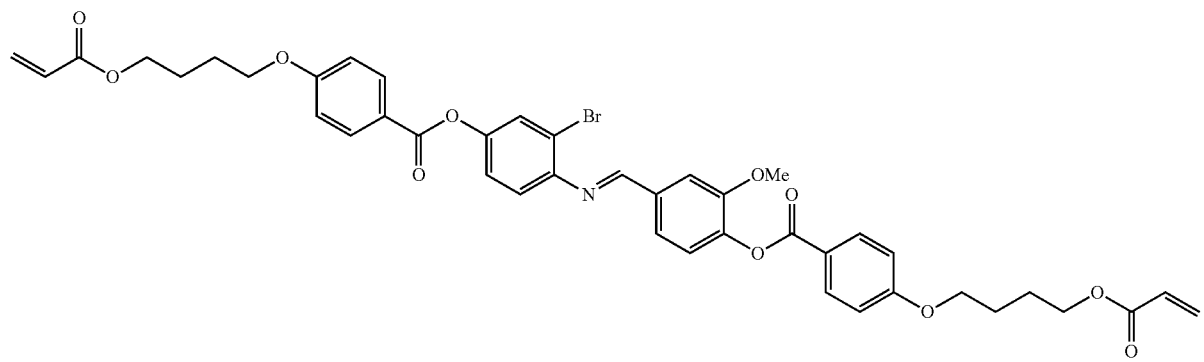

(I-13)

This was synthesized according to the same method as in Example 1 except that 4-amino-3-bromophenol was used in place of 4-amino-o-bromophenol and that vanillin was used in place of 4-hydroxybenzaldehyde. The yield was 30.3 g (62%).

1H-NMR (CDCl$_3$): δ=1.8-2.0 (brs, 8H), 3.9 (s, 3H), 4.1 (brs, 4H), 4.3 (brs, 4H), 5.8 (d, 2H), 6.1 (dd, 2H), 6.4 (d, 2H), 7.0 (d, 4H), 7.1 (d, 1H), 7.2 (d, 1H), 7.3 (d, 1H), 7.4 (d, 1H), 7.5 (s, 1H), 7.8 (s, 1H), 8.2 (d, 4H), 8.5 (s, 1H).

(9) Example 9

Synthesis of Exemplary Compound (I-15)

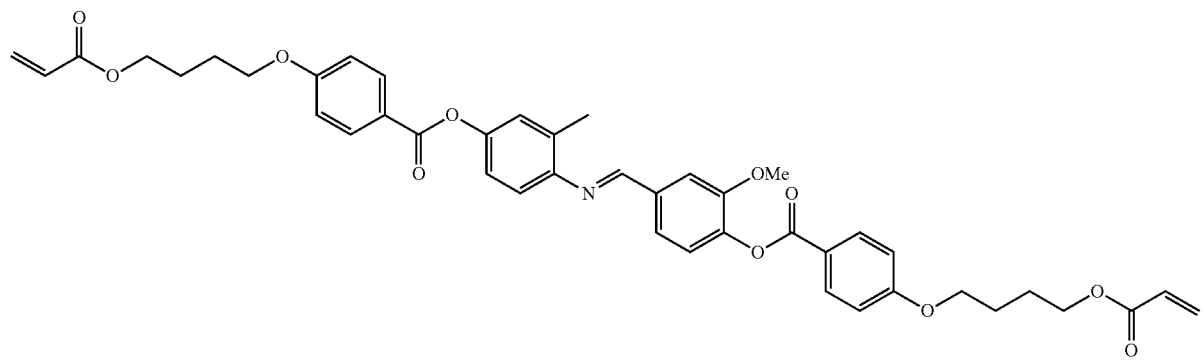

(I-15)

This was synthesized according to the same method as in Example 1 except that 4-amino-m-cresol was used in place of 4-amino-o-bromophenol and that vanillin was used in place of 4-hydroxybenzaldehyde. The yield was 26.5 g (59O).

1H-NMR (CDCl$_3$): δ=1.8-2.0 (brs, 8H), 2.4 (s, 3H), 3.9 (s, 3H), 4.1 (m, 4H), 4.3 (m, 4H), 5.8 (d, 2H), 6.1 (dd, 2H), 6.4 (d, 2H), 7.0 (d×2, 4H), 7.1 (m, 3H), 7.4 (d, 1H), 7.7 (s, 1H), 8.2 (d×2, 4H), 8.4 (s, 1H).

(10) Example 10

Synthesis of Exemplary Compound (II-1)

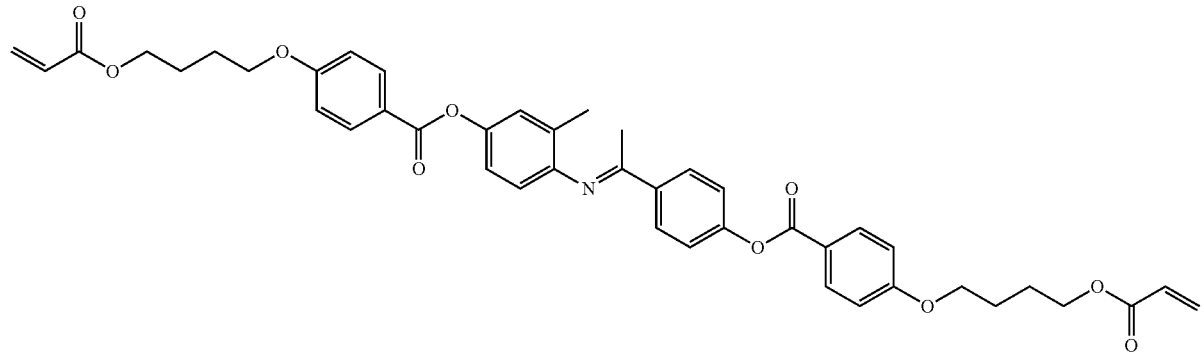

(II-1)

This was synthesized according to the same method as in Example 1 except that 4-amino-m-cresol was used in place of 4-amino-o-bromophenol and that 4-hydroxyacetophenone was used in place of 4-hydroxybenzaldehyde. The yield was 25.5 g (58%). 1H-NMR (CDCl$_3$): δ=1.8-2.0 (brs, 8H), 2.1 (s, 3H), 2.3 (s, 3H), 4.1 (brs, 4H), 4.3 (brs, 4H), 5.8 (d, 2H), 6.2 (dd, 2H), 6.4 (d, 2H), 6.7 (d, 1H), 6.9-7.1 (m, 6H), 7.3-7.4 (d, 2H), 8.0-8.3 (m, 6H).

(11) Example 11

Synthesis of Exemplary Compound (I-7)

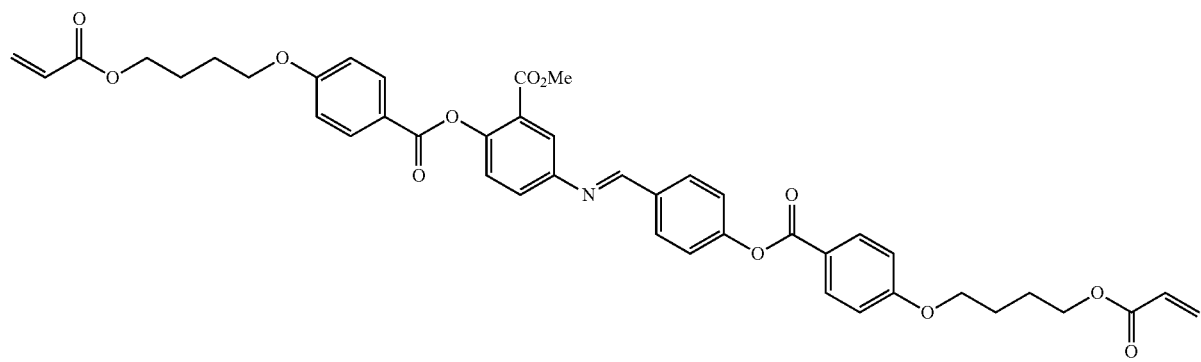
(I-7)

This was synthesized according to the same method as in Example 1 except that 4-amino-2-methoxycarbonylphenol was used in place of 4-amino-o-bromophenol. The yield was 27.5 g (60%).

1H-NMR (CDCl$_3$): δ=1.8-2.0 (brs, 8H), 3.7 (s, 3H), 4.1 (brs, 4H), 4.3 (brs, 4H), 5.8 (d, 2H), 6.1 (dd, 2H), 6.4 (d, 2H), 7.0 (d, 4H), 7.3 (d, 2H), 7.5 (d, 1H), 7.9 (s, 1H), 8.0 (d, 2H), 8.2 (d, 4H), 8.5 (s, 1H).

(12) Example 12

Synthesis of Exemplary Compound (I-12)

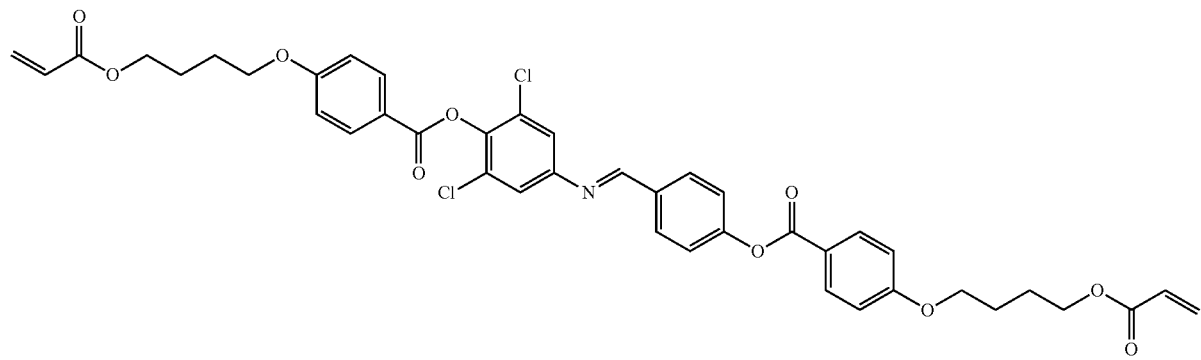
(I-12)

This was synthesized according to the same method as in Example 1 except that 4-amino-2,6-dichlorophenol was used in place of 4-amino-o-bromophenol. The yield was 28.4 g (61%). $^1$H-NMR (DMSO): δ=1.8-2.0 (brs, 8H), 4.1-4.3 (brs, 8H), 5.9 (d, 2H), 6.2 (dd, 2H), 6.4 (d, 2H), 7.1 (d×2, 4H), 7.4 (d, 2H), 7.6 (s×2, 2H), 8.0-8.2 (d×3, 6H), 8.8 (s, 1H).

(13) Example 13

Synthesis of Exemplary Compound (I-10)

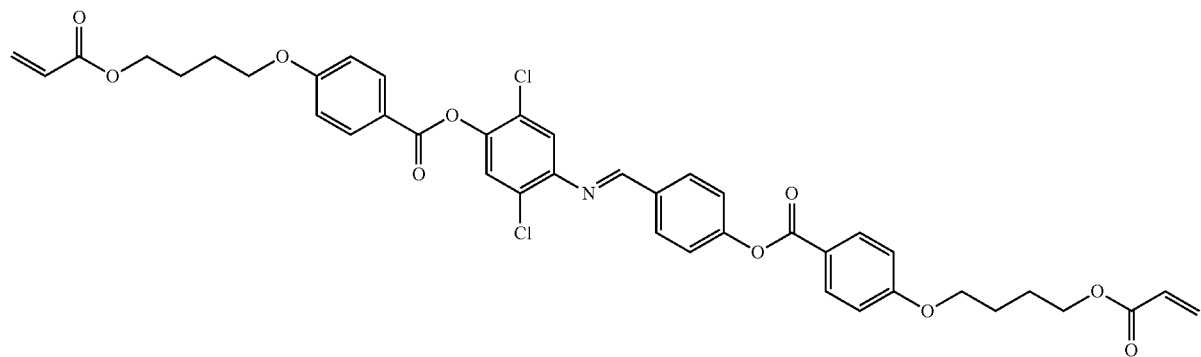

This was synthesized according to the same method as in Example 1 except that 4-amino-2,5-dichlorophenol was used in place of 4-amino-o-bromophenol. The yield was 29.7 g (64%). 1H-NMR (DMSO): δ=1.8-2.0 (brs, 8H), 4.1-4.3 (brs, 8H), 5.9 (d, 2H), 6.2 (dd, 2H), 6.3 (d, 2H), 7.1 (d×2, 4H), 7.5 (d, 2H), 7.7 (s, 1H), 7.8 (s, 1H), 8.0-8.2 (m, 6H), 8.7 (s, 1H).

(14) Example 14

Synthesis of Exemplary Compound (I-11)

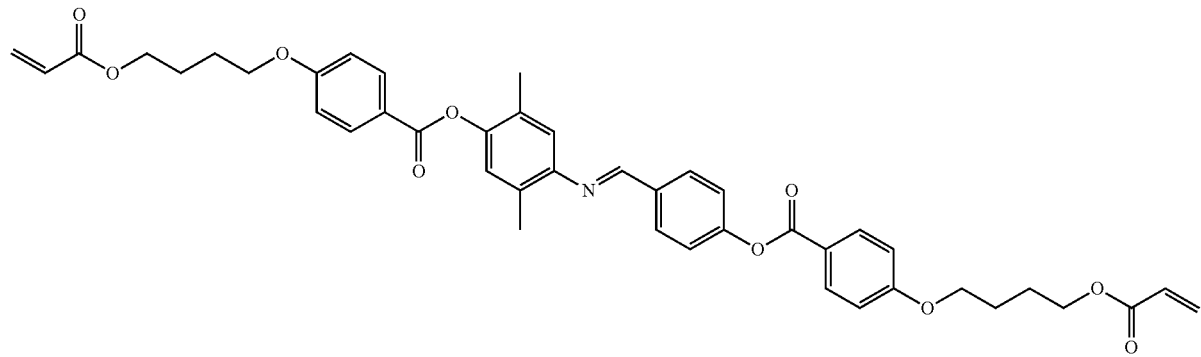

This was synthesized according to the same method as in Example 1 except that 4-amino-2,5-dimethylphenol was used in place of 4-amino-o-bromophenol. The yield was 29.5 g (62%). $^1$H-NMR (DMSO): δ=1.8-2.0 (brs, 8H), 2.1 (s, 3H), 2.3 (s, 3H), 4.0-4.2 (brs, 8H), 5.9 (d, 2H), 6.2 (dd, 2H), 6.3 (d, 2H), 7.1 (d, 2H), 7.2 (d×2, 4H), 7.4 (d, 2H), 8.0-8.2 (m, 6H), 8.6 (s, 1H).

(15) Example 15

Synthesis of Exemplary Compound (V-1)

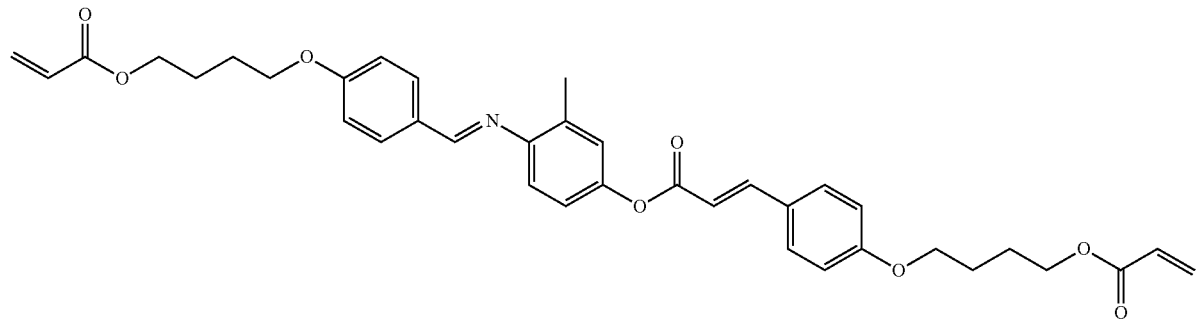

(V-1)

(1) 12.4 g (50 mmol) of 4-acryloyloxybenzaldehyde was added to a three-neck flask to which 0.30 g of 2,6-di-t-butyl-4-methylphenol and 20 ml of toluene had been added. In a nitrogen atmosphere, the inner temperature was raised up to 40° C., and then 6.2 g (50 mmol) of 4-amino-m-cresol was added thereto. Subsequently, this was refluxed for 2 hours, and then water and toluene were completely evaporated away with a Dean Stark apparatus to give a brown oily substance. The oily substance was completely dissolved in 30 ml of THF (this is solution A).

(2) Separately, 4.3 ml (55 mmol) of MsCl and 10 ml of THF were added to a three-neck flask, and immersed in an ice/methanol bath so that the inner temperature was made −5° C. While its inner temperature was kept at 5° C. or lower, a mixed solution of 4-acryloyloxycinnamic acid (14.5 g, 50 mmol)/diisopropylethylamine (hereinafter referred to as DIPEA, 9.6 ml, 55 mmol)/2,6-di-t-butyl-4-methylphenol (0.30 g)/THF (30 ml) was dropwise added to the above solution. While kept at 5° C. or lower, this solution was stirred for 2 hours, and then 9.6 ml (55 mmol) of DIPEA, 0.15 g of DMAP and the solution A prepared in (1) were added thereto in that order (whereupon the inner temperature was kept at 5° C. or lower). The reaction temperature was elevated up to 25° C., and the reaction mixture was stirred for 2 hours and then quenched with 10 ml of methanol added thereto. This was processed for liquid-liquid separation with ethyl acetate/pure water added thereto, and the organic layer was dried with sodium sulfate and then concentrated to give a brown oily substance. The oily substance was concentrated through a column of ethyl acetate/hexane, and recrystallized with MeOH to give 6.3 g (yield 20%) of a white solid, compound (V-1).

1H-NMR (CDCl$_3$): δ=1.8-2.0 (brs, 8H), 2.4 (s, 3H), 4.1 (m, 4H), 4.3 (m, 4H), 5.8 (d, 2H), 6.1 (dd, 2H), 6.4 (d, 2H), 6.5 (d, 1H), 6.9-7.1 (m, 7H), 7.5 (d, 2H), 7.8 (d×2, 3H), 8.3 (s, 1H).

(16) Example 16

Synthesis of Exemplary Compound (V-2)

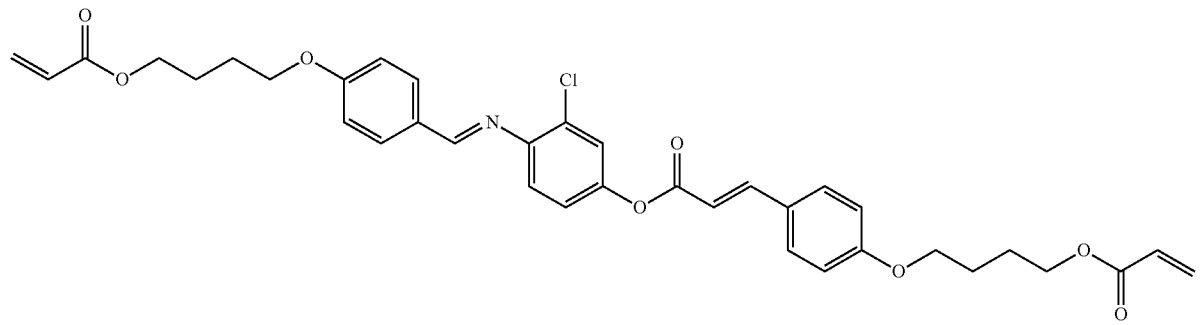

(V-2)

This was synthesized according to the same method as in Example 15 except that 4-amino-3-chlorophenol was used in place of 4-amino-m-cresol. The yield was 5.8 g (18%).

1H-NMR (DMSO): δ=1.8-2.0 (brs, 8H), 4.0 (m, 4H), 4.2 (m, 4H), 5.9 (d, 2H), 6.1 (dd, 2H), 6.4 (d, 2H), 6.7 (d, 1H), 7.0 (d, 2H), 7.1 (d, 2H), 7.2 (d, 1H), 7.3 (d, 1H), 7.4 (s, 1H), 7.7 (d, 2H), 7.8 (d, 1H), 7.9 (d, 2H), 8.5 (s, 1H).

(17) Example 17

Synthesis of Exemplary Compound (V-7)

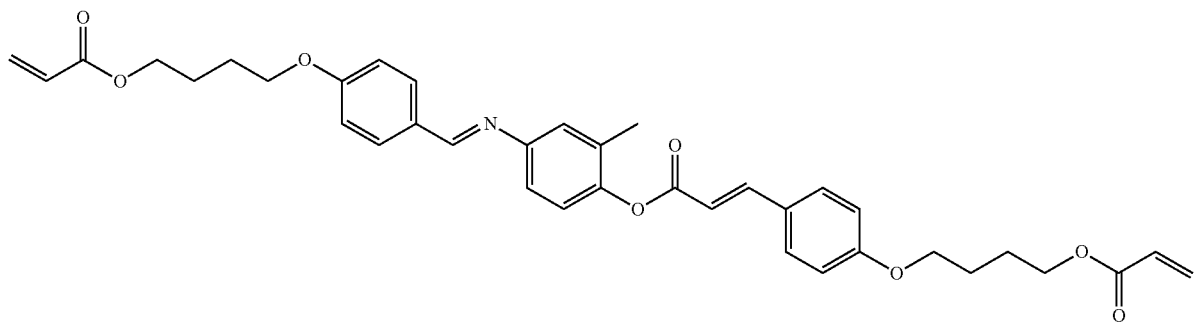

(V-7)

This was synthesized according to the same method as in Example 15 except that 4-amino-o-cresol was used in place of 4-amino-m-cresol. The yield was 5.9 g (19%).

1H-NMR (CDCl$_3$): δ=1.8-2.0 (brs, 8H), 2.3 (s, 3H), 4.1 (m, 4H), 4.3 (m, 4H), 5.8 (d, 2H), 6.1 (dd, 2H), 6.4 (d, 2H), 6.5 (d, 1H), 7.0 (d×2, 4H), 7.1 (m, 3H), 7.5 (d, 2H), 7.8 (m, 3H), 8.4 (s, 1H).

(18) Example 18

Synthesis of Exemplary Compound (V-8)

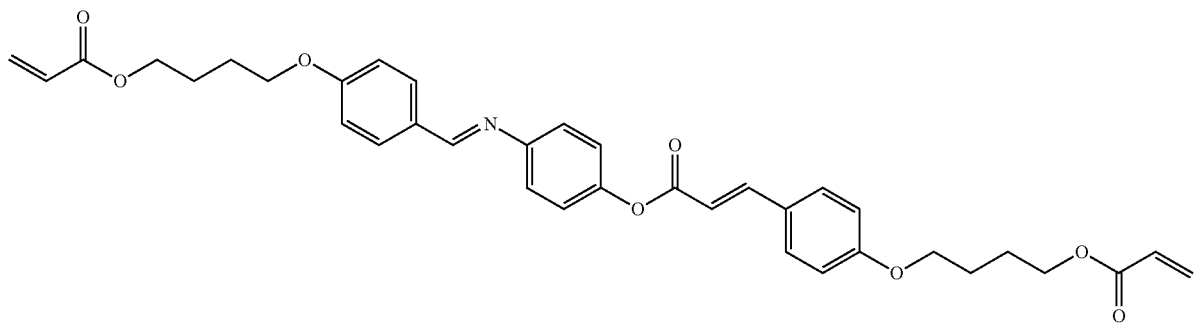

(V-8)

This was synthesized according to the same method as in Example 15 except that 4-aminophenol was used in place of 4-amino-m-cresol. The yield was 9.5 g (31%).

1H-NMR (CDCl$_3$): δ=1.8-2.0 (brs, 8H), 4.1 (m, 4H), 4.3 (m, 4H), 5.8 (d, 2H), 6.1 (dd, 2H), 6.4 (d, 2H), 6.5 (s, 1H), 7.0 (d×2, 4H), 7.0 (d×2, 4H), 7.5 (d, 2H), 7.8 (d×2, 3H), 8.4 (s, 1H).

(19) Example 19

Synthesis of Exemplary Compound (VII-1)

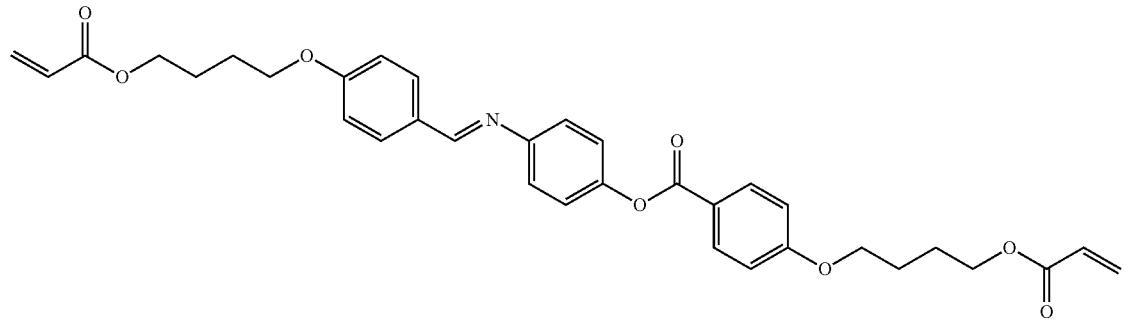

(VII-1)

This was synthesized according to the same method as in Example 15 except that 4-acryloyloxybenzoic acid was used in place of 4-acryloyloxycinnamic acid. The yield was 5.7 g (19%).

1H-NMR (CDCl$_3$): δ=1.8-2.0 (brs, 8H), 2.4 (s, 3H), 4.1 (m, 4H), 4.3 (m, 4H), 5.8 (d, 2H), 6.2 (dd, 2H), 6.4 (d, 2H), 6.9-7.1 (m, 7H), 7.8 (d, 2H), 8.1 (d, 2H), 8.3 (s, 1H).

Physical Properties of Compounds of Formula (I):

Δn of the compounds synthesized in the above was directly measured according to the method described in Liquid Crystal Handbook (by Liquid Crystal Handbook Editorial Committee), p. 202. Concretely, each compound synthesized in the above was injected into a wedge-shaped cell, this was irradiated with a laser light at a wavelength of 550 nm, and the refraction angle of the transmitted light was measured to determine Δn of the compound.

Figure 2:
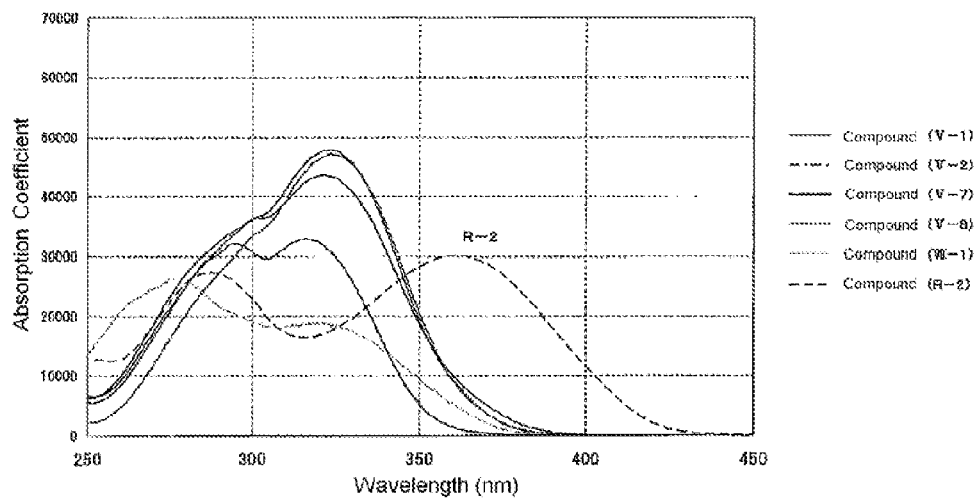
[FIG. 2] This shows absorption spectrum curves of compounds of the formula (I) and a comparative compound, as measured in Examples.
Figure 3:
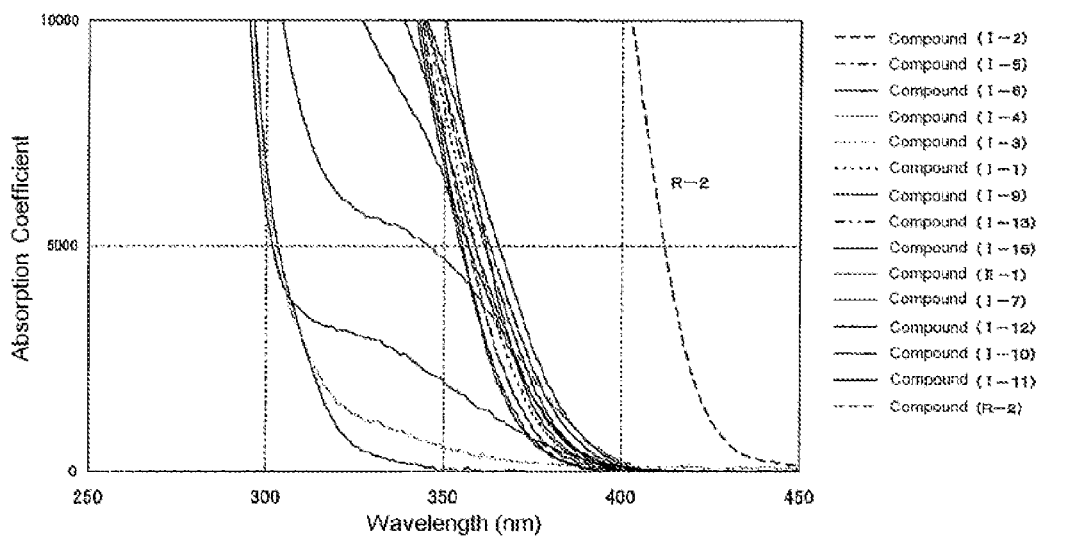
[FIG. 3] This shows enlarged graphs of the absorption spectrum curves in FIG. 1.
Figure 4:
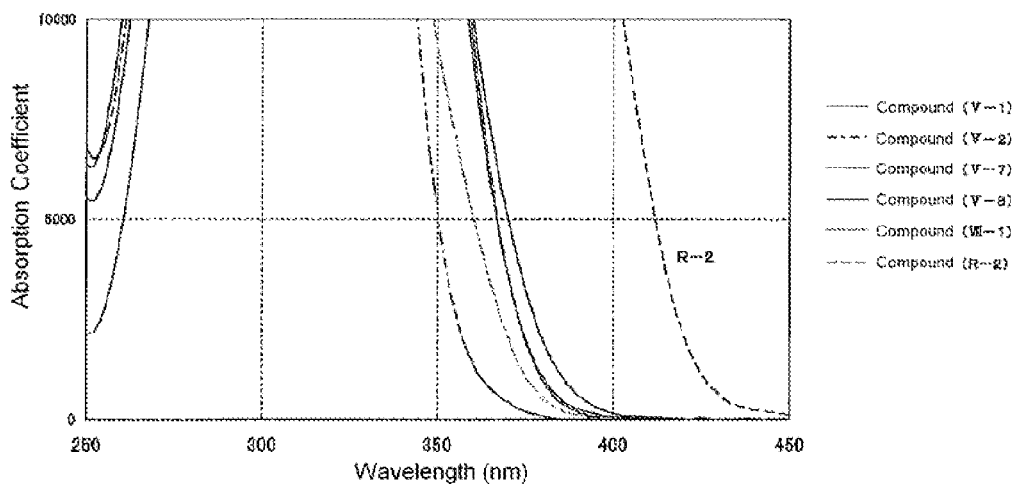
[FIG. 4] This shows enlarged graphs of the absorption spectrum curves in FIG. 2.

The following Table shows Δn of each compound, the phase transition temperature thereof as measured through texture observation with a polarizing microscope, and the color of the crystal. As Comparative Examples, Δn, the phase transition temperature and the color of the solid of the following compounds (R-1), (R-2) and (R-3) for Comparative Compounds are also shown therein. The temperature in the column of "Δn" in the following Table means the measured temperature. In addition, the absorption spectra of the series of the compounds are shown in FIGS. 1 and 2. The graphs of FIG. 3 are partly-enlarged graphs of the graphs of FIG. 1; and the graphs of FIG. 4 are partly-enlarged graphs of FIG. 2.

(R-1) is a liquid-crystal compound containing one azomethine group, that is a monoazomethine compound, in which, however, the side chain to link the polymerizable group and the mesogen therein is short; (R-2) is a bisazomethine compound; and (R-3) is a liquid-crystal compound not containing an azomethine group.

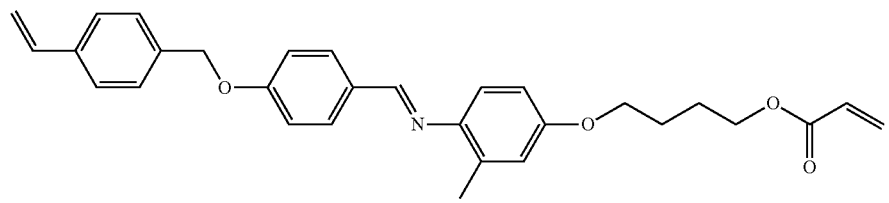

(R-1)

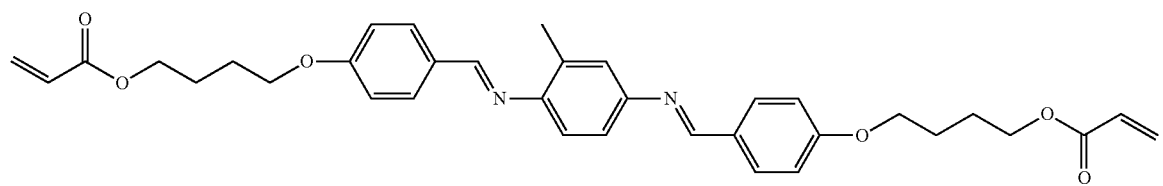

(R-2)

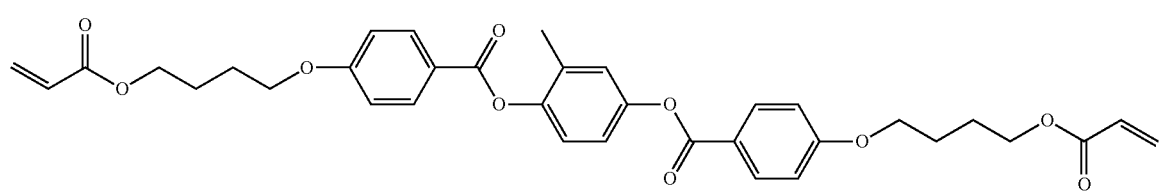

(R-3)

TABLE 1

| | Tested Compound | Phase Transition Temperature | Δn | Color |
|---|---|---|---|---|
| Example 1 | Compound (I-2) | Cr 80 N 250° C. or more Iso | 0.252 (70° C.) | white |
| Example 2 | Compound (I-5) | Cr 120 N 255 Iso | 0.258 (70° C.) | white |
| Example 3 | Compound (I-6) | Cr 111 N 250° C. or more Iso | 0.256 (70° C.) | white |
| Example 4 | Compound (I-4) | Cr 115 N 210 Iso | 0.249 (70° C.) | white |
| Example 5 | Compound (I-3) | Cr 91 N 250° C. or more Iso | 0.262 (70° C.) | white |
| Example 6 | Compound (I-1) | Cr 92 N 250° C. or more Iso | 0.259 (70° C.) | white |
| Example 7 | Compound (I-9) | Cr 98 N 228 Iso | 0.257 (70° C.) | white |
| Example 8 | Compound (I-13) | Cr 102 N 192 Iso | 0.230 (70° C.) | white |
| Example 9 | Compound (I-15) | Cr 97 N 201 Iso | 0.240 (70° C.) | white |
| Example 10 | Compound (II-1) | Cr 106 N 223 Iso | immeasurable as crystallized | white |
| Example 11 | Compound (I-7) | Cr 67 N 232 Iso | 0.258 (70° C.) | white |
| Example 12 | Compound (I-12) | Cr 95 N 217 Iso | 0.255 (70° C.) | white |
| Example 13 | Compound (I-10) | Cr 78 N 227 Iso | 0.251 (70° C.) | white |
| Example 14 | Compound (I-11) | Cr 87 N 221 Iso | 0.240 (70° C.) | white |
| Example 15 | Compound (V-1) | Cr 80 N 167 Iso | 0.286 (70° C.) | white |
| Example 16 | Compound (V-2) | Cr 84 N 164 Iso | 0.276 (70° C.) | white |
| Example 17 | Compound (V-7) | Cr 80 N 167 Iso | 0.290 (70° C.) | white |
| Example 18 | Compound (V-8) | Cr 76 Sc 112 N 209 Iso | 0.285 (100° C.) | white |
| Example 19 | Compound (VII-1) | Cr 111 N 179 Iso | immeasurable as crystallized | white |
| Comparative Example 1 | Compound R-1 | Cr 77 N 118 Iso | 0.239 (70° C.) | white |
| Comparative Example 2 | Compound R-2 | Cr 79 N 145 Iso | 0.319 (70° C.) | yellow |
| Comparative Example 3 | Compound R-3 | Cr 80 N 124 Iso | 0.162 (70° C.) | white |

From the results shown in the above Table, it is understood that the compounds of the formula (I) all have a high Δn as compared with the monoazomethine-type polymerizable liquid-crystal compound (R-1) falling outside the scope of the formula (I) and the liquid-crystal compound (R-3) not containing an azomethine group. From the absorption spectrum curves shown in FIG. 1 and FIG. 2, it is understood that the bisazomethine-type polymerizable liquid crystal (R-2) that has heretofore been known in the art has an absorption at a wavelength of 400 nm or more and is therefore yellowish, but that the absorption at a wavelength of 400 nm or more by the monoazomethine compounds of the formula (I) of the invention is small and therefore the compounds are white.

2. Production and Evaluation of Retardation Films
Examples 20 to 38, Comparative Examples 4 and 5

(1) Example 20

Production of Retardation Film

Using the compound (I-2) of the invention that had been synthesized in Example 1, a liquid-crystal composition coating liquid (1) comprising the following ingredients was prepared.

| | |
|---|---|
| Exemplary Compound (I-2) | 100 parts by mass |
| Air-Interface Alignment Agent (1) | 0.1 parts by mass |
| Polymerization Initiator IRGACURE 819 (by Ciba Japan) | 3 parts by mass |
| Solvent, chloroform | 800 parts by mass |

[Chemical formula 40]

Air-Interface Alignment Agent (1)

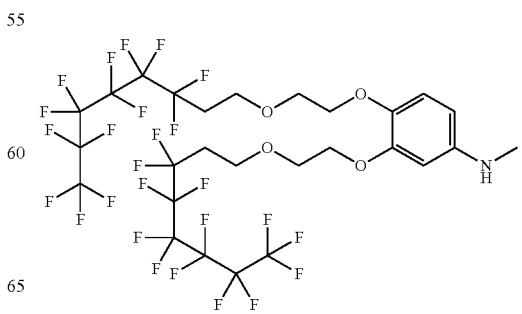

-continued

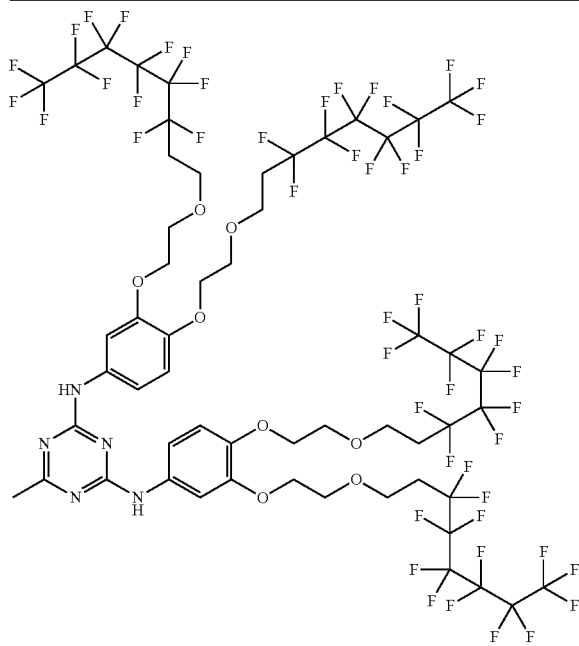

Next, a polyimide alignment film material, Nissan Chemical's SE-130 was applied onto a washed glass substrate according to a spin coating method, dried and then fired at 250° C. for 1 hour. This was rubbed to produce an alignment film-having substrate. Onto the rubbed surface of the alignment film of the substrate, the liquid-crystal composition coating liquid (1) was applied at room temperature according to a spin coating method, then ripened for alignment at 120° C. for 30 seconds, and thereafter photoirradiated with a high-pressure mercury lamp, from which the short-wavelength UV ingredient had been removed, in a nitrogen gas atmosphere at room temperature for 10 seconds for alignment fixation to thereby produce a retardation film of Example 20. During the period after coating and before heating, the coating film did not crystallize.

The retardation film that had been obtained through alignment fixation of the liquid-crystal compound was observed with a polarizing microscope, which confirmed uniform monoaxial orientation with no orientation defect in the film.

Further, the film was analyzed with AXOMETRIX's AxoScan in a tip-tilt mode. As a result, the mean tilt angle of the liquid crystal, as computed by this apparatus, was 1 degree, and this confirmed the formation of an A-plate-type retardation film.

As computed from the retardation measured by the use of the above apparatus and from the thickness of the retardation film 1 measured by the use of a confocal laser thickness meter (Keyence's FV-7510), Δn at a wavelength of 550 nm was 0.273, and the haze was 0.07.

(2) Examples 21 to 38

Production of Retardation Films

Liquid-crystal composition coating liquids were prepared in the same manner as above except that the compounds synthesized in the above Examples were used in place of the exemplary compound (I-2). Using the coating liquids and in the same manner as in Example 20, retardation films of Examples were produced.

These retardation films all exhibited good orientation performance and had a low haze of at most 0.1. The data of Δn of the retardation films, as determined in the same manner as in Example 20, are collectively shown in the following Table.

(3) Comparative Example 4

Production of Retardation Film of Comparative Example

A liquid-crystal composition coating liquid (2) comprising the following ingredients was prepared in the same manner as in Example 20.

| | |
|---|---|
| Polymerizable Liquid-Crystal Compound (R-1) mentioned above | 100 parts by mass |
| Air-Interface Alignment Agent (1) | 0.1 parts by mass |
| Polymerization Initiator IRGACURE 819 (by Ciba Japan) | 3 parts by mass |
| Solvent, chloroform | 800 parts by mass |

A retardation film of Comparative Example 4 was produced in the same manner as in Example 20 except that the liquid-crystal composition coating liquid (2) was used in place of the liquid-crystal composition coating liquid (1). However, since the liquid crystal uppermost temperature of the liquid-crystal composition was lower than that in Example 20, the temperature for alignment ripening in this case was 90° C. During the period after coating and before heating, a liquid crystal partly deposited on the coating film. Accordingly, even after this was reheated and further processed for alignment ripening, some thickness unevenness still remained in the crystal-deposited part of the film.

As measured according to the same method as in Example 20, Δn at a wavelength of 550 nm of the retardation film of Comparative Example 4 was 0.256, and the haze thereof was 0.18.

(4) Comparative Example 5

Production of Retardation Film of Comparative Example

A liquid-crystal composition coating liquid (3) comprising the following ingredients was prepared in the same manner as in Example 20.

| | |
|---|---|
| Polymerizable Liquid-Crystal Compound (R-2) mentioned above | 100 parts by mass |
| Air-Interface Alignment Agent (1) | 0.1 parts by mass |
| Polymerization Initiator IRGACURE 819 (by Ciba Japan) | 3 parts by mass |
| Solvent, chloroform | 800 parts by mass |

A retardation film of Comparative Example 5 was formed in the same manner as in Example 20 except that the liquid-crystal composition coating liquid (3) was used in place of the liquid-crystal composition coating liquid (1). However, since the liquid crystal uppermost temperature of the polymerizable composition was lower than that in Example 20, the temperature for alignment ripening in this case was 90° C. During the period after coating and before heating, a liquid crystal partly deposited on the coating film. Accordingly, even after this was reheated and further processed for alignment ripening, some thickness unevenness still remained in the crystal-deposited part of the film. As measured according to the same method as in Example 20, Δn at a wavelength of 550 nm of the retardation film of Comparative Example 5 was 0.360, and the haze thereof was 0.13.

The above results are shown in the following Table.

TABLE 2

|  | Tested Compound | Δn | Haze |
|---|---|---|---|
| Example 20 | Compound (I-2) | 0.273 | 0.07 |
| Example 21 | Compound (I-5) | 0.275 | 0.08 |
| Example 22 | Compound (I-6) | 0.271 | 0.09 |
| Example 23 | Compound (I-4) | 0.251 | 0.06 |
| Example 24 | Compound (I-3) | 0.258 | 0.06 |
| Example 25 | Compound (I-1) | 0.276 | 0.07 |
| Example 26 | Compound (I-9) | 0.280 | 0.07 |
| Example 27 | Compound (I-13) | 0.260 | 0.05 |
| Example 28 | Compound (I-15) | 0.262 | 0.07 |
| Example 29 | Compound (II-1) | 0.260 | 0.09 |
| Example 30 | Compound (I-7) | 0.278 | 0.06 |
| Example 31 | Compound (I-12) | 0.276 | 0.08 |
| Example 32 | Compound (I-10) | 0.274 | 0.09 |
| Example 33 | Compound (I-11) | 0.260 | 0.06 |
| Example 34 | Compound (V-1) | 0.320 | 0.08 |
| Example 35 | Compound (V-2) | 0.309 | 0.09 |
| Example 36 | Compound (V-7) | 0.327 | 0.06 |
| Example 37 | Compound (V-8) | 0.270 | 0.07 |
| Example 38 | Compound (VII-1) | 0.262 | 0.07 |
| Comparative Example 4 | Compound R-1 | 0.256 | 0.18 |
| Comparative Example 5 | Compound R-2 | 0.360 | 0.13 |

From the results shown in the above Table, it is understood that the retardation films formed by the use of the compound of the general formula (I) of the invention have a large Δn and a small haze as compared with the retardation film formed by the use of the conventional, monoazomethine-type polymerizable liquid-crystal compound (R-1). In addition, it is also understood that, while the film formed by the use of the conventional, bis-Schiff-type polymerizable liquid-crystal compound (R-2) is yellow, the retardation films of Examples of the invention are all white and have a small haze.

3. Production and Evaluation of Selective Reflection Films Examples 39 to 57, Comparative Examples 6 and 7

(1) Example 39

Production of Selective Reflection Film

Using the exemplary compound (I-2) of the invention, as synthesized in Example 1, a liquid-crystal composition coating liquid (11) comprising the following ingredients was prepared.

| Exemplary Compound (I-2) | 33 parts by mass |
|---|---|
| Polymerizable Liquid-Crystal Compound (R-3) | 67 parts by mass |
| Chiral Agent, Paliocolor LC756 (by BASF) | 3 parts by mass |
| Air-Interface Alignment Agent (1) | 0.04 parts by mass |
| Polymerization Initiator IRGACURE 819 (by Ciba Japan) | 3 parts by mass |
| Solvent, chloroform | 300 parts by mass |

The liquid-crystal composition coating liquid (11) was applied onto the surface of the alignment film of the alignment film-having substrate as produced in the same manner as in Example 20, according to a spin coating method at room temperature, then heated at 120° C. for 3 minutes for alignment ripening, and thereafter photoirradiated with a high-pressure mercury lamp, from which the short-wavelength UV ingredient had been removed, at room temperature for 10 seconds for alignment fixation to thereby produce a selective reflection film of Example 39. During the period after coating and before heating, the coating film did not crystallize.

The obtained selective reflection film was observed with a polarizing microscope, which confirmed uniform monoaxial orientation with no orientation defect in the film. Further, the transmission spectrum of the film was measured with a spectrophotometer, Shimadzu's UV-3100PC, and the spectrum had a selective reflection peak in the IR region having a center at 1000 nm, and the half-value width of the peak was 136 nm. As computed from the peak half-value width and the helical period of the liquid-crystal composition, Δn at a wavelength of 1000 nm was 0.219.

2) Examples 40 to 57

Production of Selective Reflection Films

Liquid-crystal composition coating liquids were prepared in the same manner as in Example 39 except that the exemplary compounds synthesized in the above Examples were used in place of the exemplary compound (I-2). Using the coating liquids and in the same manner as in Example 39, selective reflection films of Examples 40 to 57 were produced. These selective reflection films all exhibited good orientation.

As similarly determined, the peak half-value width of the selective reflection films and Δn thereof obtained from the former are collectively shown in the following Table.

(3) Comparative Example 6

Production of Selective Reflection Film of Comparative Example

In the same manner as in Example 39, a liquid-crystal composition coating liquid (12) comprising the following ingredients was prepared.

| Polymerizable Liquid-Crystal Compound (R-1) | 100 parts by mass |
|---|---|
| Chiral Agent, Paliocolor LC756 (by BASF) | 2.8 parts by mass |
| Air-Interface Alignment Agent (1) | 0.04 parts by mass |
| Polymerization Initiator IRGACURE 819 (by Ciba Japan) | 3 parts by mass |
| Solvent, chloroform | 300 parts by mass |

A selective reflection film of Comparative Example 6 was produced in the same manner as in Example 39 except that the liquid-crystal composition coating liquid (12) was used in place of the liquid-crystal composition coating liquid (11). However, since the liquid crystal uppermost temperature of the liquid-crystal composition was lower than that of the composition used in Example 39, the temperature for alignment ripening in this case was 90° C.

The selective reflection film had a selective reflection peak in the IR region having a center at around 1000 nm, and the half-value width of the peak was 120 nm. As computed from the peak half-value width and the helical period of the liquid-crystal composition, Δn at a wavelength of 1000 nm was 0.190.

(4) Comparative Example 7

Production of Selective Reflection Film of Comparative Example

In the same manner as in Example 39, a liquid-crystal composition coating liquid (13) comprising the following ingredients was prepared.

| | | 33 parts by mass |
|---|---|---|
| Polymerizable Liquid-Crystal Compound (R-2) | | 33 parts by mass |
| Polymerizable Liquid-Crystal Compound (R-3) | | 67 parts by mass |
| Chiral Agent, Paliocolor LC756 (by BASF) | | 2.8 parts by mass |
| Air-Interface Alignment Agent (1) | | 0.04 parts by mass |
| Polymerization Initiator IRGACURE 819 (by Ciba Japan) | | 3 parts by mass |
| Solvent, chloroform | | 300 parts by mass |

A selective reflection film of Comparative Example 7 was produced in the same manner as in Example 39 except that the liquid-crystal composition coating liquid (13) was used in place of the liquid-crystal composition coating liquid (11).

The selective reflection film had a selective reflection peak in the IR region having a center at around 1000 nm, and the half-value width of the peak was 154 nm. As computed from the peak half-value width and the helical period of the liquid-crystal composition, Δn at a wavelength of 1000 nm was 0.243. The film was yellow.

The results are shown in the following Table.

TABLE 3

| | Tested Compound | Δn | Haze | Half-Value Width | Color |
|---|---|---|---|---|---|
| Example 39 | Compound (I-2) | 0.219 | 0.07 | 136 | white |
| Example 40 | Compound (I-5) | 0.208 | 0.07 | 129 | white |
| Example 41 | Compound (I-6) | 0.211 | 0.08 | 131 | white |
| Example 42 | Compound (I-4) | 0.205 | 0.05 | 127 | white |
| Example 43 | Compound (I-3) | 0.213 | 0.09 | 132 | white |
| Example 44 | Compound (I-1) | 0.220 | 0.07 | 136 | white |
| Example 45 | Compound (I-9) | 0.210 | 0.08 | 130 | white |
| Example 46 | Compound (I-13) | 0.202 | 0.06 | 125 | white |
| Example 47 | Compound (I-15) | 0.203 | 0.07 | 126 | white |
| Example 48 | Compound (II-1) | 0.198 | 0.08 | 123 | white |
| Example 49 | Compound (I-7) | 0.216 | 0.09 | 134 | white |
| Example 50 | Compound (I-12) | 0.203 | 0.07 | 126 | white |
| Example 51 | Compound (I-10) | 0.218 | 0.09 | 135 | white |
| Example 52 | Compound (I-11) | 0.208 | 0.08 | 129 | white |
| Example 53 | Compound (V-1) | 0.235 | 0.07 | 146 | white |
| Example 54 | Compound (V-2) | 0.224 | 0.06 | 139 | white |
| Example 55 | Compound (V-7) | 0.224 | 0.08 | 139 | white |
| Example 56 | Compound (V-8) | 0.230 | 0.09 | 143 | white |
| Example 57 | Compound (VII-1) | 0.199 | 0.09 | 123 | white |
| Comparative Example 6 | Compound R-1 | 0.190 | 0.18 | 120 | white |
| Comparative Example 7 | Compound R-2 | 0.243 | 0.15 | 154 | yellow |

From the results shown in the above Table, it is understood that the selective reflection films produced by the use of the compounds of the general formula (I) of the invention have a larger Δn and have a broader selective reflection range, as compared with the selective reflection film produced by the use of the conventional, monoazomethine polymerizable liquid-crystal compound (R-1). Further, it is also understood that, while the film produced by the use of the conventional, bisazomethine polymerizable liquid crystal (R-2) is yellow, the selective reflection films of Examples of the invention are all colorless.

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2011/064258, filed Jun. 22, 2011, and Japanese Application No. 2010-141469, filed Jun. 22, 2010, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims set forth below.

What is claimed is:

1. A compound represented by the following formula (I):

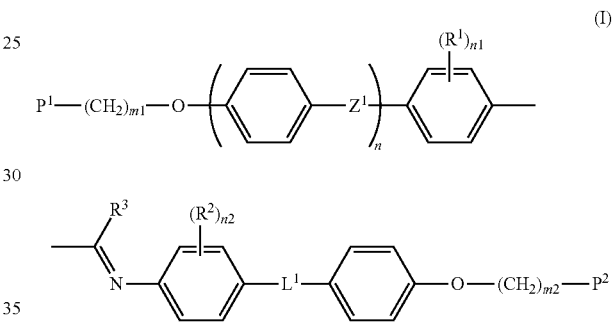

wherein $P^1$ and $P^2$ each represents a polymerizable group selected from the groups represented by the following formulae (P-1) to (P-5):

-continued

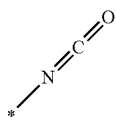
(P-5)

wherein $R^{11}$ to $R^{13}$ each represents a hydrogen atom or a methyl group;

m1 and m2 each indicates an integer of from 2 to 8, and of m1 or m2 $CH_2$'s, one $CH_2$ or two or more $CH_2$'s not adjacent to each other may be replaced by an oxygen atom or a sulfur atom;

$R^1$ and $R^2$ each represents an alkyl group having from 1 to 4 carbon atoms, an alkoxy group having from 1 to 4 carbon atoms, an alkoxycarbonyl group having from 2 to 5 carbon atoms, an acyloxy group having from 2 to 5 carbon atoms, an acyl group having from 2 to 4 carbon atoms, an amide group having from 2 to 5 carbon atoms, a cyano group or a halogen atom; and n1 and n2 each indicates an integer of from 0 to 4;

$R^3$ represents a hydrogen atom, or an alkyl group having from 1 to 4 carbon atoms;

$Z^1$ represents —COO—, —OCO—, —COS—, —SCO— or —NHCO—;

$L^1$ represents —COO—, —OCO—, —COS—, —SCO—, —OCO—CH=CH— or —NHCO—; and n is 0, 1 or 2.

2. The compound according to claim 1, wherein in the formula (I), n=0.

3. The compound according to claim 2, wherein in the formula (I), $L^1$ is —OCO— or —OCO—CH=CH—.

4. The compound according to claim 1, wherein in the formula (I), n=1.

5. The compound according to claim 4, wherein in the formula (I), $Z^1$ is —COO— and $L^1$ is —OCO—.

6. The compound according to claim 1, wherein in the formula (I), $P^1$ and $P^2$ each is a polymerizable group represented by the formula (P-1).

7. The compound according to claim 1, wherein in the formula (I), m1 and m2 each is from 3 to 6.

8. The compound according to claim 1, wherein, of m1 or m2 $CH_2$'s, one $CH_2$ or two or more $CH_2$'s not adjacent to each other are replaced by an oxygen atom or a sulfur atom.

9. A polymer produced by polymerizing a polymerizable composition containing at least one compound represented by the following formula (I):

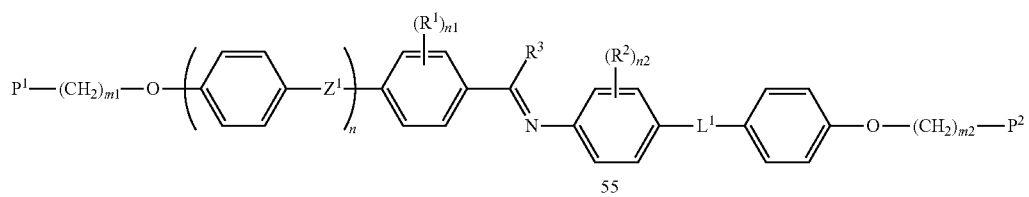
(I)

wherein $P^1$ and $P^2$ each represents a polymerizable group selected from the groups represented by the following formulae (P-1) to (P-5):

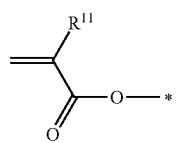
(P-1)

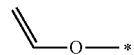
(P-2)

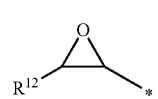
(P-3)

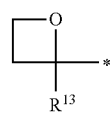
(P-4)

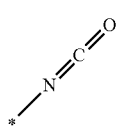
(P-5)

wherein $R^{11}$ to $R^{13}$ each represents a hydrogen atom or a methyl group;

m1 and m2 each indicates an integer of from 2 to 8, and of m1 or m2 $CH_2$'s, one $CH_2$ or two or more $CH_2$'s not adjacent to each other may be replaced by an oxygen atom or a sulfur atom;

$R^1$ and $R^2$ each represents an alkyl group having from 1 to 4 carbon atoms, an alkoxy group having from 1 to 4 carbon atoms, an alkoxycarbonyl group having from 2 to 5 carbon atoms, an acyloxy group having from 2 to 5 carbon atoms, an acyl group having from 2 to 4 carbon atoms, an amide group having from 2 to 5 carbon atoms, a cyano group or a halogen atom; and n1 and n2 each indicates an integer of from 0 to 4;

$R^3$ represents a hydrogen atom, or an alkyl group having from 1 to 4 carbon atoms;

$Z^1$ represents —COO—, —OCO—, —COS—, —SCO— or —NHCO—;

$L^1$ represents —COO—, —OCO—, —COS—, —SCO—, —OCO—CH=CH— or —NHCO—; and n is 0, 1 or 2.

10. The polymer according to claim 9, wherein the polymerizable composition further contains at least one chiral compound.

11. A film containing at least one polymer produced by polymerizing a polymerizable composition containing at least one compound represented by the following formula (I):

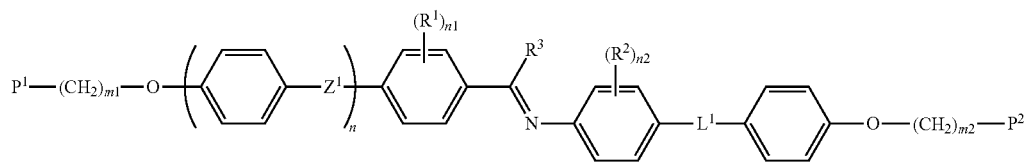
(I)

wherein $P^1$ and $P^2$ each represents a polymerizable group selected from the groups represented by the following formulae (P-1) to (P-5):

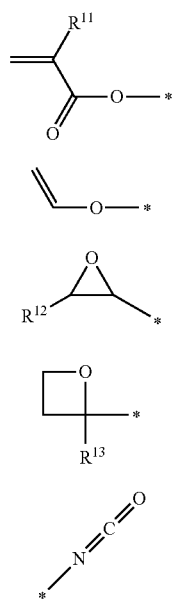

(P-1)

(P-2)

(P-3)

(P-4)

(P-5)

wherein $R^{11}$ to $R^{13}$ each represents a hydrogen atom or a methyl group;

m1 and m2 each indicates an integer of from 2 to 8, and of m1 or m2 $CH_2$'s, one $CH_2$ or two or more $CH_2$'s not adjacent to each other may be replaced by an oxygen atom or a sulfur atom;

$R^1$ and $R^2$ each represents an alkyl group having from 1 to 4 carbon atoms, an alkoxy group having from 1 to 4 carbon atoms, an alkoxycarbonyl group having from 2 to 5 carbon atoms, an acyloxy group having from 2 to 5 carbon atoms, an acyl group having from 2 to 4 carbon atoms, an amide group having from 2 to 5 carbon atoms, a cyano group or a halogen atom; and n1 and n2 each indicates an integer of from 0 to 4;

$R^3$ represents a hydrogen atom, or an alkyl group having from 1 to 4 carbon atoms;

$Z^1$ represents —COO—, —OCO—, —COS—, —SCO— or —NHCO—;

$L^1$ represents —COO—, —OCO—, —COS—, —SCO—, —OCO—CH═CH— or —NHCO—; and n is 0, 1 or 2.

12. The film according to claim 11, wherein the polymerizable composition further contains at least one chiral compound, and the film is produced by fixing the cholesteric liquid-crystal phase of the polymerizable composition.

13. The film according to claim 11, which shows optical anisotropy.

14. The film according to claim 11, which shows selective reflection characteristics.

15. The film according to claim 14, which shows selective reflection characteristics in the IR wavelength range.

16. The film according to claim 11, which is colorless.

* * * * *